United States Patent [19]
Yu et al.

[11] Patent Number: 5,712,112
[45] Date of Patent: *Jan. 27, 1998

[54] GENE EXPRESSION SYSTEM COMPRISING THE PROMOTER REGION OF THE ALPHA-AMYLASE GENES

[75] Inventors: Su May Yu; Li Fei Liu; Ming Tsair Chan, all of Taipei, Taiwan

[73] Assignee: National Science Council of R.O.C., Taipei, Taiwan

[*] Notice: The term of this patent shall not extend beyond the expiration date of Pat. No. 5,460,952.

[21] Appl. No.: 343,380

[22] Filed: Nov. 22, 1994

Related U.S. Application Data

[63] Continuation of Ser. No. 973,324, Nov. 4, 1992, Pat. No. 5,460,952.
[51] Int. Cl.$^6$ .......................... C12P 21/06; C12P 21/02; C12N 5/00; C12N 15/00
[52] U.S. Cl. .................. 435/69.1; 435/69.7; 435/69.8; 435/70.1; 435/172.3; 435/410; 435/420; 536/23.1; 536/23.6; 536/24.1; 935/35; 935/60; 935/67
[58] Field of Search ...................... 435/69.1, 69.7, 435/69.8, 70.1, 172.1, 172.3; 410/240.4, 240.45, 240.46; 425/240.4, 240.45, 240.46; 536/24.1, 23.1, 23.6; 935/35, 60, 67

[56] References Cited

U.S. PATENT DOCUMENTS 5,460,952  10/1995  Yu et al. ................... 435/69.1

OTHER PUBLICATIONS

Akazawa et al., "Topographic Aspects of Biosynthesis, Extracellular Secretion, and Intracellular Storage of Proteins in Plant Cells", *Ann. Rev. Psychol.*, 36:441–472 (1985).

An et al., "Transformation of Tobacco, Tomato, Potato, and *Arabidopsis thaliana* Using a Binary Ti Vector System", *Plant Physiol.*, 81:301–305 (1986).

Baulcombe et al., "A Novel Wheat α-amylase Gene (αAmy3)," *Mol. Gen. Genet.*, 209:33–40 (1987).

Belanger et al., "Heat Shock Causes Destabilization of Specific mRNAs and Destruction of Endoplasmic Reticulum in Barley Aleurone Cells", *Proc. Nat'l. Acad. Sci. (USA)*, 83:1354–1358.

Benfey et al., "The CaMV 35S Enhancer Contains at Least Two Domains Which can Confer Different Developmental and Tissue–Specific Expression Patterns", *EMBO Journal*, 8:2195–2202.

(List continued on next page.)

Primary Examiner—Bruce R. Campell
Attorney, Agent, or Firm—Marshall, O'Toole, Gerstein, Murray & Borun

[57] ABSTRACT

The present invention is directed to a method for producing a gene product by expressing a gene encoding the gene product in angiosperm host cells, comprising the steps of constructing a vector expressible in angiosperm host cells, the vector comprising a promoter region derived from an α-amylase gene of a plant, and a gene encoding a desired gene product; transforming a compatible angiosperm host cell with the vector; cultivating the resultant transformant host cell; subjecting the cultivated transformant host cell to a sugar-depleted or sugar-free condition to promote the expression of the gene under the control of the promoter region; and recovering the expressed gene product. The present invention also is directed to a method for the production of a transgenic plant of rice crop comprising the steps of infecting an immature embryo of rice crop with the genus Agrobacterium for transformation; co-culturing the infected embryo with a dicot suspension culture during the step of transformation; allowing the transformed embryo to grow into a callus in a selective medium comprising a sufficient amount of a plant growth hormone for the growth of rice crop; and allowing the cultured callus to regenerate root and shoot in a regeneration medium comprising a pre-determined amount of nutrients for the growth of rice crop. The invention is further directed to a transformed rice plant made by methods of this invention.

42 Claims, 25 Drawing Sheets
(2 of 15 Drawing(s) in Color)

OTHER PUBLICATIONS

Bevan, "Binary *Agrobacterium* Vectors for Plant Transformation", *Nucleic Acids Research*, 12:8711–8721 (1984).

Briggs, D. "Barley Germination: Biochemical Changes and Hormonal Control" in *Barley: Genetics, Biochemistry, Molecular Biology & Biotechnology*, Shewry, P.R. (ed.) CAB Int'l 02/1992.

Bytebier et al., "T–DNA Organization in Tumor Cultures and Transgenic Plants of The Monocotyledon *Asparagus officinalis*", *Proc. Nat'. Acad. Sci. (USA)*, 84:5345–5349 (Aug. 1987).

Chan et al., "Transformation of Indica Rice (*Oryza sativa* L.) Mediated by *Agrobacteruim tumefaciens*", *Plant Cell Physiol.*, 33(5):577–583 (1992).

Chandler et al., "The Effects of Gibberellic Acid and Abscisic Acid on α-amylase mRNA levels in Barley Aleurone Layers Studies Using an α-amylase cDNA Clone", *Plant Mol. Biol.*, 3:407–418 (1984).

Chang et al., "*Agrobacterium tumefaciens*–Mediated Transformation of Soybean (*Glycine max* (L.) Merr.) is Promoted by the Inclusion of Potato Suspension Culture",*Bot. Bull. Adademia Sinica* 32:171–178 (1991).

Christou, et al., "The Development of a Variety–Independent Gene–Transfer Method for Rice", *Tibtech*, 10:239–246 (Jul. 1992).

Dale et al., "Agroinfection of Wheat: Inoculation of In Vitro Grown Seedlings and Embryos",*Plant Science*, 63:237–245 (1989).

Datta et al., "Genetically Engineered Fertile Indica–Rice Recovered From Protoplasts", *Biotechnology* 8:736–740 (Aug. 1990).

Deikman et al., "Control of α–Amylase mRNA Accumulation by Gibberellic Acid and Calcium in Barley Aleurone Layers", *Plant Physiol.*, 78:192–198 (1995).

Depicker et al., "Molecular Cloning of Overlapping Segments of the Noplaine TiPlasmid pTiC58 as a Means to Restriction Endonuclease Mapping", *Plasmid*, 3:193–211 (1980).

Garfinkel et al., "*Agrobacterium tumefaciens* Mutants Affected in Crown Gall tumorigenesis and Octopine Catabolism", *Journal of Bacter.*, 144920:732–743 (Nov. 1980).

Gillies et al., "A Tissue–Specific Transcription Enhancer Element is Located in the Major Intron of a Rearrranged Immunoglobulin Heavy Chain Gene", *Cell*, 33:717–728 (Jul. 1983).

Gould et al., "Transformation of Zea *mays*. Using *Agrobacterium tumefaciens* and the Shoot Apex", *Plant Physiol.*, 95:426–434 (1991).

Hain et al., "Uptake, Integration, Expression and Genetic Transmission of a Selectable Chimaeric Gene by Plant Protoplasts", *Mol. Gen. Genet.*, 199:161–168 (1985).

Hernalsteens et al., "An *Agrobacterium*–transformed Cell Culture from the Monocot *Asparagus officinalis* ", *EMBO Journal*, 3(13):3039–3041 (1984).

Ho et al., "Regulation of Gene Expression in Barley Aleurone Layers", *Mol. Biol. of Plant Growth Control*, Alan R. Liss, Inc., pp. 35–49 (1987).

Holsters et al., "Transfection and Transformation of *Agrobacterium tumefaciens*", *Molec. Gen. Genet.*, 163:181–187 (1978).

Hooykaas, "Transformation of Plant Cells via *Agrobacterium*", *Plant Molecular Biology* , 13:327–336 (1989).

Horsch et al., "A Simple and General Method for Transferring Genes into Plants", *Science*, 227:1229–1231 (Mar. 1989).

Huang et al., "Classification and Characterization of the Rice α–Amylase Multigene Family", *Plant Molecular Biology*, 14:655–668 (1990).

Huang et al., "Structural Organization and Differential Expression of Rice α–Amylase Genes", *Nucleic Acids Research*, 18(23):7007–7014 (1990).

Janssens et al., "Plant Cells Induce Transcription of the *Agrobacterium Tumefaciens* Nopaline pTiC58 Virulence Region", *Plant Science* , 47:185–193 (1986).

Johnson et al., "Glycine Potentiates the NMDA Response in Cultured Mouse Brain Neurons", *Nature* , 325:529–531 (Feb. 1987).

Karrer et al., "Differential Expression of α–Amylase Genes in Germinating Rice and Barley Seeds", *Plant Molecular Biology* , 16:797–805 (1991).

Khursheed et al., "Barley α–Amylase Genes", *J. Biol. Chem.*, 263(35):18953–18960 (Dec. 15, 1988.

Kim et al., "Nucleotide Sequence of a High–pI Rice (*Oryza sative*) –Amylase Gene", *Plant Molecular Biology*, 18:399–402 (1992).

Knox et al., "Structure and Organization of Two Divergent α–amylase Genes from Barley", *Plant Molecular Biology*, 9:3–17 (1987).

Kumagai et al., "Expression and Secretion of Rice α–amylase by *Saccharomyces cerevisiae*", *Gene*, 94:209–216 (1990).

Lanahan et al., "A Gibberellin Response Complex in Cereal α–Amylase Gene Promoters", *The Plant Cell*, 4:203–211 (Feb. 1992).

McElroy et al., "Structural Characterization of a Rice Actin Gene", *Plant Molecular Biology*, 14:163–171 (1990).

O'Neill et al., "The a–amylase Genes in *Oryza sativa*: Characterization of cDNA Clones and mRNA Expression During Seed Germination", *Mol. Gen. Genet.*, 221:235–244 (1990).

Radke et al., "Transformation of *Brassica napus* L. using *Agrobacterium tumefaciens*: Developmentally Regulated Expression of a Reintroduced Napin Gene", *Theor. Appl. Genet.*, 75:685–694 (1988).

Raineri et al., "Agrobacterium–Mediated Transformation of Rice (*Oryza SativaL.*)", *Biotechnology* 8:33–38 (Jan. 1990).

Rogers, "Two Barley α–Amylase Gene Families are Regulated Differentally in Aleurone Cells", *J. Biol. Chem.*, 260(6):3731–3738 (Mar. 25, 1985).

Rogers et al., "Coordinate Increase in Major Transcripts from the High pI α–Amylase Multigene Family in Barley Aleurone Cells Stimulated with Gibberellic Acid", *J. Biol. Chem.* 259(19):12234–12240 (Oct. 10, 1984).

Sahi et al., "Corn Metabolites Affect Growth and Virulence of *Agrobacterium tumefaciens*", *Proc. Nat'l Acad. Sci. (USA)*, 87:3879–3883 (May 1990).

Salisbury et al., "Respiration", *Plant Physiology*, 2nd Edition, pp. 174–177 (1978).

Schafer et al., "T–DNA Integration and Expression in a Monocot Crop Plant after Induction of *Agrobacterium*", *Nature*, 327:529–532 (Jun. 1987).

Schlappi et al., "Competence of Immature maize Embryos for Agrobacterium–Mediated Gene Transfer", *The Plant Cell*, 4:7–16 (Jan. 1992).

Stachel et al., "Identification of the Signal Molecules Produced by Wounded Plant Cells that Activate T-DNA Transfer in *Agrobacterium tumefaciens*", *Nature*, 318:624-629 (Dec. 1985).

Sutliff et al., "Characterization of an α-Amylase Multigene Cluster in Rice", *Plant Molecular Biology*, 16:579-591 (1991).

Usami et al., "Factor Inducing *Agrobacterium tumefaciens* vir Gene Expression is Present in Monocotyledonous Plants", *Proc. Nat'l Acad. Sci. (USA)* 85:3748-3752 (Jun. 1988).

Weiher et al., "Multiple Point Mutation Affecting the Simian Virus 40 Enhancer", *Science*, 219:626-631 (Feb. 1983).

Yu et al., "Metabolic Depression of α-Amylase Gene Expression in Suspension-Cultured Cells of Rice", *J. Biol. Chem.*, 266:21131-21137 (Nov. 5, 1991).

Yu et al., "Regulation of α-amylase-encoding Gene Expression in Germinating Seeds and Cultured Cell of Rice", *Gene*, 122:247-253 (1992).

Zaenen et al., "Supercoiled Circular DNA in Crown-gall Inducing *Agrobacterium* Strains", *J. Mol. Biol.*, 86:109-127 (1974).

Ashikari, et al., "Rhizopus Raw-Starch-Degrading Glucoamylase: Its Cloning and Expression in Yeast, " *Agric. Biol. Chem.*, 50(4):957-964 (1986).

During, et al., "Synthesis and self-assembly of a functional monoclonal antibody in transgenic *Nicotiana tabacum*" *Plant Molecular Biology* 15:281-293 (1990).

Hiatt, et al., "Production of antibodies in transgenic plants," *Nature* 342:76-78 (Nov. 2, 1989).

Krebbers et al., "Production of Peptides in plant seeds, " *TIBETCH*, 8:1-3 (Jan. 1990).

Pen et al., "Production of Active *Bacillus Licheniformis* Alpha-Amylase in Tobacco and Its Application in Starch Liquefaction , " *Bio/Technology* 10:292-296 (Mar., 1992).

Sijmons, et al., "Production of Correctly Processed Human Serum Albumin in Transgenic Plants," *Bio/Technology* 8:217-221 (Mar., 1990).

Ueda, "Fungal glucoamylases and raw starch digestion, " *TIBS*, pp. 89-90 (Mar., 1981)

Vandekerckhove, et al., "Enkephalins Produced in Transgenic Plants Using Modified 2S Seed Storage Proteins, " *Bio/Technology* 7:929-932 (Sep. 1989).

Wanbelt, et al., "Vicilin with carboxy-terminal KDEL is retained in the endoplasmic reticulum and accumulates to high levels in the leaves of transgenic plants, " *The Plant Journal*, 2(2):181-192 (1992).

```
                           1                                                          60
αAmy6-C       CCCGGGAGCAAGCTGAAAATCCTGCTGCTGAGGGAGAGGTCTATGTCGCCA
αAmy8-C       GGATCCATG*G*****C***G*C***CAAGC*****G*A**C***
αAmy7-C       *******CG*CAGGG*CGC***A*G*AA****CA*CTCCC**GG
αAmy10-C      *******CG*C**G*CGT*C*******A*G*A****CA*CTCCC**G 61                                                         120
αAmy6-C       TGATCGATGATAAGTCATAAACAAAGATTGGGACACGGTATGACGTGGGCAACTTAATCC
αAmy8-C       *********C*GC**GC****C*C**GAC**CC*GGGA*C****
αAmy7-C       A******G*C*GC*******ACAC*AC***C*AAC**C*C****
αAmy10-C      A********C*GA********C*AG**C*AC**A*G*C****C****C*AGC***C****

121                                                        180
αAmy6-C       CGTCAGACTTCCATGTCGTTGCTCTCACGGCAACAATTACTGCATTTGGGAAAAGAGCCGGTC
αAmy8-C       *C******************GC***G*C**GGAA*------
αAmy7-C       *CGA***G*****C*G****TG*TGGC***GCA*C******G**-------
αAmy10-C      *CGA*G*G******C*T*TGGGCC***CG-------

181                                                        240
αAmy6-C       TCAGAGTTCCTGCAGGGGCGGCACCACTATTAGGCGAAGAAAATTTTCAGGACTATTGG
αAmy8-C       ****G*****G*******CC**TA*AA*G*****TAGCTTT**CT*TAGCGATC*AGT*GCA***
αAmy7-C       --------AAT*TGA****CACGATGACGAGACTCTCAGTTTAGCAGATTT*ACC*GC*A
αAmy10-C      --------AAT*TGA****TGGAGAGGCACAATT*GC*G*T**A*TTACCTGCAATTT
                         "PstI"
```

FIG. 1A

```
            241                                                        300
αAmy6-C     TGCCTGGAA---TAAGATTTGAATTATATCCTAAATAACCAG------ATTATGATTGT
αAmy8-C     ***T*T*C*ACCCT***AAT*TA***CGTACGTGGCT*TA------GC****A*CA
αAmy7-C     *TT*ACCCTGACCG*TA*ACGTA****CGTGCCGGC*A*GA------GCTG*ATCC*A
αAmy10-C    *TCCCACCCTCGACGT*TAAC*TA**C*GTG*TGGC*A*GAGTTGTATGC*G*ATC**A 301                                                        360
αAmy6-C     ATGAGATTTCTAATCTGAGCAAAGCGTTGAGCATTGC*C------CGATATTTCTATGTATT
αAmy8-C     TGC*AT****GC*GCGAGAT*TGT*CGAGC****T*C*A*GATGT*CGC***GT*AT*AC
αAmy7-C     TCCGA***A*GG*TG*AATTGTCCA**AA*TA*T*CCTC*GTAAATAAAG*GAGGA*CAG
αAmy10-C    TCTGA*C*ATG***CG*GATTGTCCA*AAA*TA*TACCTC*GTAAATAAAG*GAGGA***G
                                                "ScaI"  "PvuI"

361                                                        420
αAmy6-C     CTACCTGCCTGGGATATGATATTTGTATCCTCTAGAAGTAAAGATGATTTAACTC(A)n
αAmy8-C     TAG*G*T*T*C**A*ATAAG*AGC*G*ATG*ACCCTGTTCCCAGAA*TG*AGGA
αAmy7-C     GG***A*ACA*TT*T**GGTT*TACGAATAATG*TGCAATATTGCACTGTAAT
αAmy10-C    GA*A**G*TT*CGCATGG*T(A)n 421             458
αAmy8-C     TGAATGGAATTAACTAGCTACTGTTCGTTTCGATCCTC(A)n
αAmy7-C     GCTTAT*C***TTTGCTTGGT*C(A)n
```

FIG. 1B

FRAGMENT

```
         -209                                           -170
A        TGGAGCCCACAACGCTATCCAAGGCTTTATCTAACTTCCT

-169                              ********     -130
B        ATTGGCCTCCTTTTTATCCTCTTTTAAATGAGCGCAACTC

-129                                           -90
C        GTCGCCGTGCCGTTGCGTTTCTCGTTAGGAGCAACTGAAC
                     -----------
```

FIG. 5C

GENE EXPRESSION SYSTEM COMPRISING THE PROMOTER REGION OF THE ALPHA-AMYLASE GENES

This patent application is a continuation of U.S. patent application Ser. No. 07/973,324, filed Nov. 4, 1992, U.S. Pat. No. 5,460,952.

FIELD OF THE INVENTION

This invention relates to a method for producing a gene product, in particular to a method for the mass production of a desired gene product by expressing a gene encoding said gene product in plant host cells, whereby said desired gene product can be recovered from the culture medium of said plant host cells.

BACKGROUND OF THE INVENTION

The plant cell culture expression system has several advantages over the bacterial, yeast or Baculovirus expression systems. Bacteria do not, and yeasts only limitedly, carry out post-translational modifications of the expressed proteins. Plant cells are eukaryotic and able to perform sophisticated protein modifications which are often necessary for the proper function of proteins.

Although Baculovirus is a potent transformation vehicle for higher eukaryotes and generally performs satisfactory modifications of proteins, the cost for culturing baculovirus is much higher than that for plant cells. In addition, the host cells are eventually lysed by Baculovirus and thousands of host proteins along with the expressed transformation protein are mixed and released into the culture medium, which makes purification of the expressed transformation protein difficult.

The culture medium for plant cells contains mainly salts and vitamins and therefore, it costs much less than that used to culture insect cell lines which are used for the Baculovirus transfection. Moreover, the culture medium for plant cells will not need a supply of serum, whereas almost all animal cell cultures cannot survive without serum. In addition, since plant cells are eukaryotes, the expressed proteins therein will be appropriately post-translationally modified so as to render said proteins capable of functioning and being secreted out of the plant cells. Although no one has yet made a deeper understanding of the mechanism of protein secretion in plant cells, the common belief at present is that it could be similar to the secretory mechanism in animals.

Plant cell cultures are a potential commercial source of medicines, dyes, enzymes, flavoring agents and aromatic oils. Plant cell culture production of such compounds are sought when (1) they are produced by the plant in small quantities or in fleeting or unharvestable developmental stages of the plant's life cycle; (2) when they are produced by plants which are not amenable to agriculture or are native to vanishing or inaccessible environments; and (3) when the compounds cannot be satisfactorily synthesized in vitro or by other biosynthesis systems.

Attempts to produce products by plant cell culture, however, are often commercially unsuccessful due to such factors as insufficient production and secretion of the desired product, poor cell growth, and difficulties in maintaining the appropriate cell type in culture.

The callus alpha-amylase (α-amylase) expression system has features which make it of potential use to plant cell fermentation technology, namely its high level of expression, sustained expression, expression irrespective of either the tissue of origin of the cell culture or tissue formation in the cell culture, and its product secretion. Although rice callus itself may not be an ideal source of commercial α-amylase, the gene regulatory regions responsible for the high expression could be used, with the aid of recombinant DNA technology and plant transformation, to achieve high expression of other valuable proteins (Carl R. Simmons, et al (1991), Biotechnology and Bioengineering, 38: 545–551).

Starch includes straight-chain starch and branched starch, two types of polysacchardies, and is the basic stored nutrient component in cereal grains (T. Akazawa et al (1985), Ann. Rev. Plant Physiol., 36: 441–472). During the initial germinating period of cereal seeds, the aleurone layer cells will synthesize α-amylase. Alpha-amylase, α-glucosidase and enzymes restricting dextrinase are secreted into the endosperm and together hydrolyze starch to form glucose and maltose, so as to provide the nutrients needed for the growth of the germ (J. C. Rogers and C. Milliman, J. Biol. Chem., 259 (19): 12234–12240, 1984; Rogers, J. C., J. Biol. Chem., 260: 3731–3738, 1985). Other enzymes contributing to starch hydrolysis include β-amylase which can hydrolyze starch to form maltose and a small amount of glucose. In a dry seed, β-amylase normally exists in an inactive form in the endosperm due to protein disulfide bonding. When the seed germinates, the aleurone layer cells will be subjected to the induction by gibberellic acid ($GA_3$) to produce protease, which can destroy the disulfide bond and release the active form of β-amylase. The above four enzymes take part in the hydrolysis of starch during the germination of seeds. However, α-amylase is the most active and holds the most important role (Akazawa, T., et al (1985), Ann. Rev. Plant Physiol., 36: 441–472).

It is known that $GA_3$ exerts a direct influence over the expression of α-amylase (Chandler, P. M., et al (1984), Mol. Biol., 3: 401–418). When rice seeds are treated with $GA_3$, the new synthesis of α-amylase mRNA by the aleurone layer cells increases to 50 to 100-fold of the control value (no $GA_3$) (O'Neill, S. D., et al (1990), Mol. Gene. Genet., 221: 235–244). In reality, the regulation of α-amylase gene expression by $GA_3$ has provided a very ideal model for studying the mechanism of hormonal regulation of gene expression in plants (Ho, T. H. D., et al (1987), "Regulation of gene expression in barley aleurone layers," In: *Molecular Biology of Plant Growth Control*, pp.35–49. St. Louis, Mo.: Alan R. Liss, Inc.).

Hitherto, α-amylase genes from rice, barley and wheat have been cloned and subjected to further study and analysis. The results show that these cereal-type α-amylase isozymes or isoforms are all manufactured by several types of α-amylase genes (Baulcombe, D. C., et al (1987) Mol. Gen. Genet., 209: 33–40); Huang, N., et al (1990a), Plant Mol. Biol., 14: 655–668; Knox, C. A. P., et al (1987), Plant Mol. Biol., 9: 3–17).

The α-amylase secreted from the aleurone layer cells during the germinating period of the seed of barley and wheat comprises two classes, the high isoelectric point and low isoelectric point. In barley, there are around 7 α-amylase genes which belong to the high isoelectric point and 3–4 genes which belong to the low isoelectric point (B. Khursheed and J. C. Rogers, J. Biol. Chem., 263: 18593–18960, 1988).

Currently, 7 α-amylase cDNA and 9 α-amylase genomic DNA groups of barley have been cloned (Chandler, P. M., et al (1984), Plant. Mol. Biol., 3: 401–418; J. Deikman and R. L. Jones, Plant Physiol., 78: 192–198, 1985; Khrusheed &

Rogers (1988), supra; Knox, C. A. P., et al (1987), supra). The α-amylase genes of wheat are grouped into α-Amy1, α-Amy2 and α-Amy3. Alpha-Amy1 has a high isoelectric point while α-Amy2 has a low isoelectric point, and each has more than 10 genes which are expressed in germinating seeds. Alpha-amylase α-Amy3 includes 3-4 genes which are expressed in immature seeds (Baulcombe et al (1987), supra).

With regard to the study of rice α-amylase genes, the α-amylase genes thereof have not been classified into the high isoelectric point group and the low isoelectric point group as was done in the study of barleys and wheats. In reality, MacGregor, A. W., et al (Cereal Chem., 65: 326, 1988) applied the analytical method of isoelectric point electrophoresis and found that rice α-amylase isomers had a pI value of less than 5.5.

Therefore, it is possible that rice does not have any isoform of high isoelectric point. Huang, N., et al (Nucl. Acids. Res., 18: 7007–7014, 1990b) grouped the 10 rice α-amylase genes into 5 groups by cross hybridization experiment and confirmed their distribution in 5 chromosomes (Ranjhan et al, the original manuscript is still under preparation). O'Neill et al (Mol. Gene. Genet. 221: 235–244, 1990) made the first more detailed study of the cDNA pOS103 and pOS137 of rice α-amylase. The α-amylase manufactured from pOS103 and pOS137 has a precursor protein of a molecular weight of 48 KDa.

When this enzyme is secreted out of the cell, the signal peptide chain of the precursor protein will be cleaved off. Accordingly, the molecular weight of mature α-amylase is about 45–46 KDa and the isoelectric point thereof is predicted to be about 6.0. However, Kumagai, M. H., et al (Gene, 94: 209–216, 1990) subcloned pOS103 into the cells of Saccharomyces, to allow the Saccharomyces to secrete α-amylase into the culture medium, and it was found that the molecular weight of α-amylase is about 44–45 KDa and that the isoelectric point is about 4.7 to 5.0.

On the other hand, transformation of dicotyledonous plants with Agrobacterium tumefaciens is well established and widely used. A number of foreign genes carried between the T-DNA borders of the Ti plasmid in Agrobacterium have been delivered to plant cells, integrated into the chromosome, and stably inherited by subsequent generations. This, however, has not been the case for monocotyledonous plants in general. In the past, the monocots and particularly the graminaceous crop species have been considered to be outside the Agrobacterium host range (Bevan, M. W., Nucl. Acids Res., 12: 8711–8721, 1984; Declene, M., Phytopathol. Z. 113: 81–89). Gene transfer methods developed from economically important monocotyledonous species have been restricted to the directed transfer of DNA into protoplasts, or particle discharge methods of direct DNA transfer into intact cells of embryomic callus or suspension cells.

In recent years, more and more data on the transformation of monocots using Agrobacterium have been accumulated. The demonstration of Agrobacterium T-DNA integration into genomic DNA of *Asparagus officinalis* (Bytebier., B., et al (1987), Proc. Natl. Acad. Sci. USA, 84:5345–5349) and *Dioscorea bulbifera* (Schafer, W., et al (1987), Nature, 327: 529–531) first indicated that some monocot species possess the potential to be transformed by Agrobacterium. Later, a report of T-DNA integration into the genomic DNA of rice, *Oryzae sativa* (Raineri, D. M., et al (1990), Biotechnology, 8: 33–38), further showed that graminaceous crop plants can be transformed by Agrobacterium. Recently, foreign genes have been successfully transferred into corn, and regeneration of plants and detection of the transferred genes in the F1 progeny have been demonstrated (Gould, J. et al (1991), Plant Physiol., 95: 426–434). Therefore, the Agrobacterium-mediated gene transfer system seems to be applicable for transformation of monocot plants.

Agrobacterium-mediated transformation is a complex process and several factors are involved (for review, see Hooykaas, P. J. J., Plant Mol. Biol., 13: 327–336, 1989). Activation of the virulence system is one of the early important steps in plant tumor induction (Garfinkrl, D. J., J. Bacteriol., 144: 732–743, 1980). The vir genes on the Ti plasmid are silent until they become induced by certain plant factors, which in tobacco have been identified as the phenolic compounds acetosyringone and α-hydroxyacetosyringone (Stachel, S. E., et al (1985), Nature, 318: 624–629). These compounds are released from plant tissue, especially after wounding, which has long been known to be a prerequisite for plant tumorigenesis via Agrobacterium. Although initially, it was generally thought that monocot species were not susceptible to Agrobacterium, some monocot species (e.g., Asparagus) are prone to tumor formation after T-DNA transfer (Hernalsteens, J. P., et al (1984), EMBO J., 3: 3039–3041). Tumor formation on discs of the monocot Dioscorea (yam) by Agrobacterium requires a pre-incubation with exudates from dicot plants (Schafer, W., et al (1987), Nature, 327: 529–531), indicating that some monocots probably do not produce enough inducers to activate the expression of the vir gene on the Ti plasmid transferred by Agrobacterium.

Toxins or inhibitors which inhibit the growth of *Agrobacterium tumefaciens* and the expresion of vir genes on the Ti plasmid have been shown to be present in wheat (Usami, S., et al (1988), Proc. Natl. Acad. Sci. USA, 85: 3748–3752), and corn (Sahi, S. U., et al (1991), Proc. Natl. Acad. Sci. USA, 87: 3879–3883), and might cause problems during attempts to transform monocots with Agrobacterium. Nevertheless, wheat and oats have been shown to contain substances which induce the expression of the vir locus of the Ti plasmid and the T-DNA processing reaction, although the inducing substance of wheat differs from acetosyringone (Usami, S., et al (1988), supra).

Previously, it was reported that potato suspension culture (PSC) is essential for the Agiobacterium-mediated transformation of Indica type rice (Chan, M. T., et al, "Transformation of Indica rice (*Oryza sativa* L.) mediated by Agrobacterium," Plant Cell Physiol. (1992), 33: 577–583). PSC is rich in the phenolic compounds acetosyringone (AS) and sinapinic acid (SA). Although the role of these two compounds in the success or efficiency of transformation is not yet known, the results imply that transformation of monocots, at least rice, using Agrobacterium can be improved by the addition of certain substances.

The age and physiological states of plant tissues have been shown to be important for Agrobacterium-mediated transformation (An, G. et al (1986), Plant Physiol., 81: 301–305; Chan, M. T., et al (1992), supra); H. H. Chang and M. T. Chan, Bot. Bull. Academia Sinica, 32: 171–178, 1991; Dale, P. J., et al (1989), Plant Sci., 63: 237; Gould, J. et al (1991), supra; Hernalsteens J. P., et al (1984), supra).

Thes studies suggest that infection with Agrobacterium and T-DNA transfer should take place in monocots if suitable tissues are used for transformation. It was previously shown that young tissues of rice root have a greater potential to be transformed by Agrobacterium if appropriate conditions are applied (Chan, M. T., et al (1992), supra), and it was assumed that young tissues may contain relatively fewer inhibitors or more virulence inducers. Therefore, a combination of immuture embryos and PSC for transformation of rice can be used in the present invention.

This invention is based on the inventors' discovery that, in addition to regulation by gibberellic acid ($GA_3$) in germinating seeds of rice, the expression of α-amylase genes in suspension-cultured cells of rice is regulated by the level of carbohydrate present in the culture medium (Yu, Su-May et al. (1991), J. Biol. Chem., 266: 21131–21137).

The synthesis of α-amylases and levels of their mRNA are greatly induced under sucrose starvation. An increase of α-amylase synthesis is assumed to accelerate hydrolysis of cellular starch as an energy source when exogenous carbon source is depleted. Under normal growth condition with an adequate supply of sugars in the medium, the expression of α-amylase genes is subject to metabolite repression. It was further observed that α-amylases synthesized by the cultured rice cells are secreted into the culture medium and can account for about 15–20% of the total proteins present in the medium during periods of sugar depletion.

It would therefore be advantageous to develop a gene expression system in plant cell culture by constructing a vector expressible in plant host cells utilizing the promoter and the signal peptide sequences of an α-amylase gene. Any foreign gene can be linked downstream of said promoter and signal peptide encoding sequences. This construct would then be used to transform a compatible plant host cell.

Theoretically, the α-amylase promoter would control the expression of foreign genes in said plant cells and the secretion of the proteins into the medium. Such an expression system therefore has a high potential to express and/or secrete large quantities of any important protein into the medium, greatly facilitating purification of the expressed protein.

To aid in the procedure of screening and/or to enhance further the expression efficiency of the gene expression system constructed above, said gene expression system may further comprise a suitable marker gene, a reporter gene, an antibiotic-resistance gene and/or an enhancer gene, all of which can be those well known by an artisan of ordinary skill in the relevant art (Maniatis, T., et al, "Molecular Cloning: A Laboratory Mannual," pressed by Cold Spring Harbor Laboratory, 2nd edi., 1989).

SUMMARY OF THE INVENTION

Accordingly, in one aspect of the present invention, a method is provided for producing a gene product by expressing a gene encoding said gene product in plant host cells, comprising the steps of: constructing a vector expressible in plant host cells, said vector comprising a promoter region derived from an α-amylase gene of a plant, and a gene encoding a desired gene product; transforming a compatible plant host cell with said vector; cultivating the resultant transformant host cell; subjecting said cultivated transformant host cell to a sugar-depleted or sugar-free condition to promote the expression of said gene under the control of said promoter region; and recovering the expressed gene product.

In another aspect of the present invention, a method is provided for producing a gene product by expressing a gene encoding said gene product in plant host cells, comprising the steps of constructing a vector expressible in plant host cells, said vector comprising a promoter region derived from an α-amylase gene of a plant, and a gene encoding a desired gene product, said promoter region including the promoter and a DNA sequence encoding the signal peptide; transforming a compatible plant host cell with said vector; cultivating the resultant transformant host cell in a suitable culture medium; and directly recovering the-expressed gene product from said medium.

The rice α-amylases are encoded by a multigene family which contains at least ten distinct members. To understand how $GA_3$ and sugars regulate α-amylase gene expression in rice, it is important to identify α-amylase cDNA clones representing different α-amylase genes. These clones, in turn, would be used to isolate their corresponding genomic clones.

In this invention, four of the α-amylase cDNA clones showing different restriction patterns were chosen for subcloning into the plasmid vector pBluescript (Invitrogen, San diego, Calif.). The resultant clones were designated as αAmy6-C (Oryza saliva α-amylase cDNA), αAmy7-C, αAmy8-C and αAmy10-C with insert sizes of 0.6, 1.0, 1.4 and 1.5 kb, respectively.

The 3' end regions of these cDNA clones were further subcloned and sequenced. The sequenced 3' regions of αAmy6-C, αAmy7-C and αAmy8-C are found identical to those of the reported rice α-amylase genes RAmy3B (Sutliff et al., 1991), RAmy1A (Huang et al., 1990a), and RAmy3E (Huang et al., 1990b), respectively. The genomic DNA corresponding to αAmy10-C has not yet been reported.

The expression pattern of these four α-amylase genes in cultured suspension cells of rice was determined with the use of the constructed gene-specific probes. Expression of αAmy7-C and αAmy8-C was induced by sugar depletion 6- and 37-fold, respectively, at day 12 and continued to increase at day 14. Expression of αAmy10-C was induced later with a 5-fold increase at day 14. Expression of αAmy6-C also increased 4-fold at day 12, however, it decreased to basal level at day 14. Expression of another α-amylase gene, αAmy3-C, was increased 5-fold after sugar starvation (S. M. Yu, unpublished result).

Therefore, among the five α-amylase genes examined so far, αAmy8-C is the most abundantly expressed gene after sugar depletion. In addition, it is worthwhile noting that αAmy8-C is one of the major genes whose transcripts upon inducement by sugar depletion constitute the 40-fold increase of total amylase transcripts as detected with probe of OSamy-C. The results show that expression of the four α-amylase genes in response to carbohydrate starvation in the cultured cells is temporally and quantitatively regulated.

Consequently, an expression vector containing the promoter region of the rice α-amylase gene (αAmy8) was constructed in order to express β-glucuronidase (GUS) in transformed rice cells. A hygromycin resistance gene hph placed downstream of the CaMV 35S RNA promoter is used as a selectable marker.

Different transformation methods, such as electroporation of protoplasts or intact cells, particle bombardment, microinjection method, ultrasonic method, polyethylene glycol-mediated protoplast transformation, poly-L ornithine method, calcium phosphate method (Hain, R. et al (1985), Mol. Gen. Genet., 199: 161–168), and Agrobacterium-mediated transformation system can be applied to deliver the plasmid DNA into rice cells. GUS expression was detected in either bombarded or electroporated cells two days after transfection. The results indicate that the α-amylase promoter-GUS chimeric genes are functional in rice cells.

A reporter gene driven by an α-amylase promoter is further transferred and expressed in a Japonica type of rice (Oryzae sativa L. cv. Tainung 62) using the Agrobacterium-mediated gene transfer system. Said system comprises a plasmid containing chimeric genes of β-glucuronidase (GUS) and neomycin phosphotransferase (NPTII). The transformation efficieny of said Agrobacterium was improved by Co-incubation with potato suspension culture (PSC). The GUS and and NPTII genes, which are under the control of promoters of a rice α-amylase gene (αAmy8) and Agrobacterium nopaline synthase gene (NOS), respectively, were both expressed in transgenic calli and plants. The experimental data demonstrate the successful gene transfer and sexual inheritance of the chimeric genes made in accordance with this invention.

Features and advantages of the present invention will become apparent in the following detailed description with references to the accompanying drawings, in which:

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 1A and 1B show nucleotide sequences of the 3' regions of the rice α-amylase cDNA clones.

FIGS. 5A, 5B and 5C show the binding of aleurone protein extract to the 5' specific DNA fragments of a rice α-amylase gene.

Lane 2: DNA template from plasmid pAG8; Lanes 3–10: DNA template from R1 progenies (no. 1-1 to 1-8) of transgenic rice plant T1.

Figure 14:
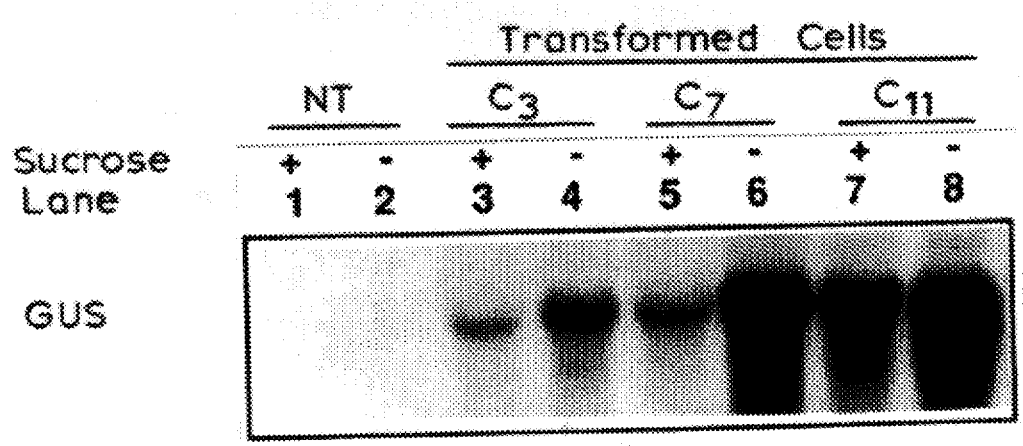

FIG. 14 shows the expression of GUS in transgenic rice calli.

Figure 15:
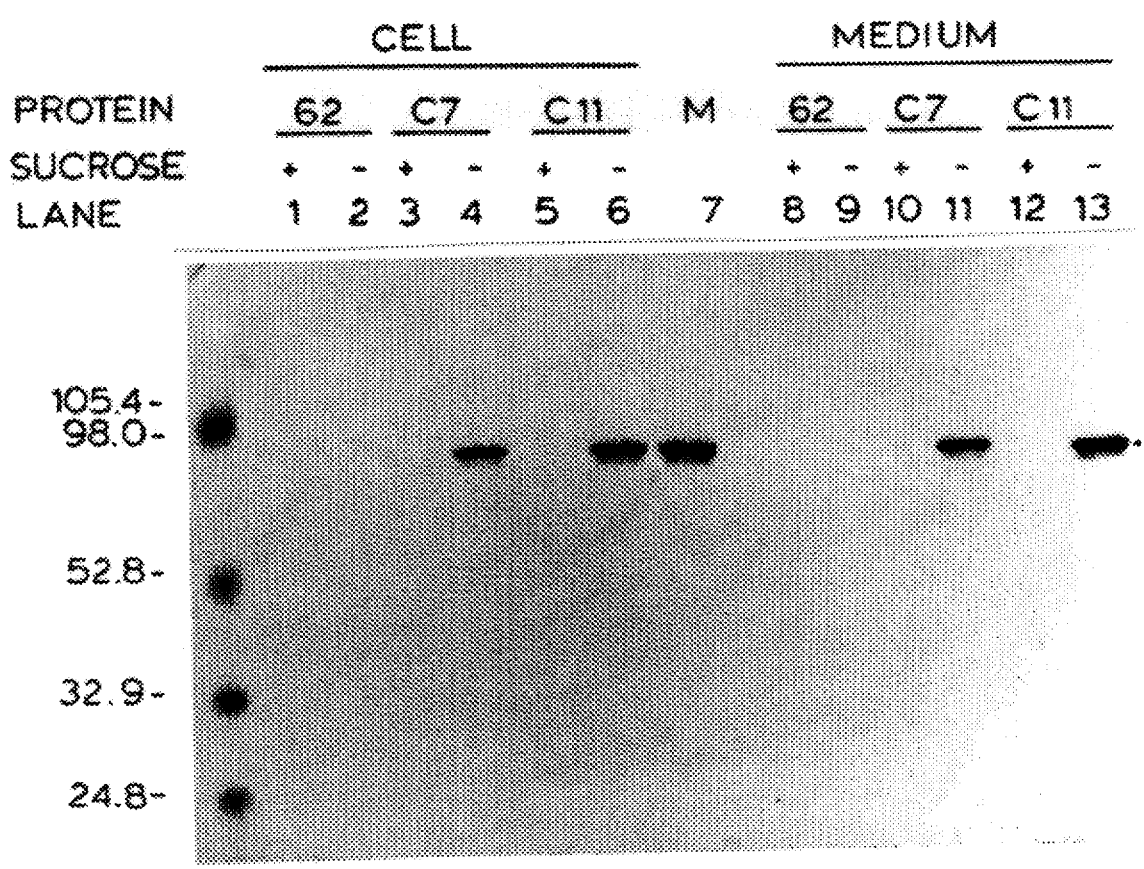

FIG. 15 shows the accumulation of GUS protein in transgenic rice cells and medium.

DETAILED DESCRIPTION OF THE INVENTION

This invention relates to the gene expression regulation of α-amylase promoter, more specifically rice α-amylase promoter, in plant cells and the application thereof.

Alpha-amylases are major amylolytic enzymes for the hydrolysis of stored starch in the endosperm during germination of cereal grains. Previously, we have shown that the expression of α-amylase genes in rice is under two different modes of regulation: I) hormonal regulation in germinating seeds, and II) metabolic repression in cultured cells by available carbohydrate nutrients (Yu, S.M., et al (1991), J. Biol. Chem., 266:21131–21137). Our previous observations suggested a potentially important control-mechanism of carbohydrate metabolism in higher plants, which might account for the repression of α-amylase gene expression in the embryo of germinating rice seeds (Karrer, E. E., et al (1991), Plant Mol. Biol., 16: 797–805).

Thus, to understand the molecular mechanisms which regulate the expression of α-amylase genes in rice, we have used transgenic rice carrying a reporter gene under the control of an α-amylase promoter for fuctional analysis of regulatory element in the α-amylase genes.

To do this, four α-amylase cDNA clones were isolated from a cDNA library derived from poly(A)⁺RNA of giberellic acid (GA₃)-treated rice aleurone layers. Nucleotide sequence analysis indicates that the four cDNAs were derived from different α-amylase genes. Expression of the individual α-amylase gene in germinating seeds and suspension-cultured cells of rice was studied using gene-specific probes.

In germinating seeds, expression of the α-amylase genes is positively regulated by GA₃ in a temporally coordinated but quantitatively distinct manner. In cultured suspension cells, in contrast, expression of the α-amylase genes is negatively and differentially regulated by sugars present in medium. In addition, one strong and one weak carbohydrate-starvation responsive α-amylase genes are identified.

The interactions between the-promoter region (HS501) of a rice α-amlylase gene and GA₃-inducible DNA binding proteins in rice aleurone cells are also studied. DNA mobility-shift assay results showed that aleurone proteins interact with two specific DNA fragments within HS501. One fragment, located between nucleotide residues −131 and −170, contains two imperfect directly-repeated pyrimidine boxes and a putative gibberellin response element. The other fragment, located between residues −92 to −130, contains a putative enhancer sequence. The interactions between aleurone proteins and these two fragments are sequence specific and GA₃ responsive.

We further successfully transferred and expressed a reporter gene driven by an α-amylase promoter in a Japonica type of rice (*Oryzae sativa* L. cv. Tainung 62) using the Agrobacterium-mediated gene transfer system. Immature rice embryos (10–12 days post-anthesis) were infected with Agrobacterium strains carrying a plasmid containing chimeric genes of β-glucuronidase (GUS) and neomycin phosphotransferase (NPTII). Co-incubation of potato suspension culture (PSC) with the Agrobacterium inoculum significantly improved the transformation efficiency of rice.

The GUS and NPTII genes, which are under the control of promotors of a rice α-amylase gene (αAmy8) and Agrobacterium nopaline synthase gene (NOS), respectively, were both expressed in transgenic calli and plants. Integration of foreign genes into the genomes of transgenic plants was confirmed by Southern blot analysis. Histochemical localization of GUS activity in one transgenic plant (T1) revealed that the rice α-amylase promoter functions in all cell types of the mature leaves, stems, sheaths and roots, but not in the very young leaves. This transgenic plant grew more slowly and produced less seeds than the wild type plant. GUS activity was also detected in calli derived from progeny (R1) of this plant. The GUS gene fragment was amplified by polymerase chain reaction using DNA isolated from the R1 progeny of the same transgenic plant. These data demonstrate successful gene transfer and sexual inheritance of the chimeric genes.

Accordingly, in the present invention we describe the transformation of rice with Agrobacterium and the successful expression of an α-amylase promoter-driven reporter gene in a regenerated plant and R1 progeny of a japonica type transgenic rice. To our knowledge, this is the first report to show Agrobacterium-mediated transformation of rice and to demonstrate inheritance of the transferred DNA by the progeny of the transgenic rice. It should therefore be comprehended that the chosen foreign gene (GUS) used in the present invention plays two roles in the present gene expression system: as a foreign gene to be inserted into the present gene expression system and as a reporting gene for indicating the successful transformation of said gene expression system.

EXAMPLE I

Methods:

a) Conditions for preparation of aleurone RNA, construction of the cDNA library, and screening for α-amylase cDNA clones were performed as follows:

Rice (*Oryzae sativa* cv. Labelle) seeds were surface sterilized in 2.5% sodium hypochloride for 20 min., washed extensively with sterile distilled H₂O, and incubated in sterile 10 μM GA₃/20 mM CaCl₂/20 mM sodium succinate for different lengths of time. The germinating embryos were cut off and the aleurone layers were peeled off the endosperm. The collected aleurone layers were immediately frozen in liquid N₂ and stored at −70° C. until use. Total RNA was isolated from the frozen aleurone layers according to the method of Belanger, F. C., et al (Proc. Natl. Acad. Sci. USA, 83: 1354–1358, 1986). Poly (A)+RNA was purified with HYBOND-mAP affinity paper (Amersham). One microgram of poly(A)⁺RNA was used to construct a cDNA library in lamda-gt11 using Amersham's cDNA synthesis and cloning systems. The cDNA library consisted of approximately 2×10⁷ independent recombinant clones. Approximately 2×10⁴ plaques were screened using the ³²P-labeled 1.5 kb fragment of the rice genomic clone, OSamy-C (J. K. Kim and R. Wu (1992), Plant Mol. Biol., 18: 399–402). The cDNA clones in lamda-gt11 were cleaved with EcoR I and subcloned into EcoR I site of pBluescript and maintained in *E. coli* strain XL1-B (Stratagene).

DNA sequencing was performed with the dideoxy nucleotide chain termination technique. Referring to FIGS. 1A and 1B, nucleotide sequence analysis and comparisons were carried out using programs from the Sequence Analysis Software Package of the Genetics Computer Group, University of Wisconsin, Version 5.0, June 1987. Nucleotide sequences are aligned and gaps (dash lines) are introduced to maximize sequence similarity. The homologous sequences among the four clones are indicated by asterisks (*). The translation stop codons and polyadenylation signals are underlined. The 5' boundaries of the geneospecific regions are indicated by arrows and the restriction enzymes used for DNA truncation are indicated below their corresponding sites. The nucleotide sequence is numbered from the first base of the sequenced regions. Accession number for αAmy10-C in GeneBank, EMBL, and DDBJ is M81143.

b) Conditions for preparation of $^{32}$P-labeled gene-specific probes were performed as follows:

The four α-amylase cDNAs were truncated at the 5' ends of the gene-specific regions using restriction enzymes indicated in FIGS. 1A and 1B. In vitro transcription of the four truncated cDNAs with the T3 RNA polymerase yields antisense-strand transcripts of sizes 210, 112, 119, and 50 nucleotides, representing αAmy6-C-3', αAmy7-C-3', αAmy8-C-3' and αAmy10-C-3', respectively. $^{32}$P-UTP (Amersham, SP-6 tested) was used to label the probe.

Figure 2:
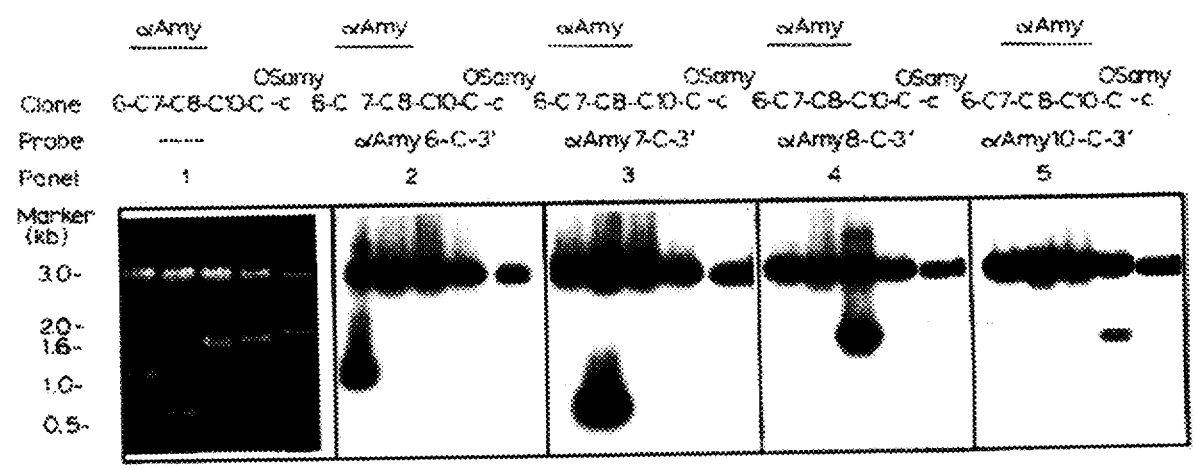
FIG. 2 shows the Southern blot analysis demonstrating specificity of the α-amylase gene-specific probes.
Figure 3:
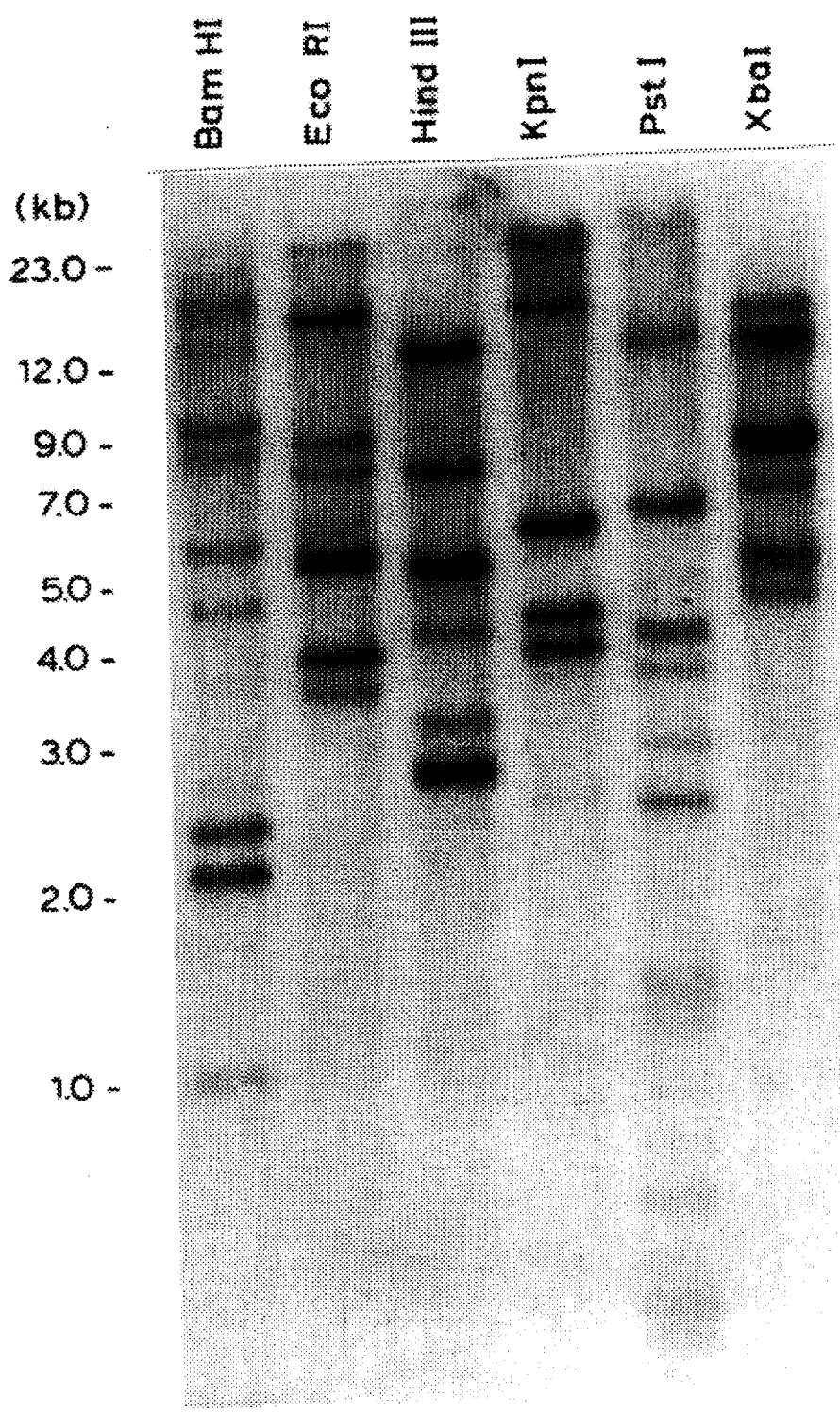
FIG. 3. shows the southern blot analysis of α-amylase genes in rice genome.

Southern blot analysis which demonstrates the specificity of the α-amylase gene-specific probes was carried out as shown in FIG. 2, in which: Panel 1: the α-amylase cDNA was digested with EcoR I and OSamy-c was digested with BamH I and EcoR I, then electrophoresised on 1% agarose gel, and stained with ethidium bromide. Panels 2–5: four replicates of the same gel as shown in Panel 1 were blotted to GeneScreen membranes, hybridized with the 32P-labeled gene-specific probes at 42° C. for 12 hr. After hybridization, the membranes were washed in 0.1 X SSC and 0.1% SDS at 55° C. for 40 min. The vectors were also hybridized because the antisense RNA probes contained a sketch of 62 bp sequences of the multiple cloning sites of pBluescript between the T3 promoter and EcoR I site where the cDNAs were inserted. Molecular weight markers are shown on the left.

c) Southern blot analysis of α-amylase genes in rice genome was carried out as followes:

With referrence to FIG. 3, total rice genomic DNA was isolated from two month old greenhouse-grown plants. Rice leaves were ground in liquid $N_2$ to fine powder, extracted with urea extraction buffer [42 g/ml urea, 5M NaCl, 1M Tris-Cl (pH 8.0), 0.5M EDTA (pH 8.0), and 20% sarkosine] and equal volumes of phenol-chloroform at room temperature for 15 min. After centrifugation, ammonium acetate (pH 5.2) and isopropanol were added to the supernatant. DNA precipitated immediately and was spooled with a glass hook, rinsed in 75% and 100% ethanol, and air-dried. DNA was resuspended in TE buffer and stored at 4° C. Ten micrograms of genomic DNA was digested with six restriction enzymes, fractionated by electrophoresis using 0.8% agarose gels, and transferred to GeneScreen membrane (DuPont). The membrane was probed with the $^{32}$P-labeled 1.5 kb α-amylase cDNA insert of αAmy10-C. Molecular weight markers are shown on the left.

d) Accumulation of α-amylase mRNA in germinating seeds and suspension cultured cells of rice.

Figure 4A:
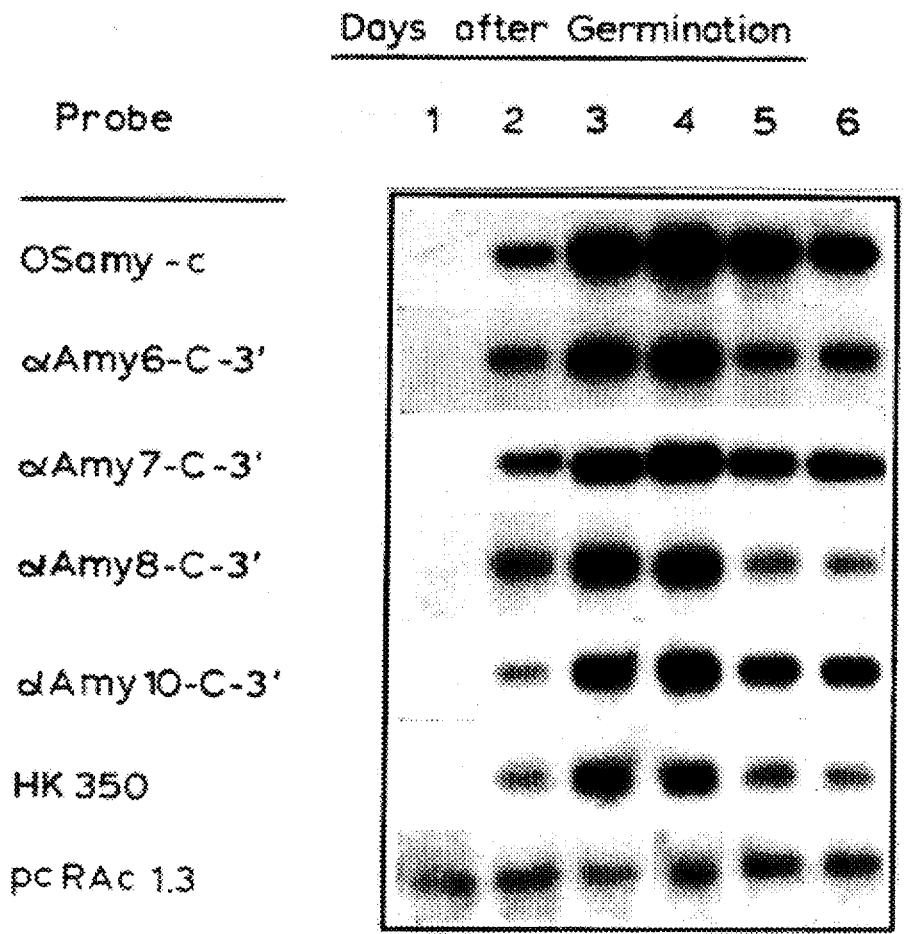
FIGS. 4A and 4B show the accumulation of α-amylase mRNA in germinating seeds and suspension cultured cells of rice. (4A) Time course of accumulation of α-amylase mRNA in $GA_3$-treated aleurone cells of rice. (4B) Relative mRNA levels of the α-amylase genes in the suspension cultured cells of rice during later growth stage.
Figure 4B:
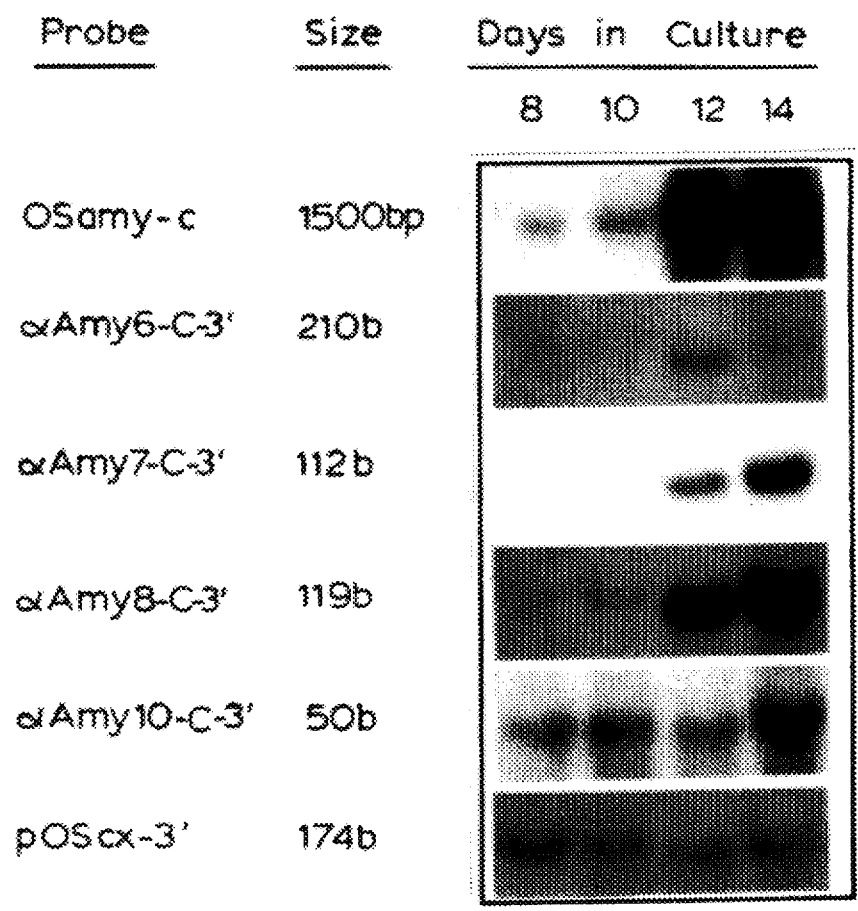

With referrence to FIGS. 4A and 4B, rice seeds were germinated in 10 μM $GA_3$ for different lengths of time. The germinating embryos were cut off and total aleurone RNA was purified from the embryoless seeds according to the method of Belanger, F. C., et al. (Proc. Natl. Acad. Sci. USA, 83: 1354–1358, 1986). Rice suspension cells were cultured as described previously (Yu, S. M., et al (1991), J. Biol. Chem., 266: 21131–21137). RNA was purified from cells grown in the sucrose-containing medium for 8, 10, 12 and 14 days. Five micrograms of total RNA was applied to each lane. The RNA blot analysis was performed according to the method of Thomas P. S. (Methods Enzymol., 100: 255–266, 1983). The plasmid pOSamy-c containing an entire α-amylase coding region in pBluescript was originally subcloned from a rice genomic clone OSamy-c (J. K. Kim and R. Wu (1992), Plant Mol. Biol., 18: 399–402). The 1.5 kb α-amylase DNA insert of OSamy-c was excised from the plasmid vector by restriction enzymes BamH I and EcoR I, gel-purified as described by Maniatis et al. (*Molecular Cloning: A Laboratory Mannual*, pressed by Cold Spring Harbor Laboratory, 1982), and labeled with [α-$^{32}$P]dCTP using the random primer method (A. P. Feinberg and B. Vogelstein (1983), Anal. Biochem., 132: 6–13). The gene-specific probes corresponding to each of the four rice α-amylase cDNAs were prepared and labeled as described above with referrence to FIGS. 1A and 1B and FIG. 2. Size of mRNA detected by all of the probes is 1.6 kb.

e) Binding of aleurone protein extract to the 5' specific DNA fragments of a rice α-amylase gene, in which methods for preparation of aleurone layer extract and DNA mobility-shift (gel retardation) assay were as described previously (Yu., S. M., et al (1990), supra).

Figure 5A:
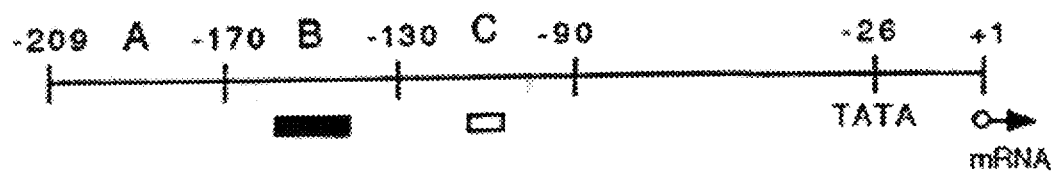
Figure 5B:
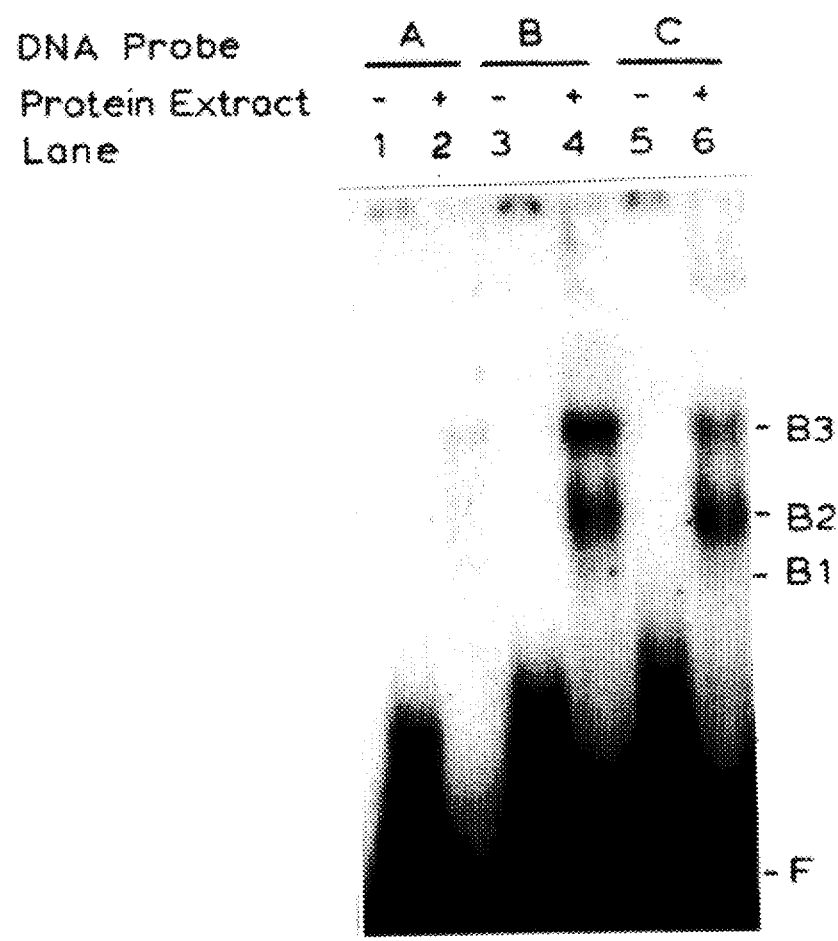

The results were shown in FIGS. 5A, 5B, and 5C, in which:

(5A) Fragments A, B and C were three consecutive 40 bp synthetic DNA fragments at the 5' end of HS501. Filled box indicates the position of two imperfect directly-repeated pyrimidine boxes and a GARE-like element. Open box indicates the position of the 11 bp putative enhancer like element.

(5B) Interaction of aleurone proteins to fragments A, B, and C. The symbols (+) and (−) indicate reactions with or without protein extract, respectively. B1, B2, and B3 indicate positions of the three protein-DNA complexes. F indicates position of the free DNA probe.

(5C) The nucleotide sequences of fragments A, B, and C. Numbers indicate positions of the three fragments relative to the transcription start site. Underlines indicate positions of the pyrimidine boxes. Asterisks (*) indicate position of the GARE-like element. Dash line indicates position of the enhancer-like element.

Results:

(A) Cloning and characterization of the rice cDNA

The rice cDNA library was screened with the α-amylase gene OSamy-c (J. K. Kim and R. Wu (1992), Plant Mol. Biol., 18: 399–402) as the probe. Four of the α-amylase cDNA clones showing different restriction patterns were chosen for subcloning into the plasmid vector pBluescript. The resultant clones were designated as αAmy6-C (*Oryzae sativa* α-amylase cDNA), αAmy7-C, αAmy8-C and αAmy10-C with insert sizes of 0.6, 1.0, 1.4, and 1.5 Kb, respectively. The 3' end regions of these cDNA clones were further subcloned and sequenced (FIGS. 1A and 1B). The sequenced 3' regions of αAmy6-C, αAmy7-C and αAmy8-C are found identical to those of the reported rice α-amylase genes RAmy3B (Sutliff, T. D., et al (1991), Plant Mol. Biol., 16: 579–591), RAmy1A (Huang, N., et al (1990a) Plant Mol. Biol., 14: 655–668), and RAmy3E (Huang, N., et al (1990b), Nucl. Acids Res., 18: 7007–7014), respectively. The genomic DNA corresponding to αAmy10-C has not yet been reported. The DNA and deduced amino acid sequence of genomic rice α-amylase genes corresponding to αAmy6-C, αAmy7-C, αAmy8-C and αAmy10-C are respectively set out in detail in SEQ. ID. NO's.: 1 and 2, 3 and 4, and 5 and 6, respectively. The DNA sequence of αAmy10-C is set out in SEQ. ID. NO:7, in which αAmy10-C was sequenced once only.

B) Construction of the rice α-amylase gene-specific probes

Comparison of nucleotide sequences of the 3' untranslated regions shows very low identity (23–27%) among the four α-amylase cDNA clones (FIGS. 1A and 1B), except αAmy7-C and αAmy10-C which showed 69% identity. Restriction sites were selected for separation of the nonhomologous (gene-specific) regions from the homologous regions of these four cDNA clones and for the preparation of antisense RNA probes. The restriction enzymes used and the nucleotide sequences of the gene-specific regions are shown in FIGS. 1A and 1B.

The gene-specific sequences corresponding to each of the four cDNAs are designated as αAmy6-C-3', αAmy7-C-3', αAmy8-C-3' and αAmy10-C-3'. Appropriate regions were selected for αAmy10-C-3' in which there is very low homology with αAmy7-C-3'. Cross-hybridizations were then performed to determine the gene-specificity and the results showed that each probe only hybridized to its respective parental cDNA (FIG. 2). None of these gene-specific probes hybridized to OSamy-c, which was originally used as the probe to screen the cDNA library. The results demonstrated that the four gene-specific probes are able to discriminate different α-amylase genes.

(C) The rice α-amylases are encoded by a gene family

Identification of the four distinct α-amylase cDNAs indicates that the rice α-amylases are encoded by a gene family. To determine the number of α-amylase genes in rice, total genomic DNA isolated from rice leaves was digested with various restriction enzymes and probed with the entire αAmy10-C sequences at low stringency (FIG. 3). Eight or nine restriction fragments were observed when total DNA was digested with EcoR I. The result generally is in agreement with the reported restriction maps of the rice α-amylase genes (Huang, N., et al (1990a), supra). Since two α-amylase genes were shown to be linked on one EcoR I fragment (Huang, N., et al (1990b), supra), the entire rice genome is estimated to contain at least 10 genes. Parallel genomic DNA blots were also hybridized with the four rice α-amylase gene-specific probes. Each gene-specific probe hybridized specifically to only one restriction fragment (data not shown) further confirming that each probe is derived from one α-amylase gene.

(D) Expression of α-amylase genes in rice germinating seeds

To determine whether the expression of different members of a α-amylase gene family are regulated in a same manner during seed germination, gene-specific probes were used to study the expression of individual α-amylase genes in GA$_3$-treated germinating seeds. The accumulation of α-amylase mRNA in aleurones as a function of time after GA$_3$ addition was determined by RNA blot analysis (FIG. 4A). Probe made from pOSamy-c containing the coding region of a rice α-amylase gene was expected to hybridize to mRNAs of most, if not all, α-amylase genes. The α-amylase mRNA was barely detectable at day 1, rapidly accumulated and reached their maximal levels at day 4, then rapidly turned over between day 4 and day 5. A rice actin cDNA clone, pcRAc1.3 (McElroy, D., et al (1990), Plant Mol. Biol., 14: 163–171), whose expression was not affected by GA$_3$ was used as an internal control.

Level of mRNA showm in FIG. 4A was quantified by measuring the signal intensity of the autoradiogram using a densitometer. The relative mRNA accumulation of each α-amylase gene at each day was determined by comparison of mRNA levels with their peak level at day 4 (Table 1). The mRNA of each α-amylase gene accumulated at a similar rate, except that of αAmy8-C, which almost reached peak level at day 3. However, the mRNAs of αAmy6-C and αAmy8-C were turned over at higher (2-fold) rates than those of αAmy7-C and αAmy10-C. The mRNA levels of αAmy7-C and αAmy10-C were reduced to ½, in contrast, those of αAmy6-C and αAmy8-C were reduced to ¼, of their highest levels at day 5. Afterward all the mRNA levels were reduced at similar low rates. The results show that expression of the four α-amylase geens in germinating seeds are temporally coordinated but quantitively distinct.

(E) Expression of α-amylase genes in cultured suspension cells of rice

Previously, we have shown that the expression of α-amylase genes in cultured suspension cells of rice is induced by the deprivation of carbohydrate nutrient (Yu, S. M., et al (1991), supra). In that report, OSamy-c was used as a probe to study the expression of the entire α-amylase gene family in suspension-cultured cells. Here, gene-specific probes were used to determine the expression pattern of different α-amylase genes. We have shown that the sugars (analyzed by the anthrone reaction) in the sucrose-containing medium were depleted to almost undetectable levels at day 12. A concomitant increase in α-amylase mRNA was observed at day 12 (Yu, S.M., et al (1991), supra). Therefore, RNA's purified from cells grown in the sucrose-containing medium for 8, 10, 12, and 14 days were used for the RNA blot analysis (FIG. 4B). A cDNA clone, pOScx, which was randomly chosen from the same cDNA library, and whose expression was not affected by sugar depletion, was used as an internal control.

Level of mRNA shown in FIG. 4B was also quantified and the relative mRNA accumulation of each α-amylase gene at each day was determined by comparison of mRNA levels with their basal level at day 8 (Table 2). Expression of αAmy7-C and αAmy8-C was induced 6- and 37-fold, respectively, at day 12 and continued to increase at day 14. Expression of αAmy10-C was induced later with a 5-fold increase at day 14. Expression of αAmy6-C also increase 4-fold at day 12, however, it decreased to basal level at day 14. Expression of another α-amylase gene, αAmy3-C, was increased 5-fold after sugar starvation (Yu, S. M., unpublished result). Therefore, among the five α-amylase genes examined so far, αAmy8-C is the most abundantly expressed gene after sugar depletion.

In addition, it is worthwhile noting that αAmy8-C is one of the major genes whose transcripts constitute the 40-fold increase of total α-amylase transcripts as detected with probe of OSamy-c. The results show that expression of the four α-amylase genes in response to carbohydrate starvation in the cultured cells is temporally and quantitatively regulated.

(F) Specific regions of the promoter of a rice α-amylase gene interacting with protein factors in the GA-treated aleurone layer HS501 is a DNA fragment which is located at the 5' end promoter region of a rice α-amylase gene, OSAmy-b (Ou-Lee, T. M., et al. (1988), supra), and its DNA sequences have been presented (Yu, S. M., et al. (1990), supra). Nucleotide sequence of HS501 was later found identical to that of RAmy3C which encodes a complete rice α-amylase isozyme (Sutliff, T. D., et al. (1991), supra). DNA sequence of HS501 includes 260 nucleotides of the 5' non-coding region, and 270 nucleotides in the first and part of the second exons. HK350 is a 3' end-deleted derivative of HS501 and contains the entire 5' non-coding (260 bp) and the first exon regions (90 bp) of HS501. RNA blot analysis showed that α-amylase mRNA of aleurone cells, detected by probing with HK350, was also increased after GA$_3$ treatment (FIG. 4A).

Previously, we have shown that the 5' end of HS501 is important for stable formation of a protein-DNA complex (Ou-Lee, T. M., et al. (1988), supra; Yu, S. M., et al. (1990), supra). To more precisely localize the protein binding sites in HS501, we synthesized three consecutive double-stranded 40 bp oligonucleotides, designated as A, B and C, corresponding to the 5' end of HS501 (FIG. 5A). Proteins were extracted from the aleurone tissues of $GA_3$-treated germinating seeds and interactions between aleurone proteins and the synthetic DNA fragments were detected by the gel retardation assay (FIG. 5B). Interaction of the extract with fragments B and C resulted in the formation of complexes B1, B2 and B3 (FIG. 5B, lanes 4 and 6). Very weak, if any, binding could be detected between the protein extract and fragment A (FIG. 5B, lane 2). Comparison of DNA fragments A, B and C reveals that the three fragments shared some similarity (FIG. 5C). It is not clear whether the weak binding of fragment A to the proteins was due to low affinity or non-specific binding. Nevertheless, the result indicates that there are protein binding sites within fragments B and C.

(G) $GA_3$-dependent and sequence-specific protein factors which bind to HS501

Figure 6:
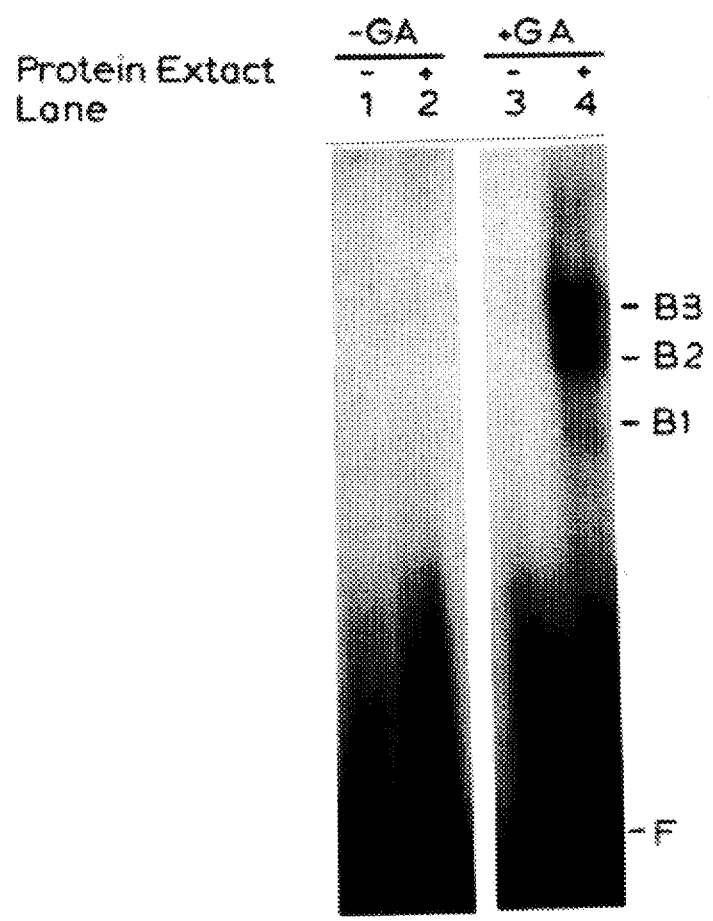
FIG. 6 shows the Binding of the $GA_3$-inducible aleurone proteins to the specific DNA fragment of HS501. +GA and −GA: protein extracts prepared from de-embryoed rice seeds after 3 days of imbibition with or without $GA_3$, respectively.

We carried out another protein/DNA binding assay to determine whether or not the DNA-binding protein is $GA_3$-inducible. Proteins were extracted from the aleurone tissues of de-embryoed seeds which had been treated either with or without $GA_3$ for three days. Only the aleurone extract from $GA_3$-treated seeds gave rise to three complexes using fragment B (FIG. 6, lane 4) or C (data not shown). The aleurone extract did not bind to fragment A (data not shown). No DNA/protein interaction was detected between the aleurone extract from seeds untreated with $GA_3$ and fragment B (FIG. 6, lane 2). The results indicate that the aleurone proteins which bind to fragments B and C are $GA_3$ dependent.

Conclusions:

(1) The availability of gene-specific probes corresponding to each of the four α-amylase cDNAs has enabled us to examine the abundance of mRNA encoding specific α-amylase isozymes. Expression of the individual α-amylase gene was found to be coordinately regulated and their mRNAs were accumulated at similar rates and levels in the aleurone layer of germinating seeds of rice. However, differences in the turnover rates of mRNA of different a-amylase genes indicate a possible differential regulation on the expression of different α-amylase genes in germinating seeds. The four α-amylase genes expressed in germinating seeds were expressed constitutively at low levels in cultured cells when sugars were still present in medium. Expression of three of the four α-amylase genes were induced after sugars are depleted from the medium, and only αAmy6-C displays a different expression pattern from the other three genes. It is not known whether different α-amylase isozymes perform different functions in the starch hydrolysis in rice, or whether the regulatory machinery is differentially acting on a set of α-amylase genes which have similar structures and/or functions. Further investigations on the regulation and expression of different members of the α-amylase gene family in different tissues, and their structural and functional relationships, should help us to better understand the physiological roles of α-amylases in rice.

(2) $GA_3$ and sugars regulate expression of the same α-amylase genes. Whether the two modes of regulation operate through an identical or different molecular mechanism is not known. As expression of αAmy8-C was $GA_3$ regulated in germinating seeds and is one of the major metabolite-regulated genes in suspension-cultured cells, it would be a good model gene for such studies. Molecular mechanisms underlying the two different modes of regulation and interactions between them will be the focus for further studies.

(3) Aleurone tissues contain proteins that interact with fragments B and C of HS501 only in the presence of $GA_3$. Fragment C contains an 11 bp fragment (GTTGCGTTTCT) from positions -108 to -118 which is similar to the animal core enhancer

(Gillies, S. D., et al., Cell (1983), 33: 717–728; Weiher, H., et al (1983) Science, 219: 629–631). Fragment B contains two pyrimidine boxes

from positions -145 to -152 and positions -157 to -164 which are similar to the consensus sequences

found in several α-amylase genes of rice, wheat, barley and other GA-inducible genes such as β-glucanase, carboxypeptidase and aleurain (Huang, N., et al (1990a), supra). Promoter deletion analysis demonstrated that sequences encompassing two of the three pyrimidine boxes in the promoter region of a wheat α-amylase gene, αAmy2/54, are required for high level expression and $GA_3$ regulation of this gene (A. K. Huttly and D. C. Baulcombe (1989), supra). Mutation of the pyrimidine box in the promoter region of a barley α-amylase gene, Amy32b, significantly decrease both the absolute level of expression and the effect of $GA_3$ on expression (Lanahan, M. V., et al (1992), Plant Cell, 4: 203–211). In addition, sequence immediately 3' to the second pyrimidine box in fragment B of HS501, reads TAAATGAG from positions -138 to -145, sharing conservation with the putative GARE element TAACAGAG (Huang, N., et al (1990a), supra; Lanahan, M. V., et al (1992), supra) which is shown to mediate hormonal regulation of the α-amylase gene (Lanahan, M. V., et al (1992), supra; Skriver, K., et al (1991), supra). Whether or not the GA-responsive proteins, the pyrimidine boxes, and the putative GARE element represent the trans- and cis-regulatory elements responsible for GA stimulation of the rice α-amylase genes remain to be determined.

EXAMPLE II

In this experiment, the αAmy8 gene was selected from the foregoing four α-amylase genes for further studying the construction of a chimeric gene containing GUS/NPTII, the expression of which was under the control of the promoter region of said αAmy8 gene, and nopaline synthase gene (NOS), respectively.

A) Materials and Methods:

1) Plant materials:

The rice variety used for transformation was Oryzae sativa L. cv. Tainung 62. At 10–12 days post-anthesis, seeds were dehulled, sterilized with 1% NaOCl and 1 drop of Tween-20 for 90 min., and washed extensively with sterile distilled water. Immature embryos were excised aseptically in a lamina flow bench. Excised embryos were placed on N6RD medium (Chan, M. T., et al (1992), supra) containing N6 salts (Chu, C. C., et al, Scientia Sinica 18: 659–668, 1975), N6 vitamins, 3% sucrose, 0.8% agarose (w/v), 2 µg/12,4-D, and cultured at 25° C. for 16 hours under light (1000 lux). Two days later, the immature embryos were inoculated with Agrobacterium.

Figure 7:
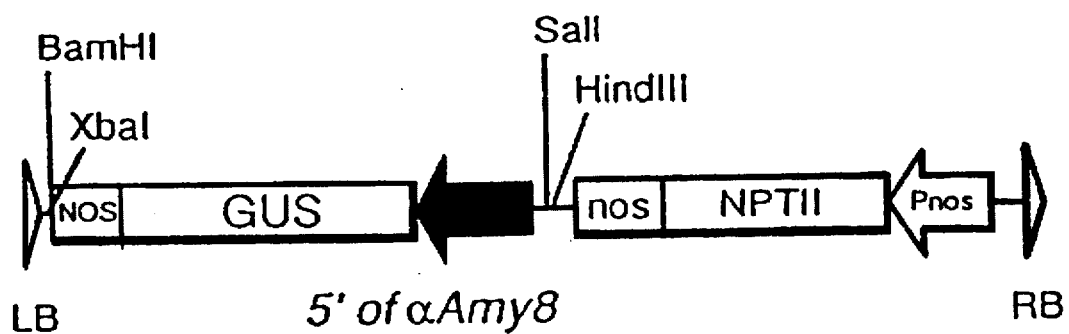
FIG. 7 shows the structure of the binary vector pAG8 containing the αAmy8 (1.2 kb)/GUS chimeric gene. The 1.2 kb 5'-upstream fragment of the α-amylase gene αAmy8 was joined to the coding region of the E. coli β-glucuronidase gene (GUS) with the polyadenylation signals of nopaline synthase gene (NOS). This chimeric gene was inserted between the left border and the selectable marker gene of pBIN19. Abbreviations: RB and LB, right- and left-border of T-DNA, respectively; NPTII, neomycin phosphotransferase II gene; Pnos, promoter of NOS gene.

2) Bacterial strain and plasmid:

An isolated 1.2 kb fragment, just upstream of the coding region of a rice α-amylase gene αAmy8, was joined to the E. coli β-glucuronidase (GUS) (Jefferson, R. A., Plant Mol. Biol. Rptr., 5: 387–405, 1987) with a nopaline synthase (NOS) gene terminator to test the promoter's activity. This chimeric gene [αAmy8 (1.2 kb)/GUS] was inserted between restriction sites Xba I and Sal I of multicloning regions of the binary vector plasmid pBIN19 (Bevan, M. W., Nucl. Acids Res., 12: 8711–8721, 1984) to generate a new plasmid pAG8 (FIG. 7). Plasmid pAG8 was transfected into Agrobacterium tumefaciens strain A281 (Hood, E. F., Bio/technology 2: 702–709, 1984) using the freeze-thaw method (Holster, M., et al (1978), Mol. Gen. Genet., 163: 181–187). Agrobacterium tumefaciens was grown overnight at 28° C. in YEB medium (Zaenen, J., J. Mo. Biol., 86: 109–127, 1974) containing 100 mg/l kanamycin.

B) Transformation:

Twenty-five immature embryos were wounded by sterilized forceps and scalpels and co-cultivated overnight with 25 µl of overnight Agrobacterium culture in a petri dish containing 10 ml of potato suspension culture (PSC), then incubated at 26° C. in the dark for 3 days. For the control, 10 ml of fresh potato suspension culture medium (Chang, H. H., (1991), supra) without addition of potato suspension cells was used. Conditions for potato suspension culture have been described previously (Chang, H. H., (1991), supra).

The infected immature embryos were washed once with potato suspension culture medium containing 500 µg/ml cefotaxime to kill the Agrobacterium and then transferred to N6RF medium containing N6 salts, N6 vitamins, 42.5 µg/ml 4-fluorophenoxyacetic acid (4-FPA), 3% sucrose, 0.8% (w/v) agarose, 40 µg/ml G-418, and 500 µg/ml cefotaxime. The pH of the medium was adjusted to 5.7 before autoclaving. The embryos were cultured at 25° C. for 16 hours under light (2000 lux) and subcultured at weekly intervals.

C) Selection and regeneration of transformants:

Calli were formed from the cultured embryos 3 weeks after Agrobacterium inoculation. The calli were transferred to N6RFB medium (similar to N6RF but containing 13 µg/ml 4-FPA, 1 µg/ml 6-benzylamino-purine (6-BAP), 40 µg/ml G-418 and 200 mg/ml cefotaxime) for selection of transformants. After selection for 3 weeks, calli were transferred to N6 medium for shoot regeneration and root development. Regenerated plants were eventually transferred to pot soil in the greenhouse and grown to self-pollination. Segregation of the kanamycin resistant phenotype in the progeny was analysed by germinating the R1 seeds on MS medium containing 300 µg/ml kanamycin.

D) DNA isolation and analysis of gene incorporation

DNA from transgenic plants was isolated according to the CTAB method (M. G. Murry and W. F. Thompson, Nucl. Acids Res., 8: 4321–4325, 1980). DNA bolt analysis was performed as described by Maniatis et al (Molecular Cloning: A Laboratory Mannual, pressed by Cold Spring Harbor Laboratory, 1982). The probe for GUS was made from the BamH I-Sst I restriction fragment of the pBI221 plasmid (Clontech, Palo Alto, Calif.). The DNA probe was labeled with [α$^{32}$P]dCTP using the random primer method (A. P. Feinberg and B. Vogelstein, Anal. Biochem., 132: 6–13, 1983).

To demonstrate the absence of any Agrobacterium contamination in the transformed plants, the same nylon filters hybridized with GUS DNA were stripped and rehybridized with the probe made from the Hind III 18 and Hind III 27 DNA fragment containing the vir B and vir D regions of pTiC58 (Depicker, A., et al (1980), Plasmid, 47: 193–211; Janssens, A., et al (1986), Plant Sci., 47: 185–193).

E) Assay for neomycin phosphotransferase II (NPTII) activity

The NPTII activity in the putatively transformed calli and plants was assayed in at least four replicates using a modification of a method described by Radke, S. E., et al (Theor. Appl. Genet., 75: 685–694, 1988). Leaf tissue (100 mg fresh weight) was ground in a 1.5 ml Eppendorf tube with an equal volume (100 µl) of extraction buffer (2.5 mM Tris (pH 6.8), 0.143 mM β-mercaptoethanol, 0.27 mM leupeptin), and centrifuged for 15 min. at 4° C. Thirty µg protein were mixed with 10 ml of reaction buffer A (67 mM Tris-maleate, 42 mM MgCl$_2$, 400 mM NH$_4$Cl, 1.7 mM dithiothreitol, and 0.4 mg/ml kanamycin sulfate) or reaction buffer B (identical to reaction buffer A but without kanamycin).

Five µl of ATP solution (1.0 uCi [Γ-$^{32}$P]ATP and 0.75 mM ATP in reaction buffer B) was added. The samples were incubated in a 30° C. water bath for 30 min., then blotted onto three layers of Whatman P81 ion exchange paper placed on top of one piece of Whatman 3 MM paper using a "Hybri-Dot" blotting apparatus (BRL). All the ion exchange papers were washed twice with distilled water for a total of 4 min. and incubated in a 10 ml solution containing 1 mg/ml) proteinase K and 1% SDS at 65° C. for 60 min. The papers were then washed once with distilled water at room temperature for 4 min. and three times with distilled water at 85° C. for 4 min. The 3 pieces of paper were air-dried, stacked in their original positions, and exposed to X-ray film (Kodak) with an intensifying screen.

F) Assay of β-glucuronidase (GUS) activity

To measure GUS activity in the putatively transformed calli and plants, at least two replicates of each sample were assayed according to R. A. Jefferson's method ("Analysis of gene organization and expression in plants," In: Plant Genetic Transformation and Gene Expression, A Laboratory Manaul, Blackwell Scientific Publications, Oxford, Draper, J., et al (eds) pp. 263–339, 1988). Samples were homogenized with GUS extraction buffer (50 nM sodium phosphate (pH 7.0), 10 mM EDTA, 10mM Triton X-100, 0.1% sarkosyl, and 10 mM β-mercaptoethanol). Twenty µg protein with an equal volume of SDS sample buffer (62.5% mM Tris-HCl, 0.23% SDS, 10% glycerol, 50 mM 5-mercaptoethanol, and 0.001% bromophenol blue) were incubated at room temperature for 15 min. Electrophoresis was run overnight at room temperature at 3 V/cm.

The gel was washed with 100 ml of GUS extraction buffer four times within 2 hours, incubated with GUS fluorometric buffer (1 mM methyl umbelliferylglucuronide in GUS extrac-tion buffer) on ice for 30 min., and incubated at 37° C. in the dark for 30 min. The reaction was stopped with 0.2 M Na$_2$CO$_3$. The gel was illuminated by a 365 nm UV lamp with a Kodak 2E Wratten filter and photographed.

Localization of GUS expression in the transformed plants was evaluated by 5-bromo-4-chloro-3-indolyl glucuronide (X-gluc) histochemical assay (Benfey, P. N., et al (1989), EMBO J., 8: 2195–2202). Sections of leaf blade, sheath, stem or root of nontransformed or transformed 4-month-old plants were cut with a Vibratome (Oxford) sectioning device. Sections of 100 to 200 microns were incubated in a solution containing 1 mM X-gluc, 10 mM EDTA, 100 nM $NaH_2PO_4.H_2O$ (pH 7.0), and 0.1% Triton X-100 at 37° C. for 12 to 17 hrs. After staining, sections were rinsed in 70% ethanol for 5 min and chlorophyll in the sections was cleared by incubation for 10 min. in a solution of 5% formaldehyde, 5% acetic acid and 20% ethanol, followed by incubation for 2 min. in 50% ethanol, 2 min. in 100% ethanol, and two washings in distilled water. The sections were examined under a microscope. GUS activity in the R1 progeny was assayed by staining.

The R1 seeds were first germinated in MS medium containing 2 µg/ml 2,4-D and 300 µg/ml kanamycin to induce callus formation. Calli were formed from the germinating seeds after 1 week. A portion of each callus was removed and subjected to a modified GUS histochemical staining assay (Benfey, P. N., et al (1989), supra). Briefly, calli of the R1 progeny or control were incubated at 37° C. for 12 to 17 hrs. in a solution containing 1 mM X-gluc, 10 mM EDTA, 100 mM $NaH_2PO_4.H_2O$ (pH 7.0), and 0.1% Triton X-100. Photographs were taken with a Kodacolor 64 film under a dissecting Microscope (Olympus).

G) PCR

Two sequences in the GUS coding region were chosen to amplify a 410 bp fragment within the gene: The 5' primer (ACGTCCTGTAGAAACCCCAA) and the 3' primer (AGTTCAGTTCGTTGTTCACACA) located in the GUS coding region 3 bp and 417 bp downstream of the translation initiation site (ATG), respectively. One hundred µg of pAG8 were used as positive control; 100 ng of total rice DNA from young leaves of the R1 progeny were used. PCR was carried out in a 50 µl solution containing 50 mM KCl, 10 mM Tris-HCl, 15 mM $MgCl_2$, 0.1% gelatin (w/v), 1% Triton X-100, 0.2 mM of each deoxynucleoside triphosphate (dATP, dCTP, dGTP, dTTP), 2.5 units of Taq DNA polymerase (Promega), and 0.25 mM of each primer.

The sample was preheated at 94° C. for 5 min. and subjected to PCR amplification for 27 cycles. Cycling was controlled by a programmable thermal cycler (MJ Research, Inc.) programmed with the following conditions: denaturation, 94° C. for 1 min.; annealing, 58° C. for 2 min.; extension, 72° C. for 3 min. The sample was then incubated at 58° C. for 2 min. and 72° C. for 10 min. Five µl of the PCR product was electrophoresed in a 1% agarose gel and detected by staining with ethidium bromide. Southern blots of PCR products were hybridized with a probe made from the BamH I-Sst I GUS restriction fragment.

Results:

A) Transformation of immature rice embryos by *Agrobacterium tumefaciens*

Figure 8A:
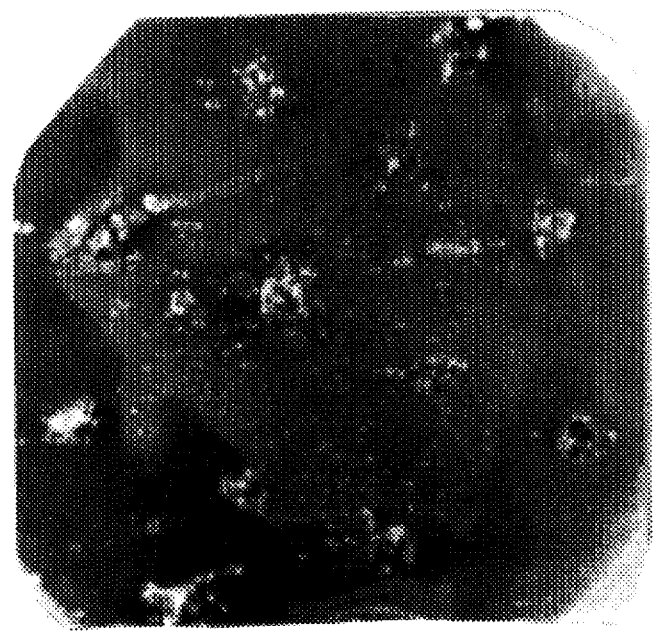
FIGS. 8A, 8B, 8C, 8D, 8E, and 8F show the selection and regeneration of a transgenic rice plant. (8A) Nontransformed control calli on the selective medium (N6RF) containing 40 μg/ml G418 three weeks after plating; (8B) Regeneration of shoot and roots from G418-resistant calli 8 weeks after inoculation with Agrobacterium; (8C) Transgenic plant grown on N6/G418 medium 9 weeks after inoculation; (8D) The transgenic plant grown in pot soil in greenhouse 16 weeks after inoculation; (8E) Tillering of the transgenic plant 18 weeks after inoculation; (8F) Seed-setting of the transgenic plant 24 weeks after inoculation.

Previously, we have shown that transformation of rice using Agrobacterium can be improved by the addition of PSC (Chan, M. T., et al (1992), supra). Here, presence of PSC with the Agrobacterium inoculum increased the transformation efficiency almost 3-fold (Table 3). Approximately 6.8% of immature rice embryos inoculated with Agrobacterium formed calli and proliferated on selective medium. The uninoculated or inoculated but non-transformed immature embryos turned brown and died within 3 weeks (FIG. 8A).

Figure 8B:
Figure 8C:
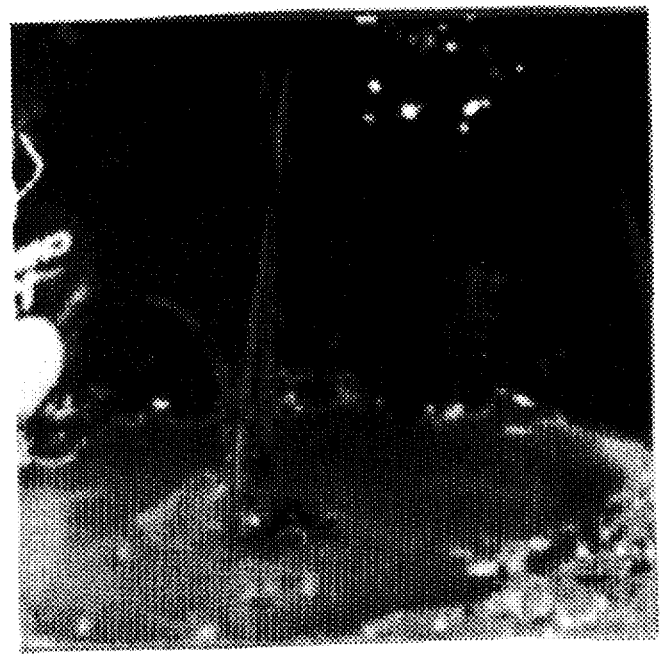

After culture of calli, shoots developed rapidly and roots formed spontaneously after 4 weeks (FIG. 8B). Among the 250 immature embryos inoculated, 17 calli and 4 plants were recovered from culture. The four transgenic plants were designated T1, T2, T3 and T4. These plants were ready to be transplanted into soil after 9 weeks of culture (FIG. 8C).

Figure 8D:
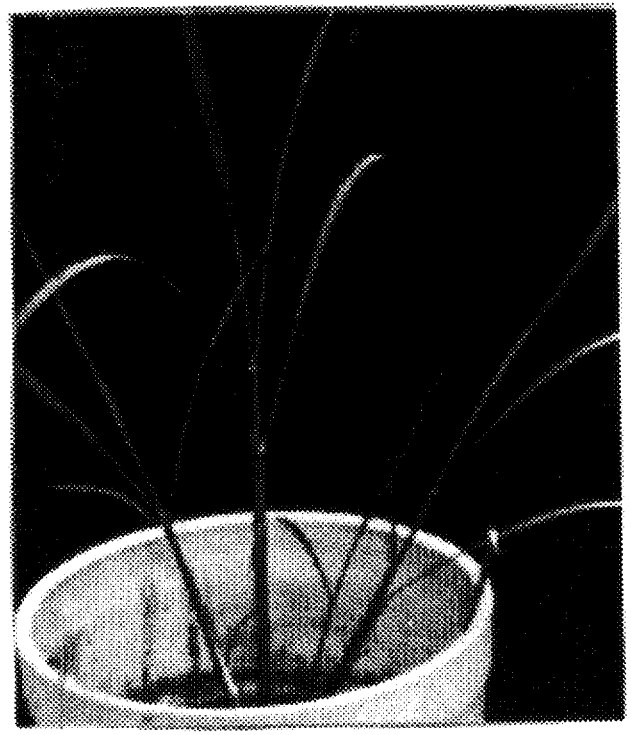
Figure 8E:
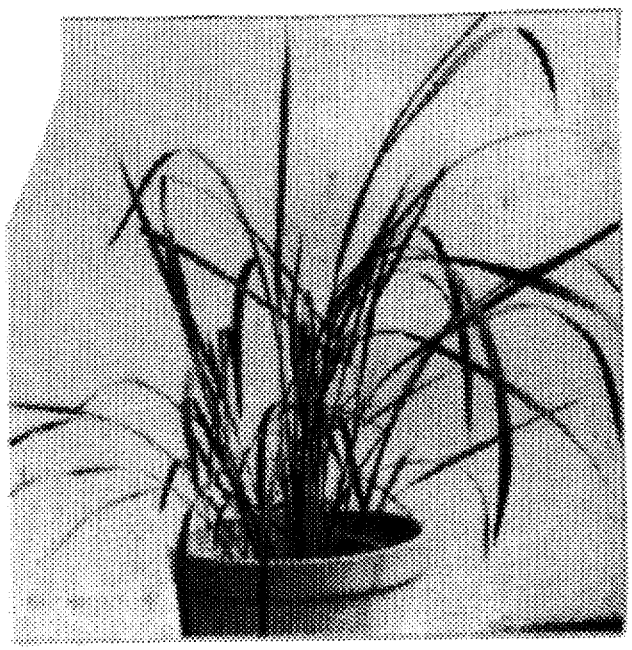
Figure 8F:

Only one plant, T1, survived to flower and produce progeny (FIGS. 8D–8F). This transgenic plant exhibited normal phenotype and was fertile, except that it grew more slowly (about 14 weeks from being a 121 cm long plant to flowering) and produced less seeds (total 75 seeds) than a wild type plant. The other three transgenic plants were also transplanted into soil but did not survive.

B) DNA analysis of transformants

Figure 9:
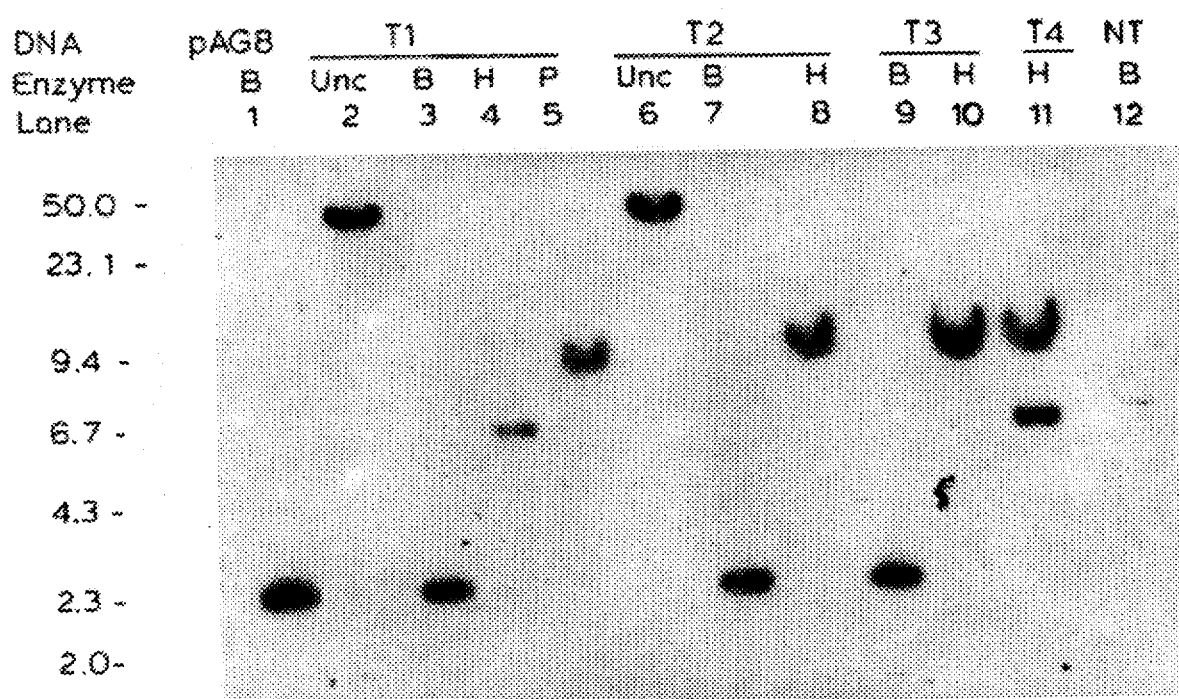
FIG. 9 shows a DNA blot analysis for detection of GUS gene in the transgenic rice plants. Genomic DNA was isolated from young leaves of wild type and transgenic plants. Five μg of DNA digested with various restriction enzymes were loaded on each lane. The Sst I/BamH I fragment containing GUS gene in pBI221 was used as the probe. Lane 1:pAG8 digested with BamH I; Lanes 2 to 5: DNA from transgenic plant T1; Lanes 6 to 8: DNA from transgenic plant T2; Lanes 9 to 10: DNA from transgenic plant T3; Lane 11: DNA from transgenic plant T4; and Lane 12: DNA from a non-transformed control plant. Abbreviations of restriction enzymes: B, BamH I; H, Hind III; P, Pst I; Unc, undigested.

To provide physical evidence for the integration of foreign DNA into the genome, Southern blot analysis of restriction digests of genomic DNA from leaves of the 4 transgenic plants (T1, T2, T3 and T4) was performed using the GUS DNA from pBI221 as a probe (FIG. 9). The size of the undigested rice genomic DNA (Unc) was about 50 kb (FIG. 9, lanes 2 and 6). After digestion with BamHI (B), GUS DNA was detected as a fragment of the expected size 2.3 kb (FIG. 9, lanes 3, 7 and 9), the same size as that present in pAG8 (FIG. 9, lane 1). After digestion with Hind III (H) or Pst I (P), the 50 kb band disappeared and the lower molecular weight DNA fragments appeared (FIG. 9, lanes 4, 5, 8, 10 and 11).

Transgenic plant T4 appeared to have two integration sites for the GUS gene as two hybridization bands were detected when DNA was digested with Hind III (FIG. 9, lane 11). Since the GUS DNA probe only hybridized to DNA from the 4 transgenic plants but not to the non-transformed control plant (NT) (FIG. 9, lane 12), this indicates that the GUS gene was integrated into the rice genome.

To prove that the GUS DNA detected in FIG. 9 did not result from contamination with Agrobacterium in the transgenic plants, the same nylon filter was reprobed with vir B and vir D DNA. As the vir genes are not located on the Ti-plasmid, Southern blot analysis using vir DNA as a probe should provide a reliable way to detect Agrobacterium contamination. The Agrobacterium strain A281 used in this experiment was derived from strain C58 which carries pTiC58. A probe made from the Hind III 18 and Hind III 27 DNA fragments containing the vir B and vir D regions of pTiC58 should thus hybridize to DNA of Agrobacterium. However, no hybridization band was observed when using the vir DNA as a probe (data not shown), clearly demonstrating that the GUS DNA detected in the genome of the transgenic plants was not due to persisting Agrobacterium cells in the rice tissues.

C) Expression of GUS and NPTII in the transgenic calli and plants

The GUS coding sequence in pAG8 was placed downstream of the putative 5' promoter region of an α-amylase gene (αAmy8) so as to make a transcriptional fusion. To investigate the promoter function of the 1.2 kb long 5' region of this α-amylase gene, expression of the GUS gene was determined by the presence of GUS activity in the transgenic calli and plants.

Figure 10A:
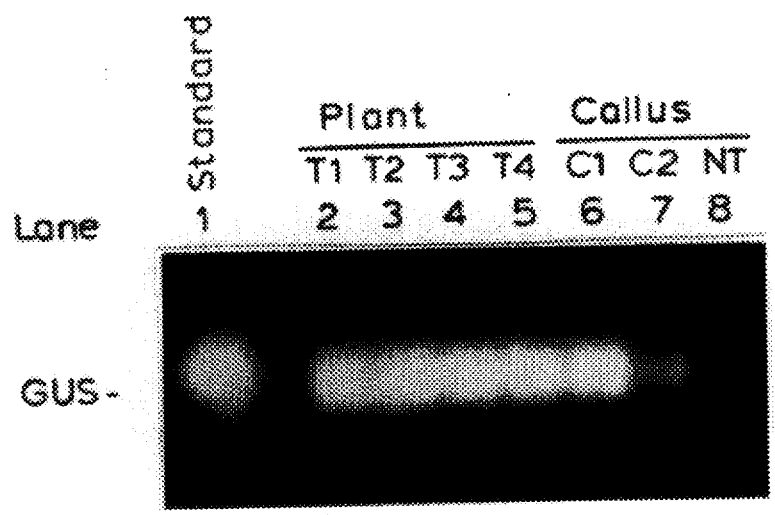
FIGS. 10A and 10B show the analysis of GUS and NPTII activities in the transgenic calli and plants. (10A) Analysis of GUS activity in transgenic rice. Protein extracts from transformed and non-transformed rice plants and calli were separated using 7.5% SDS-PAGE. The gel was reacted with 1 mM methyl umbelliferyl glucuronide (MUG) and photographed as described in "Materials and methods." Lane 1: standard E. coli β-glucuronidase; Lanes 2–5: protein extract from transformed plants; Lanes 6–7: protein extract from transformed calli; Lane 8: protein extract from non-transformed callus. Twenty μg per lane of protein was loaded in lanes 2 to 8. (10B) Analysis of neomycin phosphotransferase II activity in transgenic rice. Thirty μg protein extracts from transformed or non-transformed rice plants and calli were reacted with $[\Gamma-^{32}P]$-ATP, dot blotted on Whatman P81 papers and autoradiographed as described in "Materials and methods." Row A: reactions with kanamycin; Row B: reactions without kanamycin; Lanes 1–3: protein extracts from transgenic plants; Lanes 5–6: protein extracts from transformed calli; Lane 4 and 7: protein extracts from non-transformed plants and callus, respectively.

GUS present in the cell extracts migrated in an SDS-polyacrylamide gel with an apparent molecular weight of 69 kDa (FIG. 10A). The levels of GUS activity that could be detected in the four transgenic plants and callus C1 were similar (FIG. 10A, lanes 2–6). The lower level of GUS activity in transgenic callus C2 (FIG. 10A, lane 7) seems to be coupled with its lower level of NPTII activity (FIG. 10B, lane 6. No GUS activity was detected in the non-transformed callus (NT) (FIG. 10A, lane 8). The results suggest that the 1.2 kb 5' region of αAmy8 contains an efficient promoter for regulating GUS gene expression.

Figure 10B:
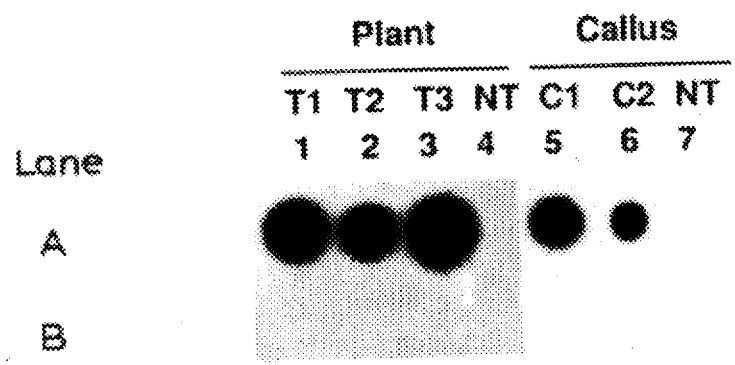

Plasmid pAG8 contains the NPTII coding region driven by the nopaline synthase promoter. Consequently, selection for plants carrying foreign genes should be achieved using media containing G418. The NPTII activity was further determined in 8 randomly chosen transformed calli (R0) and 3 transgenic plants (T1, T2, and T3). All of the 8 transgenic calli expressed NPTII activity and data for 2 of them (C1 and C2) are presented (FIG. 10B, lanes 5 and 6). NPTII activity was also detected in the 3 transgenic plants (FIG. 10B, lanes 1, 2, and 3). No activity was observed in the non-transformed callus (FIG. 10B, lane 7) and plant (FIG. 10B, lane 4).

D) Histochemical localization of GUS in transgenic rice plant

Figure 11A:
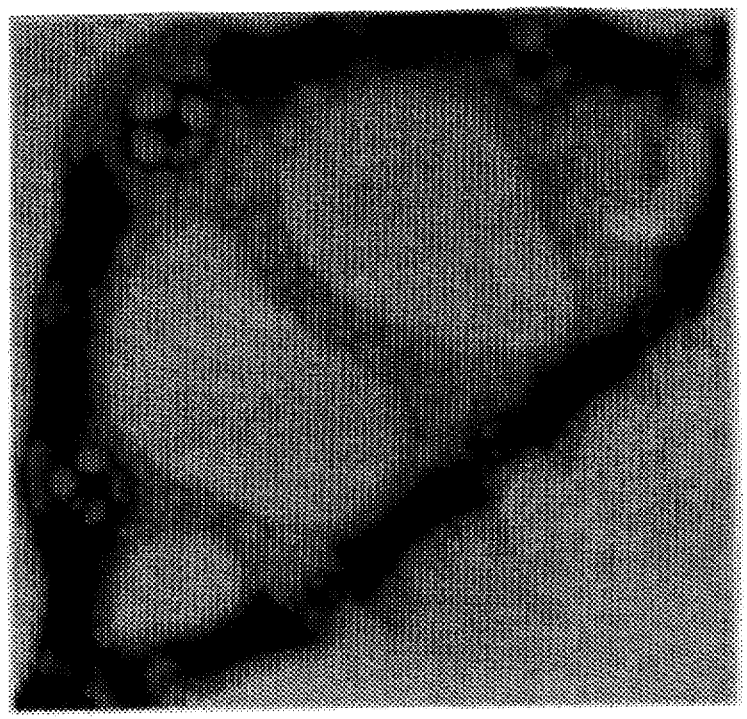
FIGS. 11A–11J. Expression of the αAmy8 (1.2 kb)/GUS gene in various tissues of transgenic rice plant T1. Thin sections of each organ from transformed or non-transformed plants of 100 cm in height were stained with X-gluc as described in Materials and methods. (11A) Cross section of a leaf blade from a non-transformed plant; (11B) Cross section of a leaf blade from transgenic plant T1; (11C) Higher magnification of the boxed area in (11B); (11D) Cross section of stem of one of the tillers from a non-transformed plant; (11E) Cross section of stem of one the tillers from transgenic plant T1; (11F) Higher magnification of the boxed area in (11E); (11G) Cross section of a leaf sheath from transgenic plant T1; (11H) Cross section of young leaves embedded inside the leaf sheaths of one of the tillers from transgenic plant T1; (11I) Cross section of a root of transgenic plant T1; (11J) Unsectioned root hair from transgenic plant T1. Abbreviations: ph, phloem; mx, metaxylem tracheary element; sc, sclerenchyma; par, parenchyma.
Figure 11B:
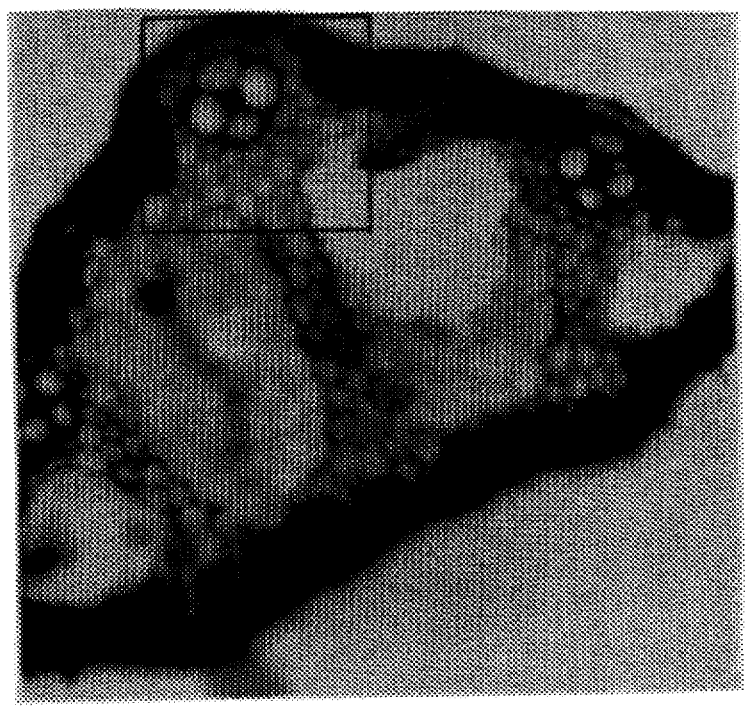
Figure 11C:
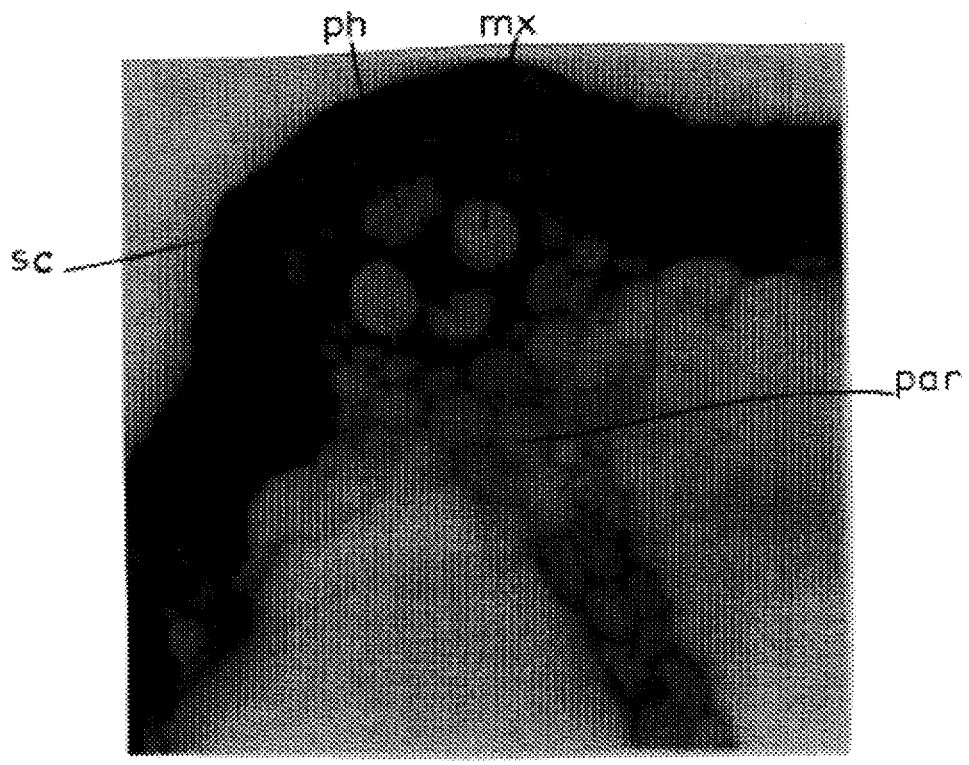
Figure 11D:
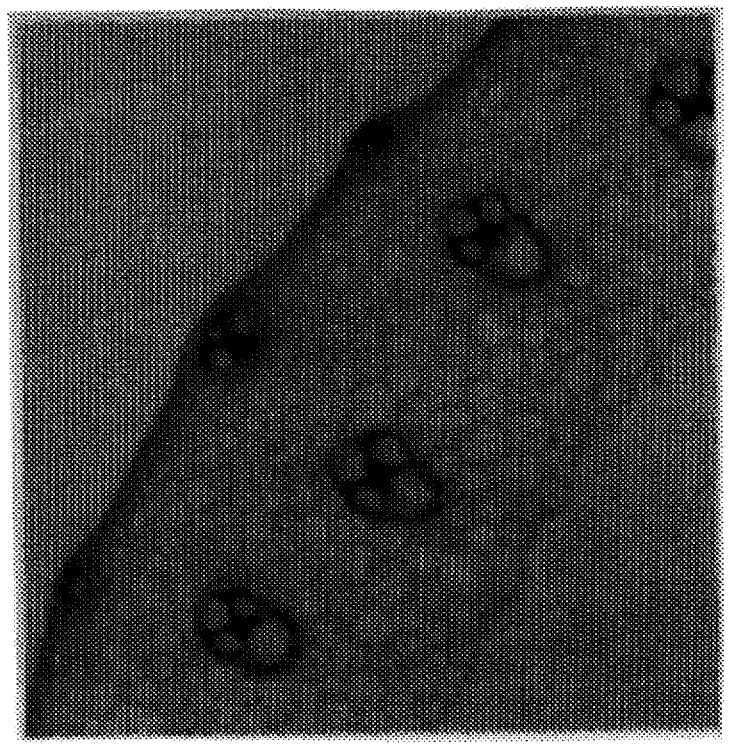
Figure 11E:
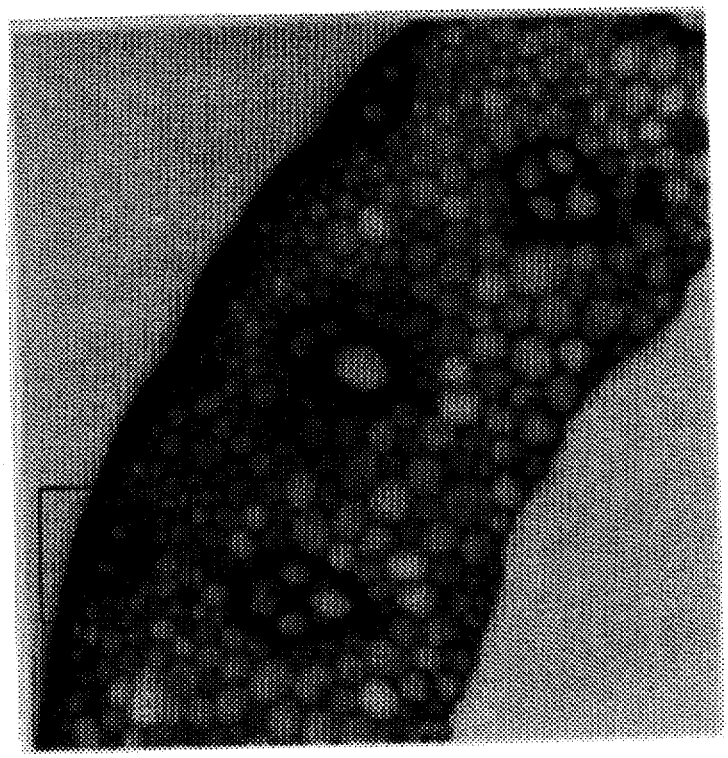
Figure 11F:
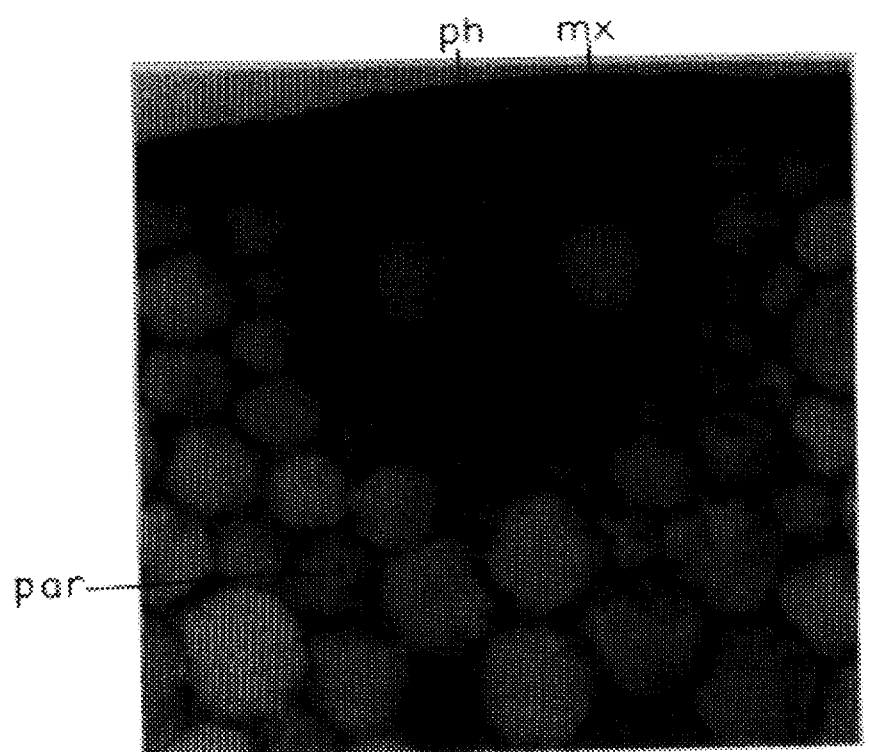
Figure 11G:
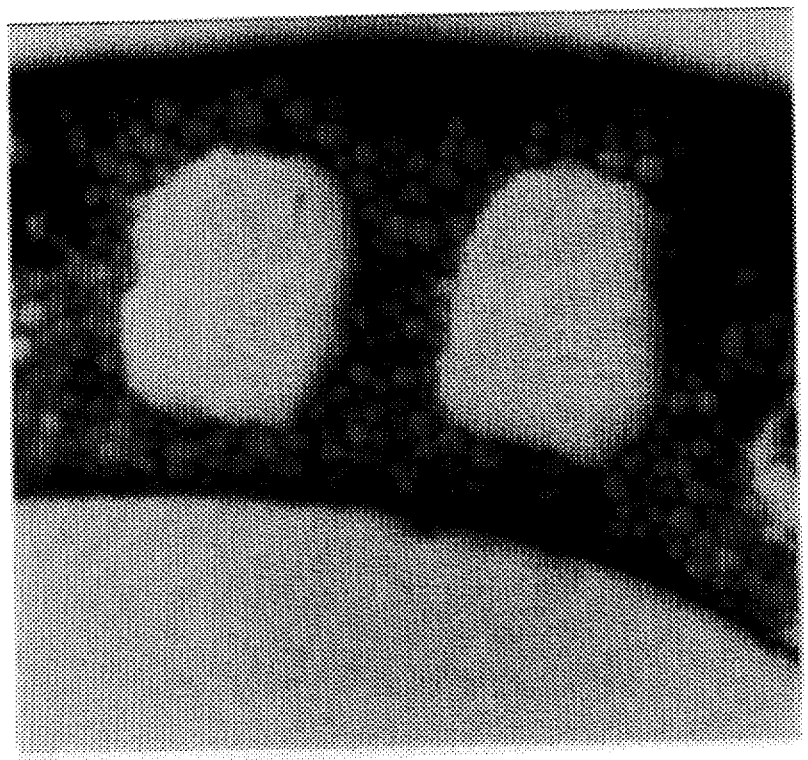
Figure 11H:
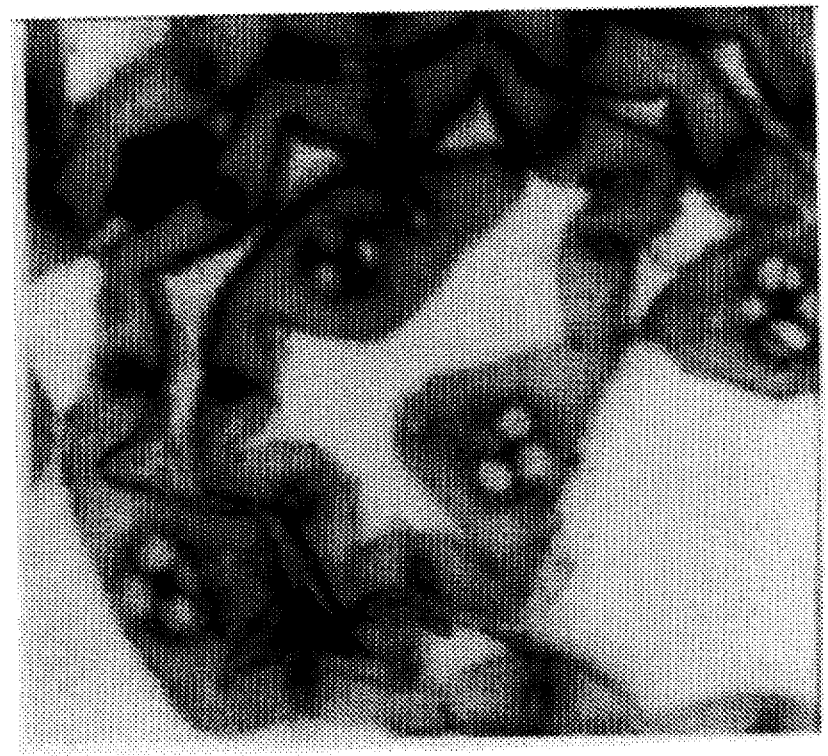
Figure 11:
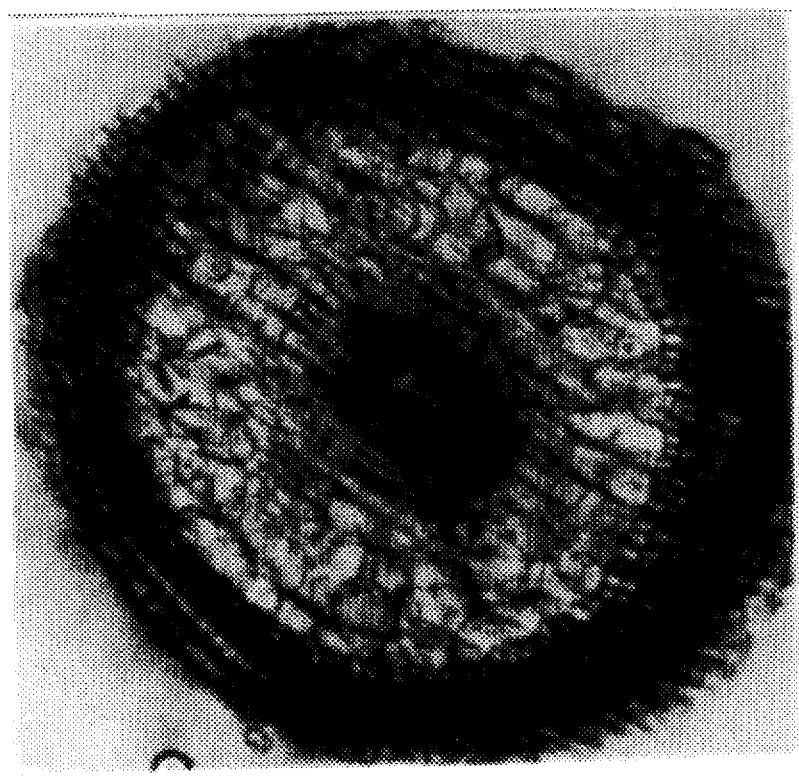
Figure 11J:
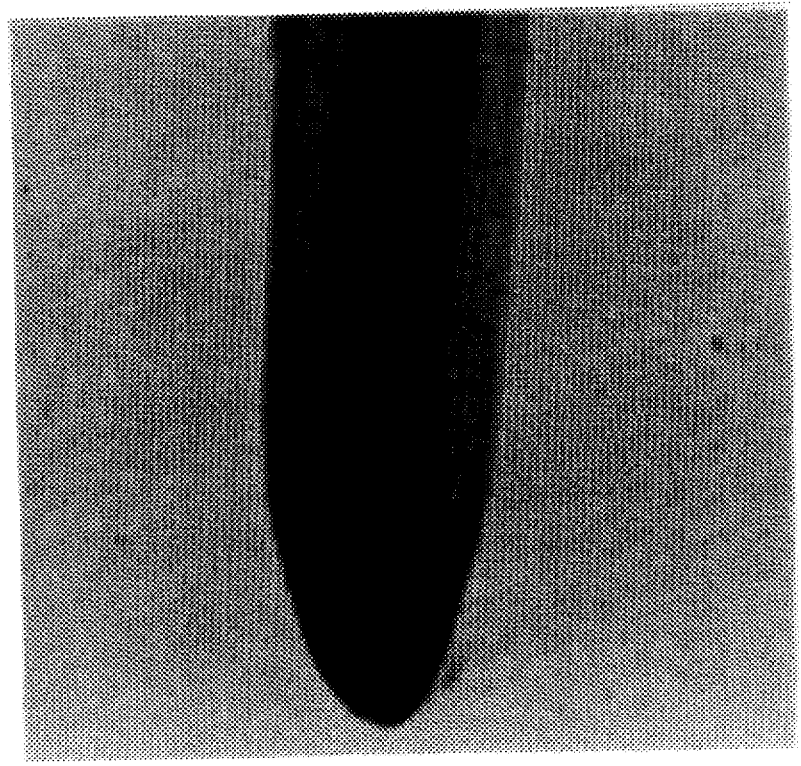

To localize the cellular expression pattern of the GUS gene driven by the 5' region of αAmy8, various tissues of the transgenic plant (T1) were sectioned and subjected to histochemical staining (FIGS. 11A–11J). Blue staining of sections appeared 17 hr after incubation in the substrate. GUS expression was observed in all cell types of leaf blade (FIGS. 11B, 11C), stem (FIGS. 11E, 11F), and sheath (FIG. 11G). Tissue sections of leaf blade and stem from non-transformed control plants displayed no staining (FIGS. 11A, 11D). Transverse sections of root revealed that the epidermal cells were stained blue and the cortex cells were stained lightly (FIG. 11I). Unsectioned root hairs showed intense staining in the vascular cylinder and light staining in the cortex cells (FIG. 11J). No GUS expression was found in the sections of very young leaf blades which were embedded inside sheaths (FIG. 11H).

E) Analysis of R1 progeny

Of the 75 seeds harvested from the transgenic plant T1, 36 seeds were germinated on selective media (containing 300 μg/ml kanamycin) to induce callus formation. Within 10 days, 32 germinating seeds formed calli and continued to grow and were identified as resistant. The other 4 germinating seeds also formed calli, but turned brown and died later. About half of each kanamycin resistant callus was removed and assayed for GUS activity.

Figure 12:
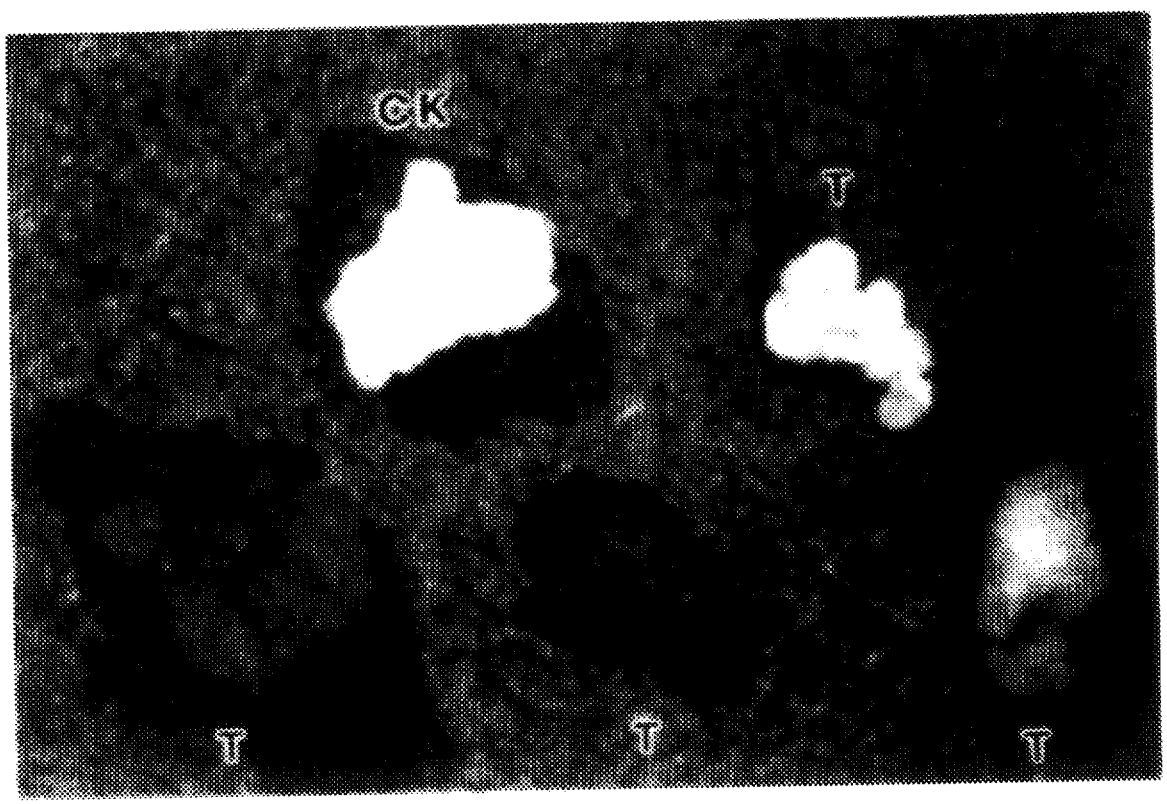
FIG. 12 shows the analysis of GUS activity in R1 seeds of transgenic plant T1. The seeds were germinated in MS medium containing kanamycin and 2,4-D to induce callus formation. The calli were subjected to GUS histochemical staining assay as described in "Materials and methods." CK: callus derived from a seed of non-transformed plant; T: calli derived from seeds of transgenic plant T1.

Of the 32 calli assayed, 28 showed blue staining and 4 calli remained yellow, similar to the non-transformed control (data for 4 of them are presented in FIG. 12). Calli derived from different transgenic R1 seeds showed considerable variation in GUS activity, as revealed by different degrees of blue staining (FIG. 12).

Figure 13A:
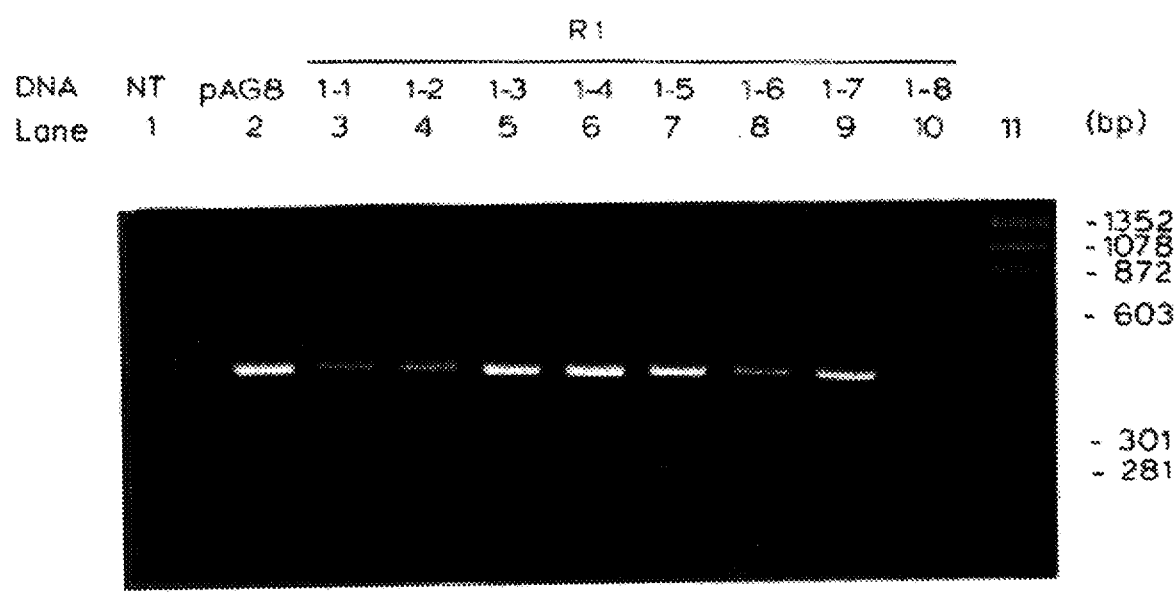
FIGS. 13A and 13B show the PCR amplification of a 410 bp GUS DNA fragment from R1 progeny of transgenic rice plant T1. DNA was isolated from young leaves of R1 progeny of transgenic plant T1. PCR was performed as described in "Materials and methods." (13A) Amplified DNAs were electrophoresed in 1% agarose gel and detected by ethidium bromide staining. (13B) Same DNAs as in (13A) were blotted on Gene Screen membrane (Du Pont, Wilmington, Del.), hybridized with a $^{32}P$-labeled GUS DNA probe, and autoradiographed. Lane 1: DNA template from non-transformed plant (NT) was used as a negative control.
Figure 13B:
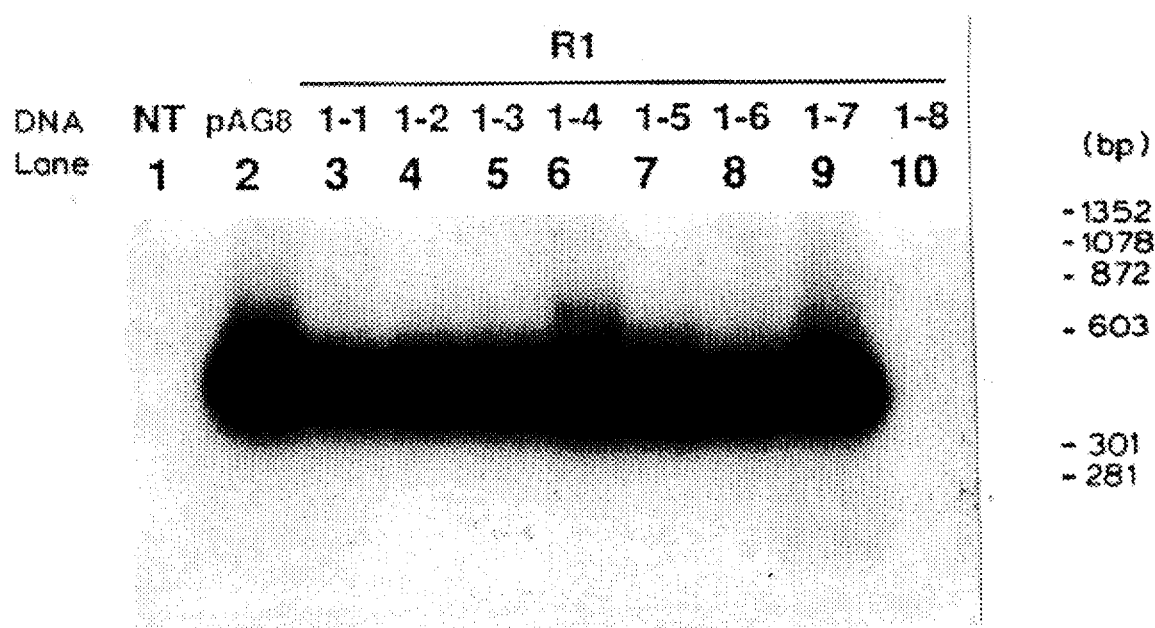

Among the remaining 39 seeds of T1, 18 seeds were germinated and grown in a greenhouse. DNA was isolated from young leaves of 13 of these R1 plants when they were 10 cm tall. The DNA was subjected to PCR amplification of a 410 bp fragment within the GUS coding region (FIG. 13A). Identification of the amplified DNA was established by blot hybridization to a $^{32}$P-labeled GUS DNA probe (FIG. 13B). These results further confirmed the presence of GUS genes in the R1 progeny of the original transformant.

Discussion:

Although several methods for the transformation of rice using protoplasts or suspension cells are available at present, attempts to regenerate mature plants from the transformed protoplasts or suspension cells of many rice varieties have been unsuccessful. Methods based on the use of the soil bacterium *Agrobacterium tumefaciens* are still preferred in many instances, as Agrobacterium-mediated transformation does not require protoplasts and, in general, results in higher transformation efficiency and a more predictable pattern of foreign DNA integration than other transformation techniques (Czernilofsky, A. P., et al (1986), DNA, 5: 101–113). Here we show that transgenic rice plants are successfully produced using an Agrobacterium-mediated DNA transfer system.

Two factors may have contributed to the success in rice transformation and regeneration. The first factor is the addition of PSC during the co-cultivation of Agrobacterium with the immature rice embryos. PSC probably contains substances which enhance the Agrobacterium-mediated T-DNA transfer process, since PSC induced the formation of calli one week earlier and enhanced the frequency of transformation about 3-fold (Table 3). PSC is rich in acetosyringone and sinapinic acid (Chang, H. H., et al (1991), supra), which are generally believed to enhance transformation of various plant species (Stafer, W., et al (1985), supra). However, the role of these two compounds in the success or efficiency of transformation is not clear at this time. The transformation percentage of 1.6% that we obtained for producing transgenic plants would render the use of Agrobacterium to transfer genes into rice more feasible.

The second factor for successful transformation and regeneration is the use of immature rice embryos (10 to 12 days after pollination) as the transformation materials, since they may contain less inhibitors or more virulence inducers than mature embryos to T-DNA transfer. Immature embryos of maize have also been shown to be competent for Agrobacterium-mediated gene transfer and that competence depends on genotype and developmental stage. Meristematic tissue of the immature embryo becomes competent at developmental stages that correlate with the differentiation of the first one to two leaf initials (M. Schlappi and B. Horn (1992), Plant Cell, 4: 7–16).

Therefore, the immature embryos at some developmental stages may produce conditions which increase the success of T-DNA transfer, such as (a) the availability of *vir* gene-inducing substances, (b) low production of bacteriotoxic substances, (c) favorable endogenous hormone levels, and (d) the availability of receptors for attachment of Agrobacterium (M. Schlappi and B. Horn (1992), supra).

Although only four plants could be regenerated from the transformed calli in this experiment, all these plants were proved to be real transformants. Integration of chimeric genes into the genomes of the four transgenic plants was confirmed by hybridization of the restricted genomic DNA. In addition, our experiments ruled out the possibility of Agrobacterium contamination of the rice tissues as a possible source of the hybridization bands.

Detection of NPTII and GUS activities in the transgenic plants indicates that the integrated foreign genes were expressed. Our results also indicate that kanamycin can be used to select transformed rice cells from a mixed population of transformed and non-transformed cells. To avoid the occurrence of kanamycin escapees, it is important that selection be applied immediately after the co-cultivation.

Of the 4 regenerated transgenic plants, only one plant (T1) survived to flower and produce progeny. Transgenic plant T1 flowered in December, when the room temperature in the greenhouse was below 20° C., but we don't know whether this was one of the reasons for its low yield (75 seeds). The transgenic R1 progeny inherited and expressed the NPTII and GUS genes, as shown by their resistance to kanamycin and expression of GUS activity. A 3:1 ratio was expected in the progeny from self-pollination, assuming that the gene was transmitted as a single dominant locus.

In the GUS staining assay in conjunction with kanamycin selection of calli derived from immature embryos of 32 R1 progeny, 28 were GUS positive and kanamycin resistant, 4 were GUS negative but kanamycin resistant, and 4 were GUS negative and kanamycin sensitive. This 28:8 or 3.5:1 ratio indicates that GUS segregation in the R1 progeny of transgenic plant T1 is consistent with the predicted 3:1 Mendelian inheritance pattern in a heterozygous x heterozygous cross.

The lack of GUS activity in the 4 kanamycin-selected R1 may indicate that the GUS gene was either absent or present but nonfunctional. Absence of the GUS gene in the kanamycin-resistant R1 could be due to deletion of the GUS gene via DNA rearrangement. PCR amplification of GUS DNA fragments was achieved from DNA of 13 out of 18 R1 plants tested. The 13:5 or 2.6:1 ratio is also close to the theoretical Mendelian segregation pattern.

The rice α-amylases are encoded by a multigene family which contains at least ten distinct members (Huang, N. et al (1990), Plant Mol. Biol., 14: 655-668). Genomic and cDNA clones representing different members of the α-amylase gene family have been isolated in our laboratory. Expression of the α-amylase gene, αAmy8, is $GA_3$-regulated in germinating seeds. This gene is also one of the major metabolite-regulated genes in cultured suspension cells of rice (Yu, S. M., et al., unpublished result). In our experiments, the DNA resulting from fusion of the 1.2 kb 5' flanking region of αAmy8 to the reporter gene GUS was transformed into rice. Expression of GUS in the transgenic rice indicates that this 1.2 kb fragment contains a functional promoter.

Thus, use of transgenic rice carrying a reporter gene under the control of an α-amylase promoter has provided a new tool for analyzing the regulatory elements in the α-amylase promoters. Such studies should lead to an understanding of the regulation of α-amylase gene expression in rice.

To our surprise, the histochemical localization of GUS activity indicated that the αAmy8 promoter was functional in all cell types of the mature leaves, stems, sheaths and roots of the transgenic rice plants. The only tissues which did not express GUS were the very young leaves embedded inside the sheaths. GUS was active in cells of the epidermis, mesophyll and vascular bundles of leaves. It was also active in the epidermis, cortex, and vascular cylinder of the roots. Therefore, the expression of αAmy8/GUS is not tissue-specific. Rather, it is temporally regulated in the transgenic plant, though it is not known at which growth stage of leaves αAmy8 begins its expression. Our histochemical studies were performed only with T1, the single transgenic plant that survived after being transferred to soil.

The possibility that αAmy8/GUS was inserted close to a very active enhancer in the rice genome, which could render high-level expression or loss of tissue-specific expression of the foreign gene cannot be ruled out. However, αAmy8 is apparently one of the major metabolite-regulated genes in cultured suspension cells (Yu, S. M., et al. (1992), Gene, inpress) and thus probably plays an important role in the carbohydrate metabolism of the vegetative tissues of rice.

Therefore, it is not totally surprising that the GUS gene driven by αAmy8 promoter is constitutively expressed in every cell type of different tissues of the transgenic plant. If this is also true for the naturally existing α-amylase gene in wild type plants, it would be interesting to know the physiological function of αAmy8 promoter in rice. The general distribution and levels of GUS activity obtained in different tissues of stably transformed rice plants indicate the potential of αAmy8 promoter as a positive control for studies in gene activity in transgenic rice.

In conclusion, this experiment demonstrates that immature rice embryos are susceptible to Agrobacterium-mediated transformation and that the foreign genes transferred are inherited by the next generation of the transformant.

In addition to the rice variety Tainung 62 (Japonica type) used in this experiment, T-DNA has also been successfully transferred into genomes of other rice varieties including Tainan 5 (Japonica type) and Taichung Native no. 1 (Indica type) using the same approach (M. T. Chan, H. H. Chang and S. M. Yu, unpublished result). Therefore, it is proposed that this simple approach can be applied to transform other rice varieties and, with modification, other monocot species.

EXAMPLE III

As noted from the beginning, an objective of the present invention is to provide a new gene expression system functional in plant host cells, thereby rendering the expressed gene product capable of being directly recovered from medium. To achieve this purpose, based upon the results obtained in Example II, further experiments were carried out to investigate the regulation of the promoter region of αAmy8 with respect to the expression of the foreign gene GUS in the present transgenic rice cells.

More specifically, it was studied whether or not the expression of said GUS gene under the control of said promoter will be influenced by a sugar-depleted or sugar-free condition. The following experiments adopted the materials and methods described in Example II.

Immature embryos of rice were transformed with *Agrobacterium tumefaciens* which carried the αAmy8/GUS chimeric gene (pAGS). Calli derived from the transformed embryos were then grown in liquid MS medium containing 2 μM 2,4-D to establish a suspension culture of rice. The cell cultures were subcloned every 5 days. For this experiment, suspension cells were transferred to medium with (+) or without (−) sucrose for two days. RNA was purified from the treated cells and the GUS mRNA was detected by Northern blot analysis using $^{32}$P-labeled GUS DNA as probe. 10 μg of total RNA was loaded in each lane. The results are shown in FIG. 14. To detect whether the expressed GUS protein was maintained in the transformed cells or secreted into the culture medium, rice suspension cells were grown and treated under conditions identical to the above experiment. Proteins were extracted from the treated cells or collected from the medium, subjected to Western blot analysis and detected with the GUS antibody. 20 μg of total proteins were loaded in each lane. The results are shown in FIG. 15.

Results and Discussions:

Referring to FIG. 14, NT indicates the non-transformed cells; C3, C7 and C11 are three independent transformed cell lines. The C11 cell line was deposited in the Fermentation Research Institute Agency of Industrial Science and Technology (FERM), Japan on Nov. 4, 1992, with the accession number of FERM BP-4064 under the Budapest Treaty. No GUS mRNA was detected in the non-transformed cells, either in the presence or absence of sucrose (lane 1 and 2). GUS mRNA was detected in cells of the three cell lines grown in medium containing sucrose (lanes 3, 5 and 7). The mRNA levels increased in cells grown in sucrose-free medium (lanes 4, 6 and 8).

In FIG. 15, arrow (←) indicates the position of GUS protein. No GUS protein was detected in the non-transformed cells or their culture media, either in the presence or absence of sucrose (lanes 1, 2, 8 and 9). No GUS protein could be detected in the transformed cells or media in the presence of sucrose (lanes 3, 5, 10 and 12), either. As expected, the GUS protein could be easily detected in the transformed cells and media in the absence of sucrose (lanes 4, 6, 11 and 13).

Accordingly, it can be confirmed from the above obtained results that the present gene expression system can achieve at least two main advantages. First, the expression of the αAmy8/GUS chimetic gene is well controlled by the promoter region of αAmy8, especially under the sugar-depleted or sugar-free condition of the culture medium. Hence, the present gene expression system comprising the promoter of an α-amylase gene can promote the quantitative production, under sugar-depleted or sugar-free condition, of a desired gene product, such as the GUS protein exemplified here. Second, inasmuch as the promoter region of said chimetic gene also includes a DNA sequence encoding the signal sequence of α-amylase, the expressed gene product (GUS) will be secreted into the culture medium, rendering said gene product recoverable from the culture medium. As a result, the procedures for recovery and purification of the desired gene product can be simplified, and the contamination therein can also be diminished.

From the above teachings, it is apparent that various modifications and variations can be made without daparting from the spirit and scope of the present invention. It is therefore to be understood that this invention may be practiced otherwise than as specifically described.

TABLE 1

Relative accumulation of α-amylase mRNA in germinating rice seeds as detected by α-amylase gene-specific probes.

| Probes | Days after germination | | | | | |
|---|---|---|---|---|---|---|
| | 1 | 2 | 3 | 4 | 5 | 6 |
| OSamy-c | 0[a] | 25 | 73 | 100 | 67 | 47 |
| αAmy6-C-3' | 0 | 23 | 73 | 100 | 27 | 26 |
| αAmy7-C-3' | 0 | 26 | 72 | 100 | 50 | 48 |
| αAmy8-C-3' | 0 | 31 | 98 | 100 | 27 | 23 |
| αAmy10-C-3' | 0 | 23 | 64 | 100 | 47 | 44 |

[a]Level of α-amylase mRNA was determined by densitometric scanning of the autoradiograms shown in FIG. 6A, and corrected with the mRNA level of pcRAc1.3. The relative mRNA accumulation for each α-amylase gene was then determined by dividing the α-amylase mRNA level of each day by the mRNA level (peak level) of day 4.

TABLE 2

Relative accumulation of α-amylase mRNA in cultured suspension cells of rice at later growth stages as detected by α-amylase gene-specific probes.

| Probes | Days in culture | | | |
|---|---|---|---|---|
| | 8 | 10 | 12 | 14 |
| OSamy-c | 1.0[a] | 3.8 | 39.5 | 38.8 |
| αAmy6-C-3' | 1.0 | 1.3 | 4.1 | 1.2 |
| αAmy7-C-3' | 1.0 | 1.8 | 6.2 | 9.8 |
| αAmy8-C-3' | 1.0 | 2.2 | 37.0 | 44.5 |
| αAmy10-C-3' | 1.0 | 1.3 | 1.2 | 5.0 |

[a]Level of α-amylase mRNA was determined by densitometric scanning of the autoradiograms shown in FIG. 6B, and corrected with the mRNA level of pOScx-3'. The relative mRNA accumulation for each α-amylase gene was then determined by dividing the α-amylase mRNA level of each day by the mRNA level (basal level) of day 8.

TABLE 3

Effect of PSC on the efficiency of rice transformation by Agrobacterium

| Agrobacterium Strains | Addition of PSC | No. of immature embryos inoculated | No. of Transgenic | | Frequency for induction of transgenic | |
|---|---|---|---|---|---|---|
| | | | callus | plant | callus (%) | plants (%) |
| A281 (pAG8) | + | 250 | 17 | 4 | 6.8 | 1.6 |
| A281 (pAG8) | − | 80 | 2 | 0 | 2.5 | 0 |

*PSC = potato suspension culture

What is claimed is:

1. A method for producing a gene product by expressing a gene encoding said gene product in angiosperm host cells, comprising:
   a) constructing a vector expressible in angiosperm host cells, said vector comprising a promoter region derived from an α-amylase gene of a plant, and a gene encoding a desired gene product;
   b) transforming a compatible angiosperm host cell with said vector;
   c) cultivating the resultant transformant host cell;
   d) subjecting said cultivated transformant host cell to a sugar-depleted or sugar-free condition to promote the expression of said gene under the control of said promoter region; and
   e) recovering the expressed gene product.

2. A method according to claim 1, wherein said promoter region is derived from an α-amylase gene of a monocot.

3. A method according to claim 2, wherein said promoter region is derived from an α-amylase gene of a graminaceous monocot.

4. A method according to claim 3, wherein said promoter region is derived from an α-amylase gene of a cereal crop.

5. A method according to claim 4, wherein said promoter region is derived from an α-amylase gene of rice crop.

6. A method according to claim 1, wherein said promoter region derived from the α-amylase gene includes the promoter of the α-amylase gene and a DNA sequence encoding the signal peptide of α-amylase.

7. A method according to claim 5, wherein said promoter region derived from the α-amylase gene includes the promoter of the α-amylase gene and a DNA sequence encoding the signal peptide of the α-amylase.

8. A method according to claim 6, wherein said expressed gene product is recovered from the culture medium of said transformant host cell.

9. A method according to claim 1, wherein said vector further comprises a marker gene, a reporter gene, an antibiotic-resistance gene, an enhancer or a regulatory sequence.

10. A method according to claim 9, wherein said vector comprises an antibiotic-resistance gene.

11. A method according to claim 10, wherein said antibiotic is kanamycin or hygromycin.

12. A method according to claim 9, wherein said vector comprises a reporter gene.

13. A method according to claim 12, wherein said reporter gene is the β-glucuronidase (GUS) gene.

14. A method according to claim 1, wherein the transformation of said compatible angiosperm host cell is enhanced by co-culture with a potato suspension culture.

15. A method according to claim 1, wherein the transfer of said vector to the host cell is carried out by electroporation, polyethylene glycol-mediated transformation, particle bombardment, micro-injection method, ultrasonic method, poly-L ornithine method, calcium phosphate method or Agrobacterium-mediated transformation system.

16. A method according to claim 15, wherein the transfer of said vector to the host cell is carried out by the Agrobacterium-mediated transformation system.

17. A method according to claim 1, wherein said vector further comprises an α-amylase structural gene derived from a plant.

18. A method according to claim 17, wherein said expressed gene product is recovered together with α-amylase or recovered as a fusion protein with the α-amylase.

19. A method according to claim 1, wherein said compatible angiosperm host cell is a rice, barley or wheat suspension cultured cell.

20. A method according to claim 19, wherein said compatible angiosperm host cell is a rice suspension cultured cell.

21. A method of claim 1, wherein said sugar-depleted or sugar free condition is a condition deficient of sucrose, glucose or fructose.

22. A method according to claim 1, wherein said gene product is a protein of animal, plant or microbial origin.

23. A method for producing a gene product by expressing a gene encoding said gene product in angiosperm host cells, comprising:
   a) constructing a vector expressible in angiosperm host cells, said vector comprising a promoter region derived from an α-amylase gene of a plant, and a gene encoding a desired gene product, said promoter region derived from the α-amylase gene including the promoter of the α-amylase gene and a DNA sequence encoding the signal peptide of α-amylase;
   b) transforming a compatible angiosperm host cell with said vector;
   c) cultivating the resultant transformant host cell in a culture medium; and
   d) recovering the expressed gene product from said medium.

24. A method according to claim 23, wherein said promoter region is derived from an α-amylase gene of a monocot.

25. A method according to claim 24, wherein said promoter region is derived from an α-amylase gene of a graminaceous monocot.

26. A method according to claim 25, wherein said promoter region is derived from an α-amylase gene of a cereal crop.

27. A method according to claim 26, wherein said promoter region is derived from an α-amylase gene of rice crop.

28. A method according to claim 23, wherein said vector further comprises a marker gene, a reporter gene, an antibiotic-resistance gene, an enhancer or a regulatory sequence.

29. A method according to claim 28, wherein said vector comprises an antibiotic-resistance gene.

30. A method according to claim 29, wherein said antibiotic is kanamycin or hygromycin.

31. A method according to claim 28, wherein said vector comprises a reporter gene.

32. A method according to claim 31, wherein said reporter gene is the β-glucuronidase (GUS) gene.

33. A method according to claim 23, wherein the transformation of said compatible angiosperm host cell is enhanced by co-culture with a potato suspension culture.

34. A method according to claim 23, wherein the transfer of said vector to the host cell is carried out by electroporation, polyethylene glycol-mediated transformation, particle bombardment, micro-injection method, ultrasonic method, poly-L ornithine method, calcium phosphate method or Agrobacterium-mediated transformation system.

35. A method according to claim 34, wherein the transfer of said vector to the host cell is carried out by the Agrobacterium-mediated transformation system.

36. A method according to claim 23, wherein said vector further comprises an α-amylase structural gene derived from a plant.

37. A method according to claim 36, wherein said expressed gene product is recovered together with α-amylase or recovered as a fusion protein with the α-amylase.

38. A method according to claim 23, wherein said compatible angiosperm host cell is a rice, barley or wheat suspension cultured cell.

39. A method according to claim 38, wherein said compatible angiosperm host cell is a rice suspension cultured cell.

40. A method of claim 23, wherein before the recovery of the expressed gene product, said cultivated transformant host cell is subjected to a sugar-depleted or sugar-free condition to promote the expression of said gene under the control of said promoter region.

41. A method of claim 40, wherein said sugar-depleted or sugar free condition is a condition deficient of sucrose, glucose or fructose.

42. A method according to claim 23, wherein said gene product is a protein of animal, plant or microbial origin.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 2086 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Rice (Oryzae sativa)
      ( B ) STRAIN: CV. M202

( v i i ) IMMEDIATE SOURCE:
      ( A ) LIBRARY: (EMBL) genomic
      ( B ) CLONE: '-Amy6-C ( i x ) FEATURE:
      ( A ) NAME/KEY: CDS
      ( B ) LOCATION: join(481..495, 572..1510, 1610..1891)

( i x ) FEATURE:

(A) NAME/KEY: mat_peptide
(B) LOCATION: join(481..495, 572..1510, 1610..1891)

(x) PUBLICATION INFORMATION:
(A) AUTHORS: Yu et al., Su-May
(B) TITLE: Regulation of '-amylase- encoding gene expression in germinating seeds and cultured cells of rice
(C) JOURNAL: Gene
(D) VOLUME: in press (xi) SEQUENCE DESCRIPTION: SEQ ID NO:1:

```
AAGCTTCTGA AGCTGATGCG ATCAAACCTC AAAAGACCAT GGGCAGCAGC ACGGAAGTTA      60

CAAACCGAAG CCGCGCGGCG CGCATACGCA TCAGAAAGGC GCGCAATAAC GGACCACCCA     120

TACGGCGGCC GCGCTCTGTT CGCGGCGTCC CTGCGCCTGC ATCGCACGCC ATCCAAGGCT     180

GCATAGCACG ACGCATACAT ATCTCACGCG CCCTTTTTAT CTGCTTATAA ATGAGATAGC     240

CCACATAGCA GCGCTGCCGT TTCTCCTCTT CTCTCGTTGG GGGCAACCGA ACTTATCCAA     300

CAACGATCCA TCCATTGGCC AAGTGGCTGC CGTGCTGCAC CTATAAATTC ACATGCACCG     360

GCATGCCACT CCACACAAGT GAGCTACTCG AAAGAAGCAG CA ATG GCA AAG CGC        414
                                                Met Ala Lys Arg
                                                -26 -25
```

| ATA GCC TCA ATG AGC AGC CTC CTC CTT ATC GCC TTG CTC TGT CTG AGC | 462 |
|---|---|
| Ile Ala Ser Met Ser Ser Leu Leu Leu Ile Ala Leu Leu Cys Leu Ser |  |
| -20                    -15                        -10 |  |

| TCT CAC TTG GCC CAA GCC CAG GTC CTC TTC CAG GTAAGCATCC TGTAGTACAA | 515 |
|---|---|
| Ser His Leu Ala Gln Ala Gln Val Leu Phe Gln |  |
| -5                  1                5 |  |

```
TGTCACATTA CATAAAAAAA AATGACTTGC GTTGACATG ACTGTTCTTG GTGTAG         571
```

| GGG TTC AAC TGG GAG TCG TGG AAG AAG CAG GGC GGG TGG TAC AAC TTC | 619 |
|---|---|
| Gly Phe Asn Trp Glu Ser Trp Lys Lys Gln Gly Gly Trp Tyr Asn Phe |  |
|                  10                  15                  20 |  |

| CTC CAT GGC CAC GTC GAC GAC ATC GCC GCG ACC GGT GTC ACG CAC GTC | 667 |
|---|---|
| Leu His Gly His Val Asp Asp Ile Ala Ala Thr Gly Val Thr His Val |  |
|              25                  30                  35 |  |

| TGG CTC CCA CCG CCG TCG CAC TCC GTC GCC CCG CAG GGA TAC ATG CCG | 715 |
|---|---|
| Trp Leu Pro Pro Pro Ser His Ser Val Ala Pro Gln Gly Tyr Met Pro |  |
|              40                  45                  50 |  |

| GGC CGG CTC TAC GAC CTG GAC GCT TCC AAG TAC GGC ACG GGG GCA GAG | 763 |
|---|---|
| Gly Arg Leu Tyr Asp Leu Asp Ala Ser Lys Tyr Gly Thr Gly Ala Glu |  |
|   55                  60                  65 |  |

| CTC AGG TCG CTG ATC GCC GCC TTC CAC AGC AAA GGC ATC AAG TGC GTC | 811 |
|---|---|
| Leu Arg Ser Leu Ile Ala Ala Phe His Ser Lys Gly Ile Lys Cys Val |  |
| 70                  75                  80                  85 |  |

| GCC GAC ATC GTC ATC AAC CAC CGG TGC GCG GAT TAC AAG GAT AGC CGT | 859 |
|---|---|
| Ala Asp Ile Val Ile Asn His Arg Cys Ala Asp Tyr Lys Asp Ser Arg |  |
|                  90                  95                 100 |  |

| GGC ATC TAC TGC ATT TTC GAG GGT GGC ACG CCG GAC AGC CGC CTC GAC | 907 |
|---|---|
| Gly Ile Tyr Cys Ile Phe Glu Gly Gly Thr Pro Asp Ser Arg Leu Asp |  |
|             105                 110                 115 |  |

| TGG GGC CCC GAC ATG ATC TGC AGC GAC GAC ACG CAG TAC TCC AAC GGC | 955 |
|---|---|
| Trp Gly Pro Asp Met Ile Cys Ser Asp Asp Thr Gln Tyr Ser Asn Gly |  |
|             120                 125                 130 |  |

| CGC GGT CAC CGC GAC ACC GGC GCA GAC TTC GGC GCG GCG CCC GAC ATC | 1003 |
|---|---|
| Arg Gly His Arg Asp Thr Gly Ala Asp Phe Gly Ala Ala Pro Asp Ile |  |
|     135                 140                 145 |  |

| GAC CAC CTC AAC ACG CGT GTG CAG ACA GAG CTG TCC GAC TGG CTC AAT | 1051 |
|---|---|
| Asp His Leu Asn Thr Arg Val Gln Thr Glu Leu Ser Asp Trp Leu Asn |  |
| 150                 155                 160                 165 |  |

| TGG CTC AAG TCC GAC GTC GGC TTC GAC GGC TGG CGC CTC GAC TTC GCC | 1099 |
|---|---|
| Trp Leu Lys Ser Asp Val Gly Phe Asp Gly Trp Arg Leu Asp Phe Ala |  |

```
AAG GGA TAC TCG GCG GCC GTC GCC AAG ACG TAC GTC GAC AAC ACC GAC      1147
Lys Gly Tyr Ser Ala Ala Val Ala Lys Thr Tyr Val Asp Asn Thr Asp
            185             190             195

CCG TCC TTC GTC GTC GCC GAG ATA TGG AGC AAC ATG CGT TAC GAC GGC      1195
Pro Ser Phe Val Val Ala Glu Ile Trp Ser Asn Met Arg Tyr Asp Gly
        200             205             210

AAC GGT GAG CCG TCG TGG AAC CAG GAC GGT GAC CGG CAG GAG CTG GTG      1243
Asn Gly Glu Pro Ser Trp Asn Gln Asp Gly Asp Arg Gln Glu Leu Val
215             220             225

AAC TGG GCG CAG GCC GTC GGT GGC CCT GCG TCA GCG TTC GAC TTC ACG      1291
Asn Trp Ala Gln Ala Val Gly Gly Pro Ala Ser Ala Phe Asp Phe Thr
230             235             240             245

ACC AAG GGC GAG CTG CAG GCG GCG GTG CAA GGT GAG CTG TGG CGG ATG      1339
Thr Lys Gly Glu Leu Gln Ala Ala Val Gln Gly Glu Leu Trp Arg Met
            250             255             260

AAG GAC GGC AAC GGC AAG GCG CCG GGG ATG ATT GGC TGG CTG CCA GAG      1387
Lys Asp Gly Asn Gly Lys Ala Pro Gly Met Ile Gly Trp Leu Pro Glu
        265             270             275

AAG GCC GTC ACC TTC ATC GAC AAC CAT GAC ACT GGC TCC ACA CAG AAC      1435
Lys Ala Val Thr Phe Ile Asp Asn His Asp Thr Gly Ser Thr Gln Asn
            280             285             290

TCA TGG CCG TTC CCC TCC GAC AAG GTC ATG CAG GGC TAC GCC TAC ATC      1483
Ser Trp Pro Phe Pro Ser Asp Lys Val Met Gln Gly Tyr Ala Tyr Ile
    295             300             305

CTC ACA CAC CCT GGA GTA CCC TGC ATT GTGAGTCCTC AGCTGCATGA            1530
Leu Thr His Pro Gly Val Pro Cys Ile
310             315

ATACGAATGC CATAAAGAAA AATCTAATTT TCTCAACCAG TTTCTCCGAC TAAATTCTGT    1590

TTATTGACTA TGTGTGCAG TTC TAC GAC CAT GTA TTT GAC TGG AAC CTG AAG     1642
                      Phe Tyr Asp His Val Phe Asp Trp Asn Leu Lys
                                  320             325

CAG GAG ATC AGC ACA TTA GCT GCA GTG AGA TCA AGA AAT GAG ATT CAT      1690
Gln Glu Ile Ser Thr Leu Ala Ala Val Arg Ser Arg Asn Glu Ile His
330             335             340             345

CCC GGG AGC AAG CTG AAA ATC CTT GCT GCT GAG GGA GAC GTC TAT GTC      1738
Pro Gly Ser Lys Leu Lys Ile Leu Ala Ala Glu Gly Asp Val Tyr Val
            350             355             360

GCC ATG ATC GAT GAT AAG GTC ATA ACA AAG ATT GGG ACA CGG TAT GAC      1786
Ala Met Ile Asp Asp Lys Val Ile Thr Lys Ile Gly Thr Arg Tyr Asp
        365             370             375

GTG GGC AAC TTA ATC CCG TCA GAC TTC CAT GTC GTT GCT CAC GGC AAC      1834
Val Gly Asn Leu Ile Pro Ser Asp Phe His Val Val Ala His Gly Asn
            380             385             390

AAT TAC TGC ATT TGG GAA AAG AGC GGT CTC AGA GTT CCT GCA GGG CGG      1882
Asn Tyr Cys Ile Trp Glu Lys Ser Gly Leu Arg Val Pro Ala Gly Arg
395             400             405

CAC CAC TAT TAGGCGAAGA AAATTTTTCA GGACTATTTG GTGCCTGGAA              1931
His His Tyr
410

TAAGATTTGA ATTATATCCT AAATAACCAG ATTATGATTG TATGAGATTT CTTAATCTGA    1991

GCAAAGCGTT GAGCATTGCT CCGATATTTC TATGTATTCT ACCTGCCTGG GGATATGATA   2051

TTTGTATCCT CTAGAAGTAA AGATGATTTT AACTC                              2086
```

( 2 ) INFORMATION FOR SEQ ID NO:2:

( i ) SEQUENCE CHARACTERISTICS:
( A ) LENGTH: 438 amino acids
( B ) TYPE: amino acid (D) TOPOLOGY: linear (ii) MOLECULE TYPE: protein (xi) SEQUENCE DESCRIPTION: SEQ ID NO:2:

| Met -26 | Ala -25 | Lys | Arg | Ile | Ala | Ser -20 | Met | Ser | Ser | Leu | Leu -15 | Leu | Ile | Ala | Leu |
| --- | --- | --- | --- | --- | --- | --- | --- | --- | --- | --- | --- | --- | --- | --- | --- |
| Leu -10 | Cys | Leu | Ser | Ser | His -5 | Leu | Ala | Gln | Ala | Gln 1 | Val | Leu | Phe | Gln | Gly 5 |
| Phe | Asn | Trp | Glu 10 | Ser | Trp | Lys | Lys | Gln 15 | Gly | Gly | Trp | Tyr | Asn 20 | Phe | Leu |
| His | Gly | His 25 | Val | Asp | Asp | Ile | Ala 30 | Ala | Thr | Gly | Val | Thr 35 | His | Val | Trp |
| Leu | Pro 40 | Pro | Pro | Ser | His 45 | Ser | Val | Ala | Pro | Gln 50 | Gly | Tyr | Met | Pro | Gly |
| Arg 55 | Leu | Tyr | Asp | Leu 60 | Asp | Ala | Ser | Lys | Tyr 65 | Gly | Thr | Gly | Ala | Glu | Leu 70 |
| Arg | Ser | Leu | Ile | Ala 75 | Ala | Phe | His | Ser | Lys 80 | Gly | Ile | Lys | Cys | Val 85 | Ala |
| Asp | Ile | Val | Ile 90 | Asn | His | Arg | Cys | Ala 95 | Asp | Tyr | Lys | Asp | Ser 100 | Arg | Gly |
| Ile | Tyr | Cys 105 | Ile | Phe | Glu | Gly | Gly 110 | Thr | Pro | Asp | Ser | Arg 115 | Leu | Asp | Trp |
| Gly | Pro 120 | Asp | Met | Ile | Cys 125 | Ser | Asp | Asp | Thr | Gln 130 | Tyr | Ser | Asn | Gly | Arg |
| Gly 135 | His | Arg | Asp | Thr | Gly 140 | Ala | Asp | Phe | Gly | Ala 145 | Ala | Pro | Asp | Ile | Asp 150 |
| His | Leu | Asn | Thr | Arg 155 | Val | Gln | Thr | Glu | Leu 160 | Ser | Asp | Trp | Leu | Asn 165 | Trp |
| Leu | Lys | Ser | Asp 170 | Val | Gly | Phe | Asp | Gly 175 | Trp | Arg | Leu | Asp | Phe 180 | Ala | Lys |
| Gly | Tyr | Ser 185 | Ala | Ala | Val | Ala | Lys 190 | Thr | Tyr | Val | Asp | Asn 195 | Thr | Asp | Pro |
| Ser | Phe 200 | Val | Val | Ala | Glu | Ile 205 | Trp | Ser | Asn | Met | Arg 210 | Tyr | Asp | Gly | Asn |
| Gly 215 | Glu | Pro | Ser | Trp | Asn 220 | Gln | Asp | Gly | Asp | Arg 225 | Gln | Glu | Leu | Val | Asn 230 |
| Trp | Ala | Gln | Ala | Val 235 | Gly | Gly | Pro | Ala | Ser 240 | Ala | Phe | Asp | Phe | Thr 245 | Thr |
| Lys | Gly | Glu | Leu 250 | Gln | Ala | Ala | Val | Gln 255 | Gly | Glu | Leu | Trp | Arg 260 | Met | Lys |
| Asp | Gly | Asn 265 | Gly | Lys | Ala | Pro | Gly 270 | Met | Ile | Gly | Trp | Leu 275 | Pro | Glu | Lys |
| Ala | Val 280 | Thr | Phe | Ile | Asp | Asn 285 | His | Asp | Thr | Gly | Ser 290 | Thr | Gln | Asn | Ser |
| Trp 295 | Pro | Phe | Pro | Ser | Asp 300 | Lys | Val | Met | Gln | Gly 305 | Tyr | Ala | Tyr | Ile | Leu 310 |
| Thr | His | Pro | Gly | Val 315 | Pro | Cys | Ile | Phe | Tyr 320 | Asp | His | Val | Phe | Asp 325 | Trp |
| Asn | Leu | Lys | Gln 330 | Glu | Ile | Ser | Thr | Leu 335 | Ala | Ala | Val | Arg | Ser 340 | Arg | Asn |
| Glu | Ile | His 345 | Pro | Gly | Ser | Lys | Leu 350 | Lys | Ile | Leu | Ala | Ala 355 | Glu | Gly | Asp |
| Val | Tyr 360 | Val | Ala | Met | Ile | Asp 365 | Asp | Lys | Val | Ile | Thr 370 | Lys | Ile | Gly | Thr |

```
Arg Tyr Asp Val Gly Asn Leu Ile Pro Ser Asp Phe His Val Val Ala
375                 380                 385                 390

His Gly Asn Asn Tyr Cys Ile Trp Glu Lys Ser Gly Leu Arg Val Pro
                395                 400                 405

Ala Gly Arg His His Tyr
                410
```

( 2 ) INFORMATION FOR SEQ ID NO:3:

( i ) SEQUENCE CHARACTERISTICS:
        ( A ) LENGTH: 4276 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Rice (Oryzae sativa)
        ( B ) STRAIN: CV. M202

( v i i ) IMMEDIATE SOURCE:
        ( A ) LIBRARY: (EMBL) genomic
        ( B ) CLONE: '-Amy7-C ( i x ) FEATURE:
        ( A ) NAME/KEY: CDS
        ( B ) LOCATION: join(2459..2473, 2582..2713, 2807..3619, 3704
            . . 3952)

( i x ) FEATURE:
        ( A ) NAME/KEY: mat_peptide
        ( B ) LOCATION: join(2459..2473, 2582..2713, 2807..3619, 3704
            . . 3952)

( x ) PUBLICATION INFORMATION:
        ( A ) AUTHORS: Yu et al., Su-May
        ( B ) TITLE: Regulation of '-amylase- encoding gene expression
            in germinating seeds and cultured cells of rice
        ( C ) JOURNAL: Gene
        ( D ) VOLUME: in press ( x i ) SEQUENCE DESCRIPTION: SEQ ID NO:3:

```
GCATGCGAGA  GGCACGGGGT  TCGATTCCCC  GCGTCTCCAT  CGGCACTGTT  TTTTAACATC      60

AAACGCTGTT  CGATCCACTA  TCTGTTAATT  TCGCAAACAC  AACTAAATCT  TTTTTTTTT      120

TTGCCGGTGC  GTGCAGTGTG  ACGTCCAAGG  CATGGCGCAT  TGGCGCCTCC  CCTCTTTCCC     180

TTGATCTTTT  CATCAGTTCG  TTCTTCTTGC  AGAAAAGCTG  TTCTGTTAAG  TCGGTTCCGA     240

TCTGCTCTTG  GGCTCTTGCC  AGAAACAACC  TGTGTACGCC  AGACTTATCA  AGCCAACCAT     300

CCTGATGAGC  CTCTGCTTAT  ACAAGCCTTT  GACTCCAAAA  AGGACGAGGC  GGCTTGCAGC     360

CGCACGGAAA  TAAGCCGACC  GATCCTTTAT  TGCTCTATCT  TTTTCCCTTG  GAATAAAAAA     420

CAGCCCAATT  AAAATCTGGG  ATGAAACTAT  GGCTAGCTGT  TCGCGGTGTC  AGTTCTCGGG     480

ACGCTACCGT  TGTTTTGTTT  GAACCGGAAT  GTTCAGGGCG  GTTCACACCA  TAGACTTGGA     540

GCCAAGTGGT  TCCATCCACA  AAATTTCTC   ATCTTGAATA  TTCTGTTATC  TGCCTCGACA     600

GACGCGCCAT  ATCCTGTGTT  CAGGAATGAA  TGTGCTACAG  CCAACGTGCT  GCATGAAATT     660

TGCTGAAATC  GTGCTAAAAT  GTGCATGGCA  ACAGGAACCT  GATGCCCTGG  TCCTGTGGAA     720

CTGCCACGGG  AAAGTATTTT  TTATAGCTAG  GTGCAATCGT  ATCTAGGTGT  ATACATGTCA     780

CCTACATAGC  TACTCCCCTT  TATCTTAAAA  TATAATAATT  TTTAACTCTC  AGTATTTGTC     840

CTAAAATATA  ACAAATTCTC  CATCAACATT  ATCTTCCCAA  CCAATCACAA  CCCTTCATCA     900

TTAATTTTTT  CCCCCTACCT  CCACTACTCA  TCTAATCACA  ACCCTCCAAC  ACTCACTTCT     960
```

```
ATCTACTTTC TTAATAACTG TCTTCAACCC TAAAACTTCT TATATTTTAG GACGGAGGGA      1020
GTATCTAAAT ATTTCATAAA AAAAATGTTA AGATAGATAA AGAAGATATA AACCCACTAT      1080
GCAAACATGC ACATCAAAAT TTAATTTACA GTAAAGAAAC AGAAATAACA TATTCTATTT      1140
GTGCTGGAGA TGTACTGTTC ACAATATTGT TTTTTATTT TTATTTATC TGATTATATA        1200
TCTGTTTCAG CCTTGCATGG TTGTGTATGT TTGTGTATAG ACTTATGCCA TTGTGATTGA      1260
TGCTACCAAT TATTTTCAGA CTATTTTTT ATAGAGGAAT TTTATAGTTC TTGAGAAAAT       1320
ACCTTGAAGT ATCTAAATTT TACACTAAAA TTGTTGGTAC CTTGAGGTAC AAAGTACCTA      1380
GAGGTACCAA ATTTTACTAG AAAATTGTGG CACCTTTAGG TACCTTCTCA AAAATAGTAC      1440
AATTATGGGC CGTTTTGGAT TTAGTGCCAA AACGTGCTCT ACAAATATTT TGATAGTTTG      1500
AACAGTGCAT AAGACGGGTT TGGTTTGAAG CCAAATCATT GGCATTGCCA ATGTCCAATT      1560
TGATATTTTC TATATTATGC TAAAAGCTTG GTTCTAAATT GGCCTCCAAC CAAATACAAC      1620
TCTACTCTAC CAAAAAATTT GTAGTGCCAA AACTTGCCTA GGTTTTGTCA CTACCAACAT      1680
TTTGGTAAGT ATTAAACCAA ACAAGCCCTA CATTTTTTA TGTACATTTA AGTTGTATGT       1740
AAATGATGGG TGCGGTTGCA CCTAGGTGAA AAAAAATACA TATTCGCCAC AACTCGCAAC      1800
ATGTACCAAT TCAGCAGCAA GTGTAAGAGA GAAGATTTCT CTCGTTTTAC ACGCGCACGT      1860
TCAATTCCTG AACTACTAAA CGGTATGATT TTTGCAAAA ATTTCTATA GGAAAGTTAC        1920
TTAAAAATTA TATTAATCTA TTTTAAAAT TAAAATAGT TAATACTCAA TTAATTATAC        1980
GTTAATGGCT CAGCTCGTTT TGCGTACATT CTCAATCGAT TCTTTTCCTC TGCTCTCAAA      2040
TGCTCTGTGT GCGATCAGGT ATTCATGTTC AGCTCGCACA AGCACAAGCA AGACAGATGG      2100
AATTCCTACT GACCTGCGCC TTTTGCATCG CTCCAACTCT CAAAGTCTCA AGGCCATTAA      2160
ATTGCCTATG GGCTCACCAG CCAATAACAA ACTCCGGCTG TTATCCATCC AATCCAGTGT      2220
CCCAAAGCAA CATTCAAGCC CAGCCAGGCC TCCAAAAGTT GCAAGTTGAG CATGGCAAAA      2280
TCCCCGGCAA TTCTCGACTA TAAATACCTG ACCAGACACA CCCAGGAGCT TCATCAATCA      2340
TCCATCTCCG AAGTGTGTCT GCAGCATGCA GGTGCTGAAC ACC ATG GTG AAC AAA       2395
                                                  Met Val Asn Lys
                                                  -25

CAC TTC TTG TCC CTT TCG GTC CTC ATC GTC CTC CTT GGC CTC TCC TCC       2443
His Phe Leu Ser Leu Ser Val Leu Ile Val Leu Leu Gly Leu Ser Ser
-20             -15                  -10

AAC TTG ACA GCC GGG CAA GTC CTG TTT CAG GTAAGAGATC GCCATGAGTT         2493
Asn Leu Thr Ala Gly Gln Val Leu Phe Gln
-5               1            5

GGGTTTCAGG CTTCAGTGAA CTGATCCGGT TTGTACTGA GCCTAAGAGA ATGATGCAGT      2553

GATGCTCTTG TGTTTGATGA TGATGCAG GGA TTC AAC TGG GAC TCG TGG AAG       2605
                              Gly Phe Asn Trp Asp Ser Trp Lys
                                                             10

GAG AAT GGC GGG TGG TAC AAC TTC CTG ATG GGC AAG GTG GAC GAC ATC       2653
Glu Asn Gly Gly Trp Tyr Asn Phe Leu Met Gly Lys Val Asp Asp Ile
         15              20              25

GCC GCA GCC GGC ATC ACC CAC GTC TGG CTC CCT CCG CCG TCT CAC TCT       2701
Ala Ala Ala Gly Ile Thr His Val Trp Leu Pro Pro Pro Ser His Ser
30               35              40               45

GTC GGC GAG CAA GGTGCGGTGC TCTGCTCTCT CGATCCCTC GTCGTCGCAC             2753
Val Gly Glu Gln

CATTGCCGGC AAAATACATG CACAGGTCGT TGAATTGCTT GAATGCTTCT GCA GGC        2809
                                                             Gly
                                                             50

TAC ATG CCT GGG CGG CTG TAC GAT CTG GAC GCG TCT AAG TAC GGC AAC       2857
```

```
Tyr Met Pro Gly Arg Leu Tyr Asp Leu Asp Ala Ser Lys Tyr Gly Asn
             55                  60                  65

GAG GCG CAG CTC AAG TCG CTG ATC GAG GCG TTC CAT GGC AAG GGC GTC         2905
Glu Ala Gln Leu Lys Ser Leu Ile Glu Ala Phe His Gly Lys Gly Val
         70                  75                  80

CAG GTC ATC GCC GAC ATC GTC ATC AAC CAC CGC ACG GCG GAG CAC AAG         2953
Gln Val Ile Ala Asp Ile Val Ile Asn His Arg Thr Ala Glu His Lys
         85                  90                  95

GAC GGC CGC GGC ATC TAC TGC CTC TTC GAG GGC GGG ACG CCC GAC TCC         3001
Asp Gly Arg Gly Ile Tyr Cys Leu Phe Glu Gly Gly Thr Pro Asp Ser
    100                 105                 110

CGC CTC GAC TGG GGC CCG CAC ATG ATC TGC CGC GAC GAC CCC TAC GGC         3049
Arg Leu Asp Trp Gly Pro His Met Ile Cys Arg Asp Asp Pro Tyr Gly
115                 120                 125                 130

GAT GGC ACC GGC AAC CCG GAC ACC GGC GCC GAC TTC GCC GCC GCG CCG         3097
Asp Gly Thr Gly Asn Pro Asp Thr Gly Ala Asp Phe Ala Ala Ala Pro
            135                 140                 145

GAC ATC GAC CAC CTC AAC AAG CGC GTC CAG CGG GAC CTC ATT GGC TGG         3145
Asp Ile Asp His Leu Asn Lys Arg Val Gln Arg Asp Leu Ile Gly Trp
            150                 155                 160

CTC GAC TGG CTC AAG ATG GAC ATC GGC TTC GAC GCG TGG CGC CTC GAC         3193
Leu Asp Trp Leu Lys Met Asp Ile Gly Phe Asp Ala Trp Arg Leu Asp
        165                 170                 175

TTC GCC AAG GGC TAC TCC GCC GAC ATG GCA AAG ATC TAC ATC GAC GCC         3241
Phe Ala Lys Gly Tyr Ser Ala Asp Met Ala Lys Ile Tyr Ile Asp Ala
    180                 185                 190

ACC GAG CCG AGC TTC GCC GTG GCC GAG ATA TGG ACG TCC ATG GCG AAC         3289
Thr Glu Pro Ser Phe Ala Val Ala Glu Ile Trp Thr Ser Met Ala Asn
195                 200                 205                 210

GGC GGG GAC GGC AAG CCG AAC TAC GAC CAG AAC GCG CAC CGG CAG GAG         3337
Gly Gly Asp Gly Lys Pro Asn Tyr Asp Gln Asn Ala His Arg Gln Glu
            215                 220                 225

CTG GTC AAC TGG GTC GAT CGT GTC GGC GGC GCC AAC AGC AAC GGC ACG         3385
Leu Val Asn Trp Val Asp Arg Val Gly Gly Ala Asn Ser Asn Gly Thr
            230                 235                 240

GCG TTC GAC TTC ACC ACC AAG GGC ATC CTC AAC GTC GCC GTG GAG GGC         3433
Ala Phe Asp Phe Thr Thr Lys Gly Ile Leu Asn Val Ala Val Glu Gly
        245                 250                 255

GAG CTG TGG CGC CTC CGC GGC GAG GAC GGC AAG GCG CCC GGC ATG ATC         3481
Glu Leu Trp Arg Leu Arg Gly Glu Asp Gly Lys Ala Pro Gly Met Ile
260                 265                 270

GGG TGG TGG CCG GCC AAG GCG ACG ACC TTC GTC GAC AAC CAC GAC ACC         3529
Gly Trp Trp Pro Ala Lys Ala Thr Thr Phe Val Asp Asn His Asp Thr
275                 280                 285                 290

GGC TCG ACG CAG CAC CTG TGG CCG TTC CCC TCC GAC AAG GTC ATG CAG         3577
Gly Ser Thr Gln His Leu Trp Pro Phe Pro Ser Asp Lys Val Met Gln
            295                 300                 305

GGC TAC GCA TAC ATC CTC ACC CAC CCC GGC AAC CCA TGC ATC                 3619
Gly Tyr Ala Tyr Ile Leu Thr His Pro Gly Asn Pro Cys Ile
            310                 315                 320

GTGAGTAGCC AACTCGATCA GAAATTCTGA ATCATCCTGC AAACTGATCG ATGAACTGAT       3679

GATAAATTCT GTAAAATTGT TCAG TTC TAC GAC CAT TTC TTC GAT TGG GGT         3730
                           Phe Tyr Asp His Phe Phe Asp Trp Gly
                                        325

CTC AAG GAG GAG ATC GAG CGC CTG GTG TCA ATC AGA AAC CGG CAG GGG         3778
Leu Lys Glu Glu Ile Glu Arg Leu Val Ser Ile Arg Asn Arg Gln Gly
330                 335                 340                 345

ATC CAC CCG GCG AGC GAG CTG CGC ATC ATG GAA GCT GAC AGC GAT CTC         3826
Ile His Pro Ala Ser Glu Leu Arg Ile Met Glu Ala Asp Ser Asp Leu
            350                 355                 360
```

```
TAC CTC GCG GAG ATC GAT GGC AAG GTG ATC ACA AAG ATT GGA CCA AGA          3874
Tyr Leu Ala Glu Ile Asp Gly Lys Val Ile Thr Lys Ile Gly Pro Arg
            365                 370                 375

TAC GAC GTC GAA CAC CTC ATC CCC GAA GGC TTC CAG GTC GTC GCG CAC          3922
Tyr Asp Val Glu His Leu Ile Pro Glu Gly Phe Gln Val Val Ala His
        380                 385                 390

GGT GAT GGC TAC GCA ATC TGG GAG AAA ATC TGAGCGCACG ATGACGAGAC            3972
Gly Asp Gly Tyr Ala Ile Trp Glu Lys Ile
    395                 400

TCTCAGTTTA GCAGATTTAA CCTGCGATTT TTACCCTGAC CGGTATACGT ATATACGTGC        4032

CGGCAACGAG CTGTATCCGA TCCGAATTAC GGATGCAATT GTCCACGAAG TACTTCCTCC        4092

GTAAATAAAG TAGGATCAGG GACATACATT TGTATGGTTT TACGAATAAT GCTATGCAAT        4152

AAAATTTGCA CTGCTTAATG CTTATGCATT TTTGCTTGGT TCGATTCTAC TGGTGAATTA        4212

TTGTTACTGT TCTTTTTACT TCTCGAGTGG CAGTATTGTT CTTCTACGAA AATTTGATGC        4272

GTAG                                                                    4276
```

( 2 ) INFORMATION FOR SEQ ID NO:4:

( i ) SEQUENCE CHARACTERISTICS:
        ( A ) LENGTH: 428 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Val Asn Lys His Phe Leu Ser Leu Ser Val Leu Ile Val Leu Leu
-25                 -20                 -15                 -10

Gly Leu Ser Ser Asn Leu Thr Ala Gly Gln Val Leu Phe Gln Gly Phe
            -5                   1                   5

Asn Trp Asp Ser Trp Lys Glu Asn Gly Gly Trp Tyr Asn Phe Leu Met
        10                  15                  20

Gly Lys Val Asp Asp Ile Ala Ala Ala Gly Ile Thr His Val Trp Leu
    25                  30                  35

Pro Pro Pro Ser His Ser Val Gly Glu Gln Gly Tyr Met Pro Gly Arg
40                  45                  50                  55

Leu Tyr Asp Leu Asp Ala Ser Lys Tyr Gly Asn Glu Ala Gln Leu Lys
            60                  65                  70

Ser Leu Ile Glu Ala Phe His Gly Lys Gly Val Gln Val Ile Ala Asp
        75                  80                  85

Ile Val Ile Asn His Arg Thr Ala Glu His Lys Asp Gly Arg Gly Ile
    90                  95                  100

Tyr Cys Leu Phe Glu Gly Gly Thr Pro Asp Ser Arg Leu Asp Trp Gly
105                 110                 115

Pro His Met Ile Cys Arg Asp Asp Pro Tyr Gly Asp Gly Thr Gly Asn
120                 125                 130                 135

Pro Asp Thr Gly Ala Asp Phe Ala Ala Ala Pro Asp Ile Asp His Leu
            140                 145                 150

Asn Lys Arg Val Gln Arg Asp Leu Ile Gly Trp Leu Asp Trp Leu Lys
            155                 160                 165

Met Asp Ile Gly Phe Asp Ala Trp Arg Leu Asp Phe Ala Lys Gly Tyr
        170                 175                 180

Ser Ala Asp Met Ala Lys Ile Tyr Ile Asp Ala Thr Glu Pro Ser Phe
    185                 190                 195

Ala Val Ala Glu Ile Trp Thr Ser Met Ala Asn Gly Gly Asp Gly Lys
```

|     | 200 |     |     | 205 |     |     |     | 210 |     |     |     | 215 |     |
|-----|-----|-----|-----|-----|-----|-----|-----|-----|-----|-----|-----|-----|-----|

Pro Asn Tyr Asp Gln Asn Ala His Arg Gln Glu Leu Val Asn Trp Val
                    220                 225             230

Asp Arg Val Gly Gly Ala Asn Ser Asn Gly Thr Ala Phe Asp Phe Thr
            235             240                 245

Thr Lys Gly Ile Leu Asn Val Ala Val Glu Gly Glu Leu Trp Arg Leu
        250             255                 260

Arg Gly Glu Asp Gly Lys Ala Pro Gly Met Ile Gly Trp Trp Pro Ala
    265             270                 275

Lys Ala Thr Thr Phe Val Asp Asn His Asp Thr Gly Ser Thr Gln His
280                 285                 290                 295

Leu Trp Pro Phe Pro Ser Asp Lys Val Met Gln Gly Tyr Ala Tyr Ile
                300                 305                 310

Leu Thr His Pro Gly Asn Pro Cys Ile Phe Tyr Asp His Phe Phe Asp
            315                 320                 325

Trp Gly Leu Lys Glu Glu Ile Glu Arg Leu Val Ser Ile Arg Asn Arg
            330                 335                 340

Gln Gly Ile His Pro Ala Ser Glu Leu Arg Ile Met Glu Ala Asp Ser
    345                 350                 355

Asp Leu Tyr Leu Ala Glu Ile Asp Gly Lys Val Ile Thr Lys Ile Gly
360                 365                 370                 375

Pro Arg Tyr Asp Val Glu His Leu Ile Pro Glu Gly Phe Gln Val Val
                380                 385                 390

Ala His Gly Asp Gly Tyr Ala Ile Trp Glu Lys Ile
            395                 400

( 2 ) INFORMATION FOR SEQ ID NO:5:

( i ) SEQUENCE CHARACTERISTICS:
        ( A ) LENGTH: 3314 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Rice (Oryzae sativa)
        ( B ) STRAIN: CV. M202

( v i i ) IMMEDIATE SOURCE:
        ( A ) LIBRARY: (EMBL) genomic
        ( B ) CLONE: '-Amy8-C ( i x ) FEATURE:
        ( A ) NAME/KEY: CDS
        ( B ) LOCATION: join(1152..1241, 1385..2323, 2409..2690)

( i x ) FEATURE:
        ( A ) NAME/KEY: mat_peptide
        ( B ) LOCATION: join(1227..1241, 1385..2323, 2409..2690)

( x ) PUBLICATION INFORMATION:
        ( A ) AUTHORS: Yu et al., Su-May
        ( B ) TITLE: Regulation of '-amylase- encoding gene expression
                in germinating seeds and cultured cells of rice
        ( C ) JOURNAL: Gene
        ( D ) VOLUME: in press ( x i ) SEQUENCE DESCRIPTION: SEQ ID NO:5:

```
GATATCCCGC CAGCACAGTG CCGGAAACTT TAATGCCGAT GGGGCTTTTA ATGCCGGTTG      60

AGAGCATATC GATACGGTTA CGAATTGGCG GCACCCACAG ATTCGCCAGC CCCGGCAGCC     120

GCACGGTGTT ATCCAGTTCC TCAATGATTT TGTCCATCGT CATGCCTGGC CGCCACTGCT     180
```

```
CCTGCGGCTT AAGCTGGATG GTCGTTTCTA CCATCTCCAG CGGACAGAAT CGGTGGCCGG        240
TTTCCGTTTC CCGGTTTTGC CAAATACCCG CGCCACTTCA GGTACGCTCA TAATTAGCTT        300
GTCGGTTTTT TGCAGCATAC CGCCGCCTCT GCTGCGGAAA TCCCCGGCAG CGTCGATGGC        360
ATATACACAA GTCGCCTTCA TTGATCTGCG GTAAAAATTC CCGCCAACTT TATTGAGCGG        420
CCAGAGAANN GTAGCACCGA AAGCNCCGCC ACCAGCAGCG TGGTTTTNNN CCAGTGCAGT        480
ACTTCAGCAA CACGGATGAT AAACACGAAT CAAAAGCGA TTGTGCGGGT TACTGCTTTC         540
CGGCGGAATT TTGCCACGGA TCTCCTTTCC AAAGAAAGTT TCCCTGCCGG CGCTTGATCC        600
GTCACACCGA TGACGCGACG CGGTAGAGGC CGGTACCTGT TCGAACAACC AACTGATCTG        660
CGGCTCCTCC GCTTGCGGCT TGCCTCTTAT CAACGTATCG CCGTTTCCGT CATGCGTGAT        720
CGGTGATCGA TCACCGAGAG AGACCGGACG ACGAGTCGAG AGAGCTCGCG CCGCCTCGAT        780
CGGCGCGGCG GTGACTCGAG CAGGGCCTGA AGTAGCTGCA CGGCTCAAGG CGGCACTCCA        840
TCACCGGACA CCGGGGTCCA GACTACTCGT TTCCGTTGGA GAAATAACCA CCTTTATCCA        900
TGTTGCTTAT CCGTGAATTG CAACAGCATT GATTGTTCGC GTTAATTCG CCTCGGCCAT         960
GTAACCTCCG ACCTGATCCT CTTGGACACT ATAAATAGAG GCCAGTTCAG GCAATGCAAG       1020
AGCAGAGAAG CAGAGTACAG CAGGCAGCTC TTCTTCTCTT TGCGAAGGTT GGCTACTTGG       1080
CCAGCCATTA GGAAACAAGT TAGTTTGGAG AAGAAGCAGA GTTGAGACTG CATTTGCATT       1140
```

```
GCTCTGTAGC C ATG GGC AAG CAC CAT GTC ACC CTG TGT TGT GTC GTT TTT       1190
             Met Gly Lys His His Val Thr Leu Cys Cys Val Val Phe
             -25         -20                 -15

GCT GTG CTC TGC CTG GCG TCC AGC TTA GCA CAA GCC CAA GTT CTC TTC        1238
Ala Val Leu Cys Leu Ala Ser Ser Leu Ala Gln Ala Gln Val Leu Phe
-10             -5                  1

CAG GTAGTTTAAT TTACTGACGC CTTGGTGAAA GTTTGTTAAT ACTTGATAAT            1291
Gln
 5

AATAATCTTG CACGGCAATA TAATGTACGC GCCGCAGTCA GGAAGCTTGA TTTGACCATG     1351
GGTTGCGTTT GGGTGTTTTT GCCGTACGTG CAG GGG TTT AAC TGG GAG TCG TGG     1405
                                     Gly Phe Asn Trp Glu Ser Trp
                                                              10

AGG AAG CAA GGC GGG TGG TAC AAC TTT CTG CAC GAG AAG GTG GAG GAG      1453
Arg Lys Gln Gly Gly Trp Tyr Asn Phe Leu His Glu Lys Val Glu Glu
        15                  20                  25

ATC GCC AGC ACG GGC GCC ACC CAC GTC TGG CTC CCG CCG CCG TCG CAC      1501
Ile Ala Ser Thr Gly Ala Thr His Val Trp Leu Pro Pro Pro Ser His
        30                  35                  40

TCT GTC TCG CCG CAG GGT TAC ATG CCG GGG CGG CTC TAC GAC CTG GAC      1549
Ser Val Ser Pro Gln Gly Tyr Met Pro Gly Arg Leu Tyr Asp Leu Asp
45                  50                  55                  60

GCG TCC AAG TAC GGC ACG GAG GCG GAG CTC AAG TCG CTG ATC GAG GCA      1597
Ala Ser Lys Tyr Gly Thr Glu Ala Glu Leu Lys Ser Leu Ile Glu Ala
        65                  70                  75

TTC CAC GAC AAG AAC GTC GAG TGC CTC GCC GAC ATC GTC ATC AAC CAC      1645
Phe His Asp Lys Asn Val Glu Cys Leu Ala Asp Ile Val Ile Asn His
        80                  85                  90

CGC TGC GCC GAC TAC AAG GAC AGC CGC GGC GTG TAC TGC GTG TTC GAG      1693
Arg Cys Ala Asp Tyr Lys Asp Ser Arg Gly Val Tyr Cys Val Phe Glu
        95                  100                 105

GGC GGC ACG CCC GAC GGC CGC CTC GAC TGG GGC CCC GAC ATG ATC TGC      1741
Gly Gly Thr Pro Asp Gly Arg Leu Asp Trp Gly Pro Asp Met Ile Cys
110                 115                 120

AGC GAC GAC ACG CAG TAC TCC AAC GGC CGC GGC CAC CGC GAC ACC GGC      1789
Ser Asp Asp Thr Gln Tyr Ser Asn Gly Arg Gly His Arg Asp Thr Gly
```

```
                     125                          130                          135                          140
          GCC GGG TTC GGC GCC GCG CCC GAC ATC GAC CAC CTC AAC CCG CGT GTC                                              1837
          Ala Gly Phe Gly Ala Ala Pro Asp Ile Asp His Leu Asn Pro Arg Val
                          145                          150                          155
          CAG CGG GAG CTC ACC GAC TGG CTC AAC TGG CTC AGG ACC CAC CTC GGC                                              1885
          Gln Arg Glu Leu Thr Asp Trp Leu Asn Trp Leu Arg Thr His Leu Gly
                          160                          165                          170
          TTC GAC GGA TGG CGC CTC GAC TTC GCG AAG GGC TAC TCC GCG CCG CTG                                              1933
          Phe Asp Gly Trp Arg Leu Asp Phe Ala Lys Gly Tyr Ser Ala Pro Leu
                          175                          180                          185
          GCG AGG ATC TAC GTC GAC AAC ACC AAC CCG ACG TTC GTC GTC GGC GAG                                              1981
          Ala Arg Ile Tyr Val Asp Asn Thr Asn Pro Thr Phe Val Val Gly Glu
                          190                          195                          200
          ATC TGG AGC TCG CTC ATC TAC AAC GGC GAC GGC AAG CCG TCG ACC AAC                                              2029
          Ile Trp Ser Ser Leu Ile Tyr Asn Gly Asp Gly Lys Pro Ser Thr Asn
          205                          210                          215                          220
          CAG GAC GCG GAC AGG CAG GAG CTG GTG AAC TGG GTG GAG GGC GTC GGC                                              2077
          Gln Asp Ala Asp Arg Gln Glu Leu Val Asn Trp Val Glu Gly Val Gly
                          225                          230                          235
          AAG CCG GCG ACG GCG TTC GAC TTC ACC ACC AAG GGC ATC CTC CAG GCC                                              2125
          Lys Pro Ala Thr Ala Phe Asp Phe Thr Thr Lys Gly Ile Leu Gln Ala
                          240                          245                          250
          GCC GTG CAG GGC GAG CTG TGG AGG CTC CAC GAC GGC AAC GGC AAG GCG                                              2173
          Ala Val Gln Gly Glu Leu Trp Arg Leu His Asp Gly Asn Gly Lys Ala
                          255                          260                          265
          CCC GGC CTC ATG GGG TGG ATG CCC GAT CAG GCC GTA ACC TTC GTC GAC                                              2221
          Pro Gly Leu Met Gly Trp Met Pro Asp Gln Ala Val Thr Phe Val Asp
                          270                          275                          280
          AAC CAC GAC ACC GGC TCG ACC CAG TCG CTC TGG CCG TTC CCT TCC GAC                                              2269
          Asn His Asp Thr Gly Ser Thr Gln Ser Leu Trp Pro Phe Pro Ser Asp
          285                          290                          295                          300
          AAG GTC ATG CAG GGC TAC GCC TAC ATC CTC ACT CAC CCT GGC ATC CCA                                              2317
          Lys Val Met Gln Gly Tyr Ala Tyr Ile Leu Thr His Pro Gly Ile Pro
                          305                          310                          315
          TGC ATC GTAAGTATCA CCACCGAAAT CTTTCTCATC AAATTCGTTC ATATTGGTGA                                               2373
          Cys Ile
          GCTCATTGCT GGTGCATGTG TACGTGTGTA TGCAG TTC TAC GAC CAT GTG TTC                                               2426
                                                  Phe Tyr Asp His Val Phe
                                                                  320
          GAC TGG AAC CTG CAG CAC GAG ATC GCG ACG CTG GCT GAA ATC CGG TCA                                              2474
          Asp Trp Asn Leu Gln His Glu Ile Ala Thr Leu Ala Glu Ile Arg Ser
          325                          330                          335                          340
          AGG AAC GGG ATC CAT GCG GAG AGC ACG CTG GAC ATC CTC AAG GCC GAG                                              2522
          Arg Asn Gly Ile His Ala Glu Ser Thr Leu Asp Ile Leu Lys Ala Glu
                          345                          350                          355
          GGG GAC ATC TAC GTC GCC ATG ATC GAC GGC AAG GTG ATC ACC AAG CTC                                              2570
          Gly Asp Ile Tyr Val Ala Met Ile Asp Gly Lys Val Ile Thr Lys Leu
                          360                          365                          370
          GGG CCG AGG TAC GAC GCC GGC GGG ATC ATC CCC TCC GAC TTC CAT GTC                                              2618
          Gly Pro Arg Tyr Asp Ala Gly Gly Ile Ile Pro Ser Asp Phe His Val
                          375                          380                          385
          GTG GCG CAC GGC AAC GAC TAC TGC GTC TGG GAG AAG GAA GGC CTC AGG                                              2666
          Val Ala His Gly Asn Asp Tyr Cys Val Trp Glu Lys Glu Gly Leu Arg
                          390                          395                          400
          GTT CCT GCC GGT AGA AAG CAC TAT TAGCTTTAGC TATAGCGATC GAGTTGCATG                                             2720
          Val Pro Ala Gly Arg Lys His Tyr
          405                          410
          GTGCTTTGCA ACCCTAGATA ATATATATAC GTACGTGGCT CTAGCTATGA ATCATGCAAT                                            2780
          TTTGCTGCGA GATGTGTACG AGCGAGCTTC GATCGATGTA CGCTTCGTTA TAACTAGCGT                                            2840
```

```
TCTTCGGAAA TAAGTAATCG GAATGTACCC TGTTAATCCT GCAGAAATGT AGGATGAATG    2900
GAATTAACTA GCTACTGTTC GTTCGATCC TCAAGAAAGA CTTGCAAGAT CTTGTCCAGT    2960
TGACTTCAGT TTTTTACTCC CGCTTTTAGC GTCTGGATAC CGTGGTGGAT TGAAAGCTCA   3020
ACTTGATCCC GTTTGGCCCA GCAATATTAG GCCGTAAGTA AAACGAATGA CACCTGCATA   3080
TTCCGGCCCA AAGCGCACGC TCGTTGTCTC TCATTTAGCG GTCCAAAGAT AATGGGACGA   3140
ATGTTCTTCA CAGCAACGAT TTAGCCTAAC TATAATGGGG CACCTTTCCT TTATAACCCA   3200
AGGAATAAGT TCACTGGTCC CTTAATTTAT CAGCGAGTCT GAAATTTATC CCTAAACCGA   3260
AATACTGTAT ATAATTGGTC CCCCAATTTT CAAAACGGTT CACTTAGAGG ACCC          3314
```

( 2 ) INFORMATION FOR SEQ ID NO:6:

( i ) SEQUENCE CHARACTERISTICS:
        ( A ) LENGTH: 437 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Gly Lys His His Val Thr Leu Cys Cys Val Phe Ala Val Leu
-25             -20              -15              -10

Cys Leu Ala Ser Ser Leu Ala Gln Ala Gln Val Leu Phe Gln Gly Phe
            -5                   1                    5

Asn Trp Glu Ser Trp Arg Lys Gln Gly Gly Trp Tyr Asn Phe Leu His
            10                  15                   20

Glu Lys Val Glu Glu Ile Ala Ser Thr Gly Ala Thr His Val Trp Leu
        25                  30                  35

Pro Pro Pro Ser His Ser Val Ser Pro Gln Gly Tyr Met Pro Gly Arg
40                      45                  50                  55

Leu Tyr Asp Leu Asp Ala Ser Lys Tyr Gly Thr Glu Ala Glu Leu Lys
                60                  65                  70

Ser Leu Ile Glu Ala Phe His Asp Lys Asn Val Glu Cys Leu Ala Asp
                75                  80                  85

Ile Val Ile Asn His Arg Cys Ala Asp Tyr Lys Asp Ser Arg Gly Val
            90                  95                  100

Tyr Cys Val Phe Glu Gly Gly Thr Pro Asp Gly Arg Leu Asp Trp Gly
105                     110                 115

Pro Asp Met Ile Cys Ser Asp Asp Thr Gln Tyr Ser Asn Gly Arg Gly
120                     125                 130                 135

His Arg Asp Thr Gly Ala Gly Phe Gly Ala Ala Pro Asp Ile Asp His
                140                 145                 150

Leu Asn Pro Arg Val Gln Arg Glu Leu Thr Asp Trp Leu Asn Trp Leu
                155                 160                 165

Arg Thr His Leu Gly Phe Asp Gly Trp Arg Leu Asp Phe Ala Lys Gly
            170                 175                 180

Tyr Ser Ala Pro Leu Ala Arg Ile Tyr Val Asp Asn Thr Asn Pro Thr
        185                 190                 195

Phe Val Val Gly Glu Ile Trp Ser Ser Leu Ile Tyr Asn Gly Asp Gly
200                     205                 210                 215

Lys Pro Ser Thr Asn Gln Asp Ala Asp Arg Gln Glu Leu Val Asn Trp
                220                 225                 230

Val Glu Gly Val Gly Lys Pro Ala Thr Ala Phe Asp Phe Thr Thr Lys
            235                 240                 245
```

| Gly | Ile | Leu | Gln | Ala | Ala | Val | Gln | Gly | Glu | Leu | Trp | Arg | Leu | His | Asp |
|-----|-----|-----|-----|-----|-----|-----|-----|-----|-----|-----|-----|-----|-----|-----|-----|
|     |     | 250 |     |     |     |     | 255 |     |     |     |     | 260 |     |     |     |

| Gly | Asn | Gly | Lys | Ala | Pro | Gly | Leu | Met | Gly | Trp | Met | Pro | Asp | Gln | Ala |
|-----|-----|-----|-----|-----|-----|-----|-----|-----|-----|-----|-----|-----|-----|-----|-----|
|     | 265 |     |     |     |     | 270 |     |     |     |     | 275 |     |     |     |     |

| Val | Thr | Phe | Val | Asp | Asn | His | Asp | Thr | Gly | Ser | Thr | Gln | Ser | Leu | Trp |
|-----|-----|-----|-----|-----|-----|-----|-----|-----|-----|-----|-----|-----|-----|-----|-----|
| 280 |     |     |     |     | 285 |     |     |     | 290 |     |     |     |     |     | 295 |

| Pro | Phe | Pro | Ser | Asp | Lys | Val | Met | Gln | Gly | Tyr | Ala | Tyr | Ile | Leu | Thr |
|-----|-----|-----|-----|-----|-----|-----|-----|-----|-----|-----|-----|-----|-----|-----|-----|
|     |     |     |     | 300 |     |     |     |     | 305 |     |     |     |     | 310 |     |

| His | Pro | Gly | Ile | Pro | Cys | Ile | Phe | Tyr | Asp | His | Val | Phe | Asp | Trp | Asn |
|-----|-----|-----|-----|-----|-----|-----|-----|-----|-----|-----|-----|-----|-----|-----|-----|
|     |     |     | 315 |     |     |     |     | 320 |     |     |     |     | 325 |     |     |

| Leu | Gln | His | Glu | Ile | Ala | Thr | Leu | Ala | Glu | Ile | Arg | Ser | Arg | Asn | Gly |
|-----|-----|-----|-----|-----|-----|-----|-----|-----|-----|-----|-----|-----|-----|-----|-----|
|     |     | 330 |     |     |     |     | 335 |     |     |     |     | 340 |     |     |     |

| Ile | His | Ala | Glu | Ser | Thr | Leu | Asp | Ile | Leu | Lys | Ala | Glu | Gly | Asp | Ile |
|-----|-----|-----|-----|-----|-----|-----|-----|-----|-----|-----|-----|-----|-----|-----|-----|
|     | 345 |     |     |     |     | 350 |     |     |     |     | 355 |     |     |     |     |

| Tyr | Val | Ala | Met | Ile | Asp | Gly | Lys | Val | Ile | Thr | Lys | Leu | Gly | Pro | Arg |
|-----|-----|-----|-----|-----|-----|-----|-----|-----|-----|-----|-----|-----|-----|-----|-----|
| 360 |     |     |     |     | 365 |     |     |     |     | 370 |     |     |     |     | 375 |

| Tyr | Asp | Ala | Gly | Gly | Ile | Ile | Pro | Ser | Asp | Phe | His | Val | Val | Ala | His |
|-----|-----|-----|-----|-----|-----|-----|-----|-----|-----|-----|-----|-----|-----|-----|-----|
|     |     |     |     | 380 |     |     |     |     | 385 |     |     |     |     | 390 |     |

| Gly | Asn | Asp | Tyr | Cys | Val | Trp | Glu | Lys | Glu | Gly | Leu | Arg | Val | Pro | Ala |
|-----|-----|-----|-----|-----|-----|-----|-----|-----|-----|-----|-----|-----|-----|-----|-----|
|     |     |     | 395 |     |     |     |     | 400 |     |     |     |     | 405 |     |     |

| Gly | Arg | Lys | His | Tyr |
|-----|-----|-----|-----|-----|
|     |     | 410 |     |     |

( 2 ) INFORMATION FOR SEQ ID NO:7:

( i ) SEQUENCE CHARACTERISTICS:
        ( A ) LENGTH: 1519 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Rice (Oryzae sativa)
        ( B ) STRAIN: CV. Labelle ( v i i ) IMMEDIATE SOURCE:
        ( A ) LIBRARY: (Lambda gt-11) cDNA
        ( B ) CLONE: '-Amy10-C ( x ) PUBLICATION INFORMATION:
        ( A ) AUTHORS: Yu et al., Su-May
        ( B ) TITLE: Regulation of '-amylase- encoding gene expression
            in germinating seeds and cultured cells of rice
        ( C ) JOURNAL: Gene
        ( D ) VOLUME: in press ( x i ) SEQUENCE DESCRIPTION: SEQ ID NO:7:

```
AGCAAACGCT TCTTGTCCCT GTCCCTGCTC ATCCTCCTCC TCGGCTTCTC CTCCAGCTTG      60
GCAGCCGGGC AAGTCCTGTT TCAGGGCTTC AACTGGGAGT CGTGGAAGGA GAATGGCGGG     120
TGGTACAACA TGCTGATGGG CAAGGTGGAC GACATCGCCG CCGCCGGCAT CACCCACGTC     180
TGGCTCCCTC CGCCGTCTCA ATCTGTCGCC GAACAAGGCT ACATGCCGGG GCGGCTGTAC     240
GATCTGGACG CTTCCAAGTA CGGCAACGAG GCGCAGCTCA AGTCGCTGAT CGAGGCGTTC     300
CACGGCAAGG GCGTCCAGGT GATCGCCGAC ATCGTCATCA ACCACCGCAC GGCGGCAGCA     360
AGCACAGGAC GGCCGCGGCA TCTACTGCCT CTTCGAGGGC GGGCAGCGCG ACTCCCGCCT     420
CGACTGGGGC CCGCACATGA TCTGCCGCGG CGACCCCTAC GGCGACGGCA CCGGCAACCG     480
ACACCGCTAG CCGACTTGGC CTGACATCGA CCACCTCAAC AAGCGCGTCA CGAGCTCATC     540
GGCTGGCTCG ACTGGCTCGA CTGGCTCAAG CATAGGAACC AATTGGGCCT TCGACCCTGA     600
```

-continued

| | | | | | | |
|---|---|---|---|---|---|---|
| CTGGCCTCCT | CGACTTCCGC | CAACGCGCGC | GTTACTCCCG | CCGTACGTAT | CTGCAAAGAG | 660 |
| CTATCATCGA | CTGCCACCGA | GACCGGACTA | TCGCCGATGG | CCGAGACTAT | AGGACGTACG | 720 |
| CTGGCGTAGC | GAGCTGCGGG | ACGGCTAAAG | CCGGACTATG | ACCATGAACG | CAACGACCGG | 780 |
| CAGTAGCTGG | TCAACTGGGT | CGACCGTGCG | GCTGGACCAA | CATCATTCTA | AATGCTTCGA | 840 |
| CTTCACCACC | TAATGGGCAT | ACTCAACGAA | TCGCCAGCTT | GGTAGGTGCG | AGCTATTGGC | 900 |
| GCCTCCTGGG | CGTAGAGACG | GCCAAGGCGC | CACAGGCATG | CATTACGGAG | TAGTGGCCGG | 960 |
| CTAAGGGACG | ACCTTTGATC | TGACGAACCA | CTGACTACCA | GGCGTCGATC | CGCAGCATCA | 1020 |
| TGTGGCTGTT | TCCCTCCGAC | AAGGTCATGC | AGGGTACGCT | ACAGTACTCA | CCACCCGGCA | 1080 |
| ACCCATGCAC | TTTCTACGAC | CATTTCTTCG | ACTGGGGCCA | CAAGGAGGAG | ATCGAGCGCC | 1140 |
| TGGTATCGAC | TCAAGAAACC | GCAGGGATCC | ACCCGGCGAG | CGAGCTGCGT | ATCATGGAGG | 1200 |
| CTGACAGCGA | TCTCTACCTC | GCCGAGATCG | ACGGAAAGGT | CATCACGAAG | GTCGGACCAA | 1260 |
| GATACGACGT | CGAGCACCTC | ATCCCGAAGC | TTCCAGGTCG | TCGCGCACGT | GACGGCTACC | 1320 |
| GTCTGGGAGA | AATTGAGCGG | TGGAGAGGCC | ATTAAAGCAG | ATTTATTTCC | TGCATTTTCA | 1380 |
| CCTCGACGTA | TAACATATAC | ATGTGATGGC | AACGAGTTGT | ATGCTGTATC | TGATCTGAAC | 1440 |
| TATGTACGCG | ATTGTCCACA | AAGTACTACC | TCCGTAAATA | AAGTGAGGAT | ATGGAACATG | 1500 |
| CGTTTGCATG | CATGGTTTT | | | | | 1519 |